(12) United States Patent
Cindrich et al.

(10) Patent No.: US 12,115,326 B2
(45) Date of Patent: Oct. 15, 2024

(54) INFLATION DEVICE WITH TOGGLE-LOCKING TRIGGER

(71) Applicant: Merit Medical Systems, Inc., South Jordan, UT (US)

(72) Inventors: Christopher Cindrich, Highland, UT (US); Richard P. Jenkins, Bluffdale, UT (US); Michael Dean Haslam, Sandy, UT (US); Craig Purdy, Sunnyvale, CA (US); Gregory R. McArthur, Sandy, UT (US); Nate Shirley, Pleasant Grove, UT (US); David J. Johnson, Mountain View, CA (US); Eron Flory, The Sea Ranch, CA (US); Jon Davis, Sandy, UT (US)

(73) Assignee: Merit Medical Systems, Inc., South Jordan, UT (US)

( * ) Notice: Subject to any disclaimer, the term of this patent is extended or adjusted under 35 U.S.C. 154(b) by 660 days.

(21) Appl. No.: 17/197,979

(22) Filed: Mar. 10, 2021

(65) Prior Publication Data

US 2021/0283382 A1    Sep. 16, 2021

Related U.S. Application Data

(60) Provisional application No. 62/988,277, filed on Mar. 11, 2020.

(51) Int. Cl.
A61M 25/10    (2013.01)

(52) U.S. Cl.
CPC .............................. *A61M 25/10182* (2013.11)

(58) Field of Classification Search
CPC ............................................... A61M 25/10182
See application file for complete search history.

(56) References Cited

U.S. PATENT DOCUMENTS

| | | | |
|---|---|---|---|
| 5,306,248 A | 4/1994 | Barrington | |
| 5,713,869 A | 2/1998 | Morejon | |
| 2014/0088499 A1* | 3/2014 | Lampropoulos | A61M 25/10182 604/97.02 |
| 2018/0110640 A1 | 4/2018 | Brister et al. | |
| 2018/0243540 A1 | 8/2018 | Sykes et al. | |

FOREIGN PATENT DOCUMENTS

WO    2014047030    3/2014

OTHER PUBLICATIONS

International Search Report and Written Opinion dated Jun. 30, 2021 for PCT/US2021/021768.

* cited by examiner

*Primary Examiner* — Bradley J Osinski
(74) *Attorney, Agent, or Firm* — Dorsey & Whitney LLP

(57) ABSTRACT

Devices used to pressurize, depressurize, or otherwise displace fluid are disclosed. The devices may be configured to displace fluid in order to inflate or deflate a medical device, such as a balloon. The devices include a trigger configured to convert the devices from a pressurization state to a priming state. The devices further include a locking or toggle member configured to toggle and/or maintain the devices in a priming state.

14 Claims, 34 Drawing Sheets

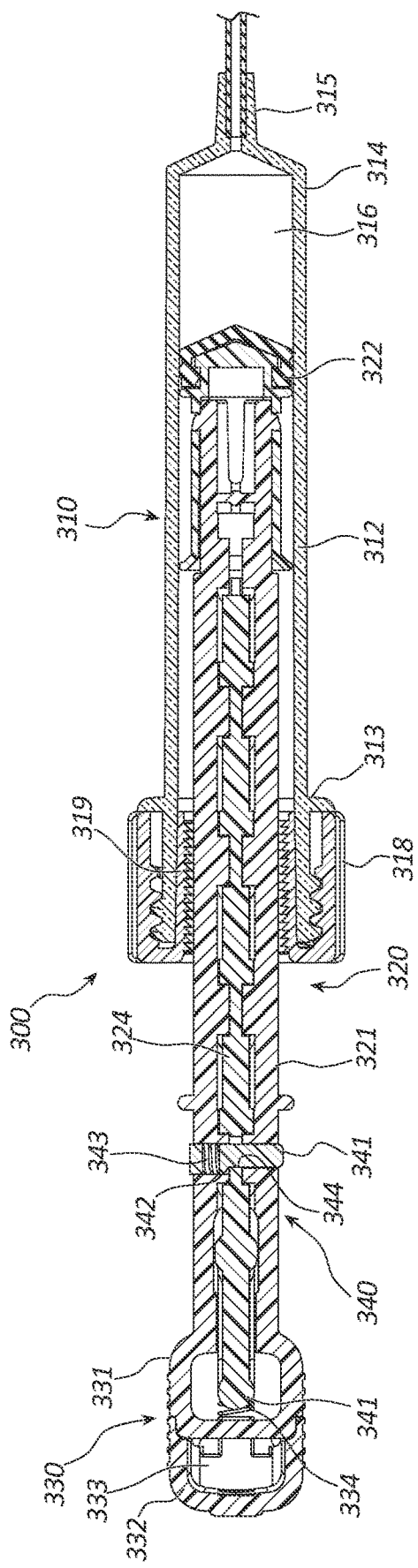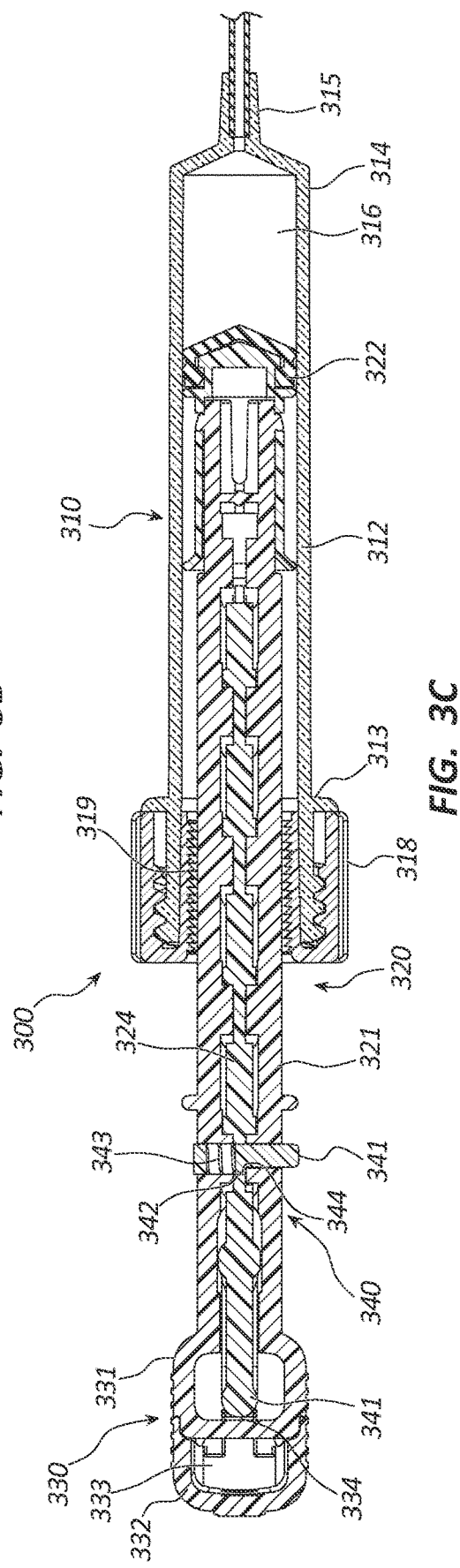
FIG. 3B
FIG. 3C

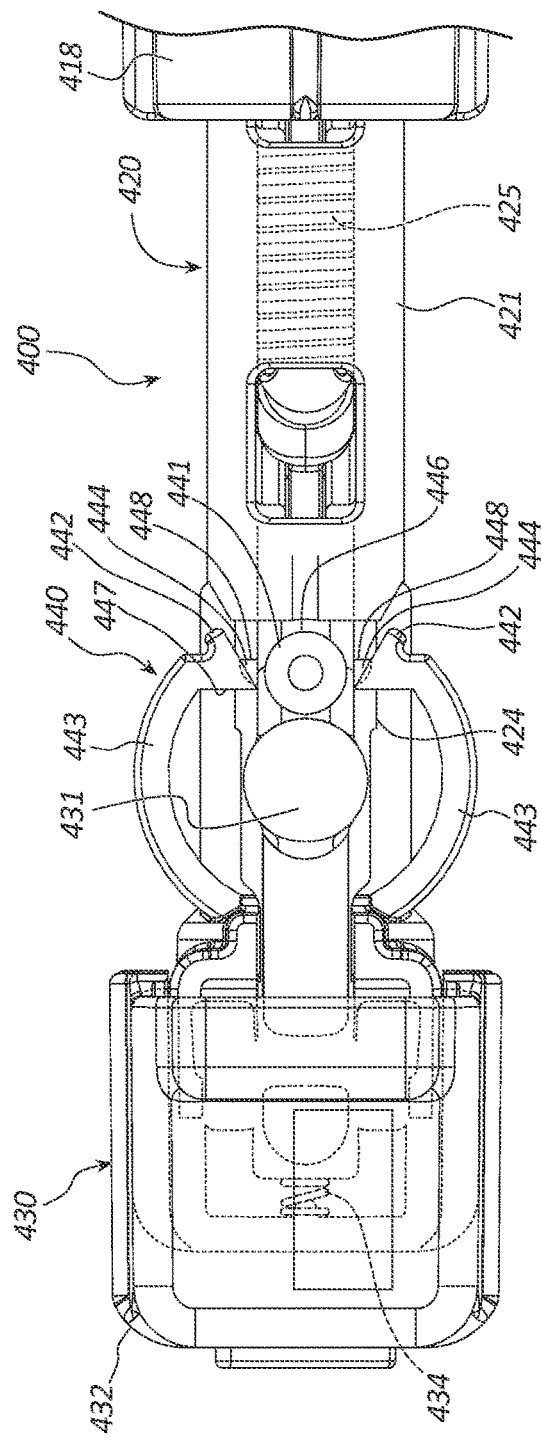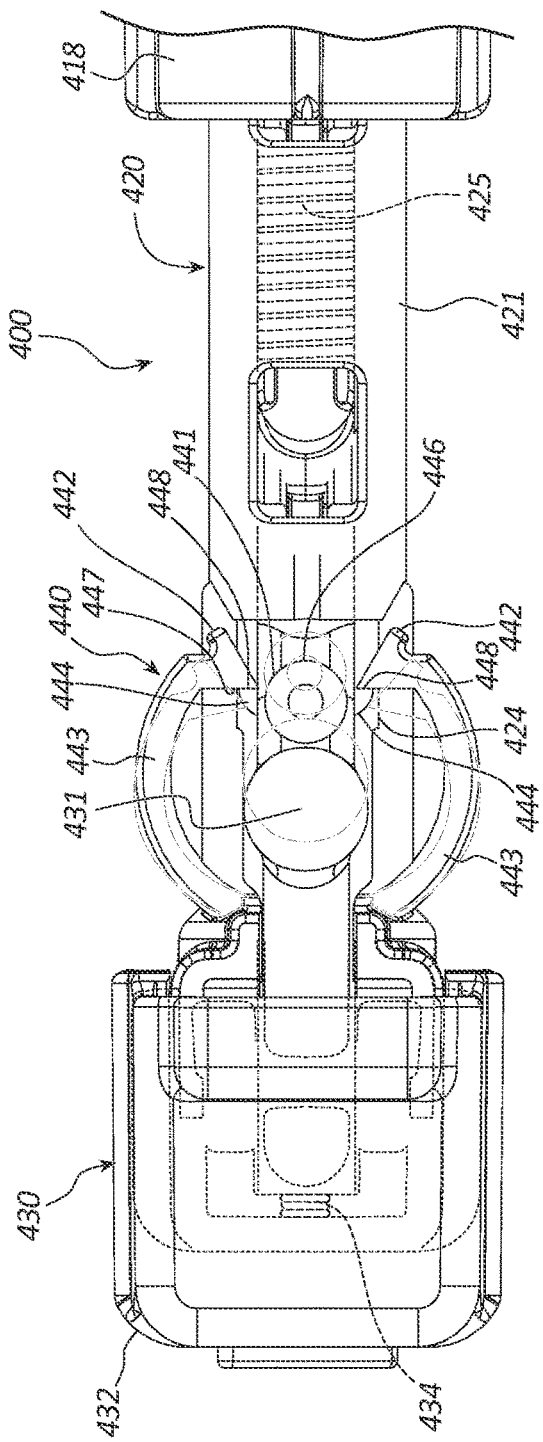
FIG. 4B
FIG. 4C

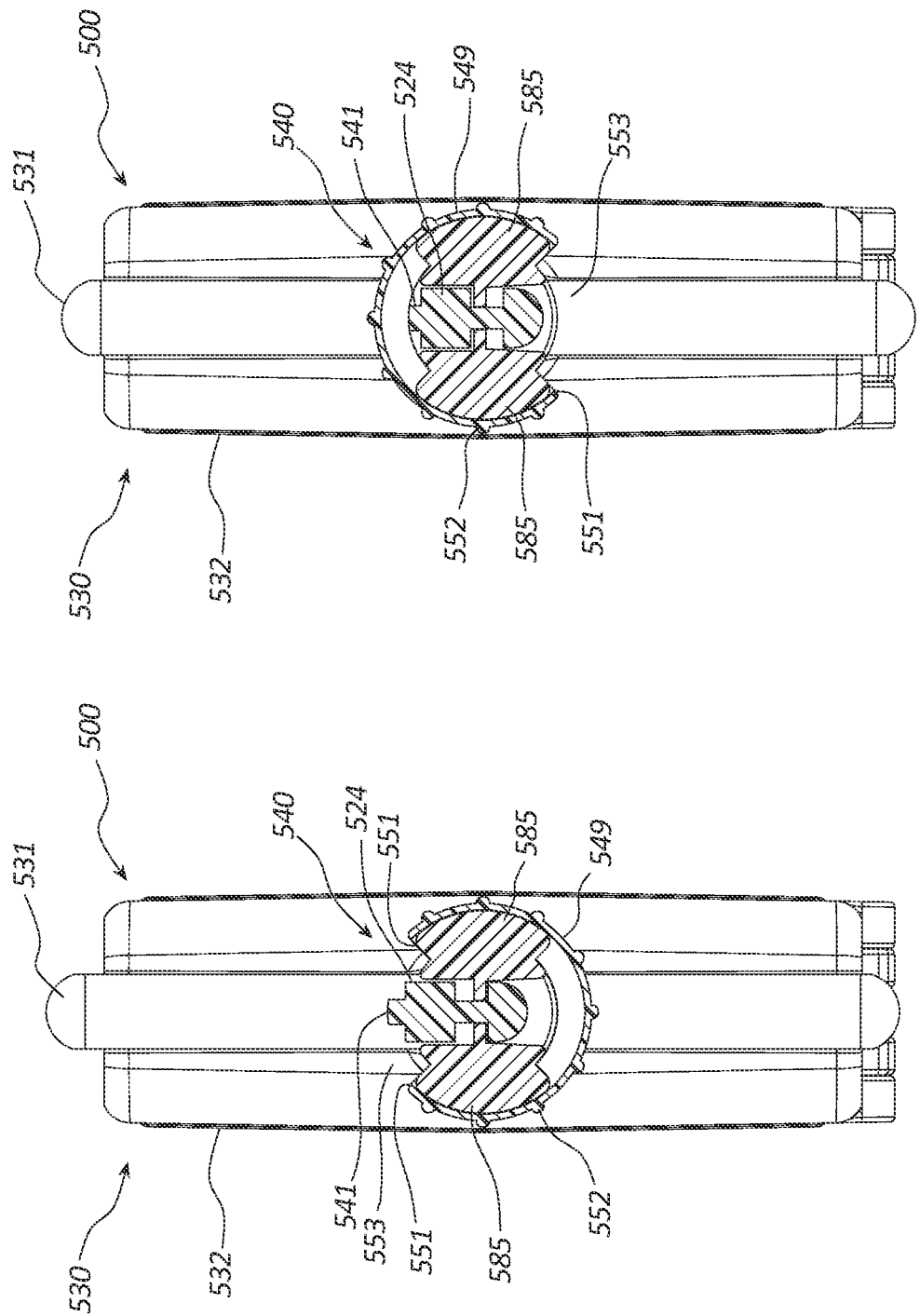

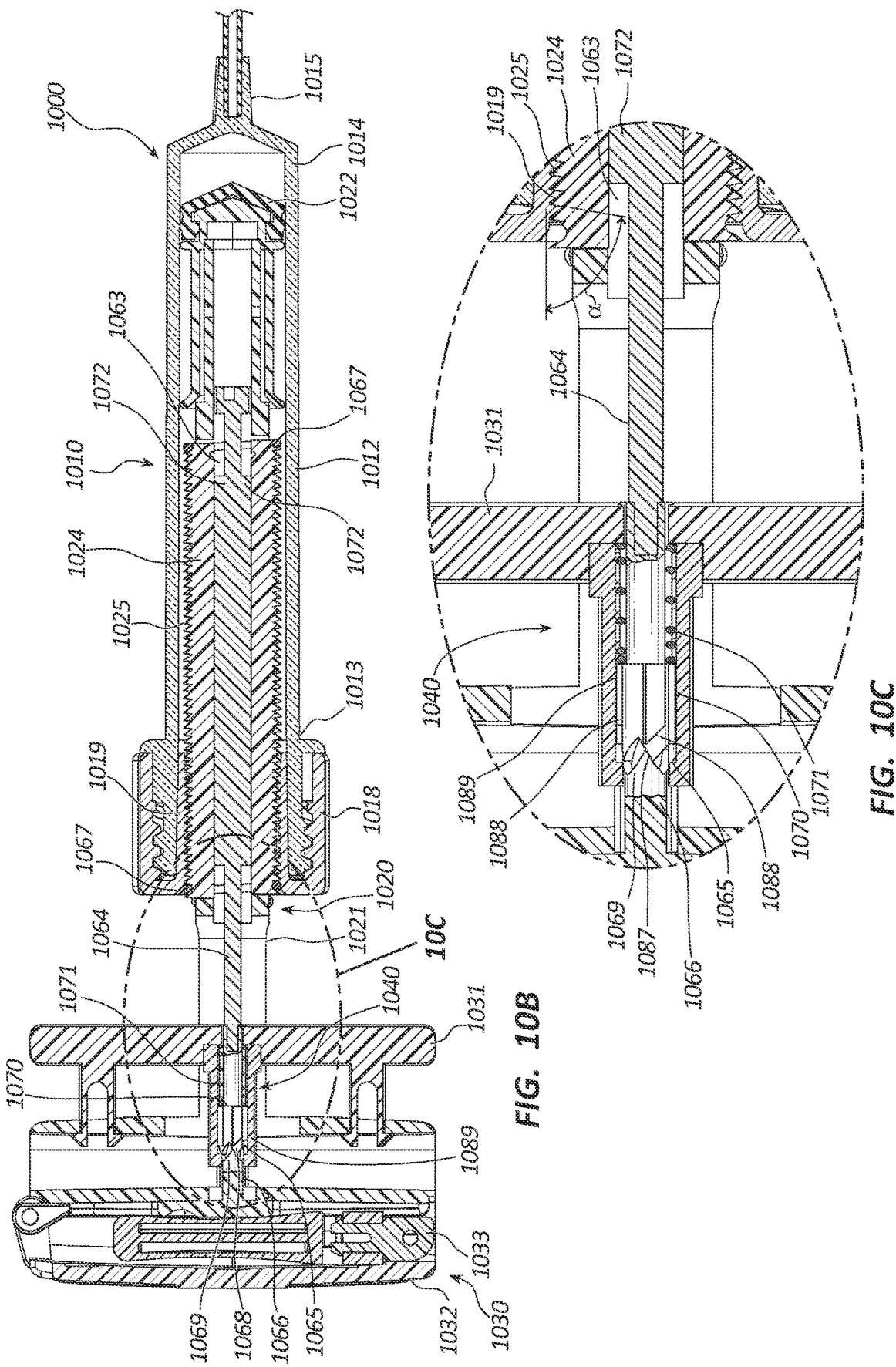

INFLATION DEVICE WITH TOGGLE-LOCKING TRIGGER

RELATED APPLICATIONS

This application claims priority to U.S. Provisional Application No. 62/988,277, filed on Mar. 11, 2020 and titled, "Inflation Device with Toggle-Locking Trigger," which is hereby incorporated by reference in its entirety.

TECHNICAL FIELD

The present disclosure relates generally to devices used to pressurize, depressurize, or otherwise displace fluid, particularly in medical devices. More specifically, in some embodiments, the present disclosure relates to high-pressure devices used to pressurize, depressurize, or otherwise displace fluid along a line.

BRIEF DESCRIPTION OF THE DRAWINGS

The embodiments disclosed herein will become more fully apparent from the following description and appended claims, taken in conjunction with the accompanying drawings. These drawings depict only typical embodiments, which will be described with additional specificity and detail through use of the accompanying drawings in which:

FIG. 3B is a cross-sectional view, taken through plane 3B-3B of FIG. 3A, of the inflation device of FIG. 3A in a pressurization state.

FIG. 3C is a cross-sectional view, taken through plane 3B-3B of FIG. 3A, of the inflation device of FIG. 3A in a priming state.

FIG. 4B is a detail view of a portion of the inflation device of FIG. 4A in a pressurization state.

FIG. 4C is a detail view of a portion of the inflation device of FIG. 4A in a priming state.

FIG. 5B is a cross-sectional view, taken through plane 5B-5B of FIG. 5A, of the inflation device of FIG. 5A in a pressurization state.

FIG. 5C is a cross-sectional view, taken through plane 5B-5B of FIG. 5A, of the inflation device of FIG. 5A in a priming state.

FIG. 10B is a cross-sectional view, taken through plane 10B-10B of FIG. 10A, of the inflation device of FIG. 10A in a pressurization state.

FIG. 10C is a cross-sectional view of the detail portion indicated in FIG. 10B.

DETAILED DESCRIPTION

Figure 1A:
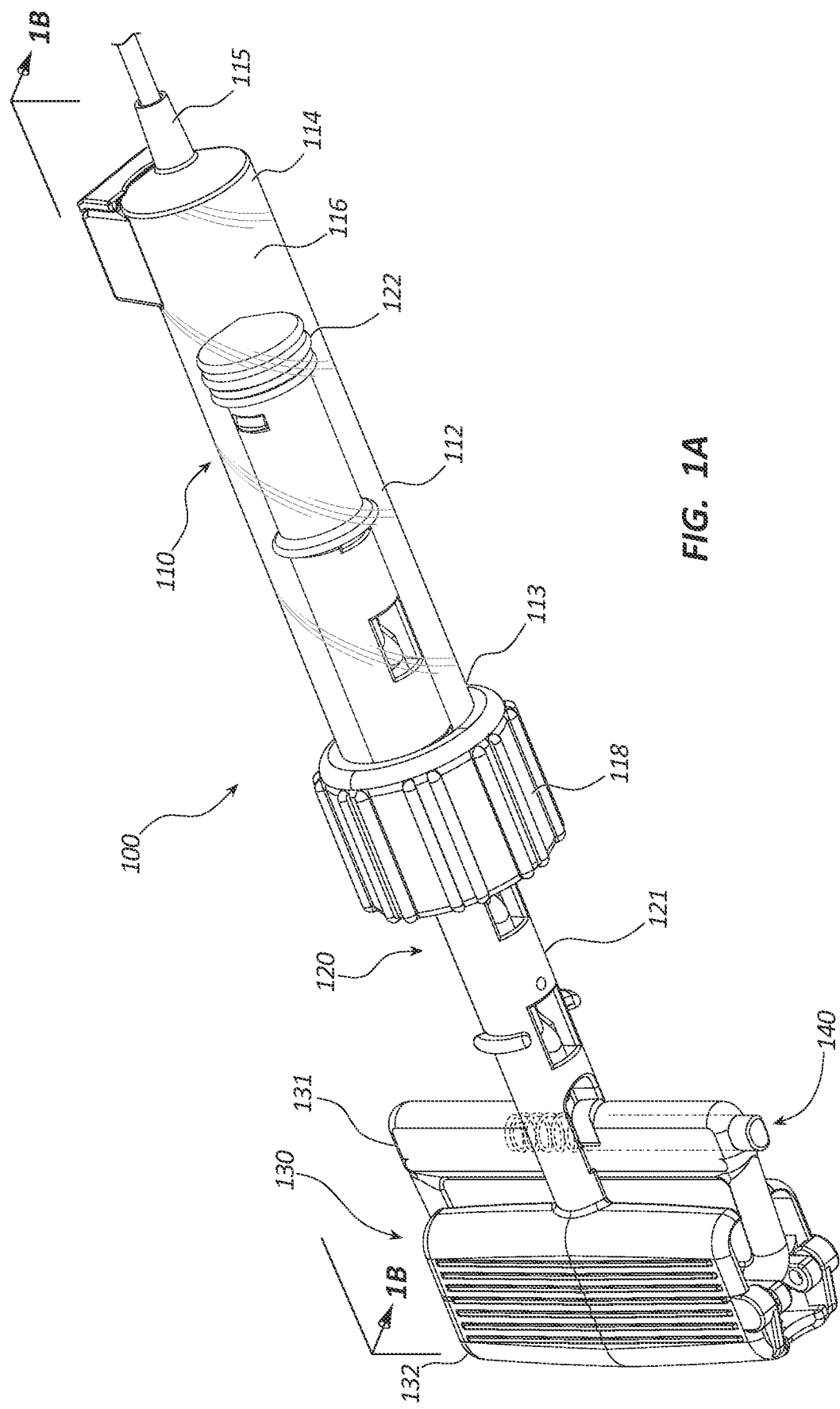
FIG. 1A is a perspective view of an embodiment of an inflation device with a trigger locking member.

An inflation device may include an inflation syringe which utilizes threads to advance or retract a plunger by rotating the plunger handle relative to the body of the syringe such that the threads cause longitudinal displacement of the plunger relative to the body. In some instances, an inflation syringe may further include retractable threads, enabling a practitioner to disengage the threads and displace the plunger by simply pushing or pulling the plunger.

An inflation syringe may comprise a coupling member configured to constrain movement of the plunger within the syringe body. The coupling member may comprise threads configured to engage with the retractable threads. Certain inflation devices include a member in the handle of the device which allows the practitioner to disengage the threads through manipulating the member. For example, in some instances the handle of such a device may include a "trigger" portion which may be configured to retract threads positioned on the plunger that were engaged with the coupling member when the trigger is actuated, thereby disengaging the threads from the coupling member. Other inflation devices may include a member configured to manually or automatically lock the "trigger" portion in a retracted position such that the trigger does not need to be held by a practitioner.

In some therapies, the inflation syringe may be used by a practitioner to inflate a medical device such as a balloon at an end of a catheter to expand a caliber of a vessel or lumen of a body cavity. In some instances, the handle of the inflation syringe may be manually rotated by the practitioner when the threads are engaged to inflate and deflate the balloon during a procedure. The handle rotation may be achieved by repeated supination/pronation of the wrist and forearm. In other instances, the handle of the device may be displaced longitudinally to quickly inflate or deflate the balloon during a procedure.

In other therapies, the inflation syringe may be used by a practitioner to pressurize a fluid reservoir to facilitate delivery of a fluid, such as bone cement, to a portion of the patient's body, such as a vertebra.

Embodiments may be understood by reference to the drawings, wherein like parts are designated by like numerals throughout. It will be readily understood by one of ordinary skill in the art having the benefit of this disclosure that the components of the embodiments, as generally described and illustrated in the figures herein, could be arranged and designed in a wide variety of different configurations. Thus, the following more detailed description of various embodiments, as represented in the figures, is not intended to limit the scope of the disclosure, but is merely representative of various embodiments. While the various aspects of the embodiments are presented in drawings, the drawings are not necessarily drawn to scale unless specifically indicated.

Various features are sometimes grouped together in a single embodiment, figure, or description thereof for the purpose of streamlining the disclosure. Many of these features may be used alone and/or in combination with one another.

The phrases "coupled to" and "in communication with" refer to any form of interaction between two or more entities, including mechanical, electrical, magnetic, electromagnetic, fluid, and thermal interaction. Two components may be coupled to or in communication with each other even though they are not in direct contact with each other. For example, two components may be coupled to or in communication with each other through an intermediate component.

The directional terms "distal" and "proximal" are given their ordinary meaning in the art. That is, the distal end of a medical device means the end of the device furthest from the practitioner during use. The proximal end refers to the opposite end, or the end nearest the practitioner during use. As specifically applied to the syringe portion of an inflation device, the proximal end of the syringe refers to the end nearest the handle and the distal end refers to the opposite end, the end nearest the inlet/outlet port of the syringe. Thus, if at one or more points in a procedure a physician changes the orientation of a syringe, as used herein, the term "proximal end" always refers to the handle end of the syringe (even if the distal end is temporarily closer to the physician).

"Fluid" is used in its broadest sense, to refer to any fluid, including both liquids and gases as well as solutions, compounds, suspensions, etc., which generally behave as fluids.

FIGS. 1A-12C illustrate different views of several inflation devices and related components. In certain views each device may be coupled to, or shown with, additional components not included in every view. Further, in some views only selected components are illustrated, to provide detail into the relationship of the components. Some components may be shown in multiple views, but not discussed in connection with every view. Disclosure provided in connection with any figure may be relevant and analogously applicable to disclosure provided in connection with other figures or embodiments.

Figure 1B:
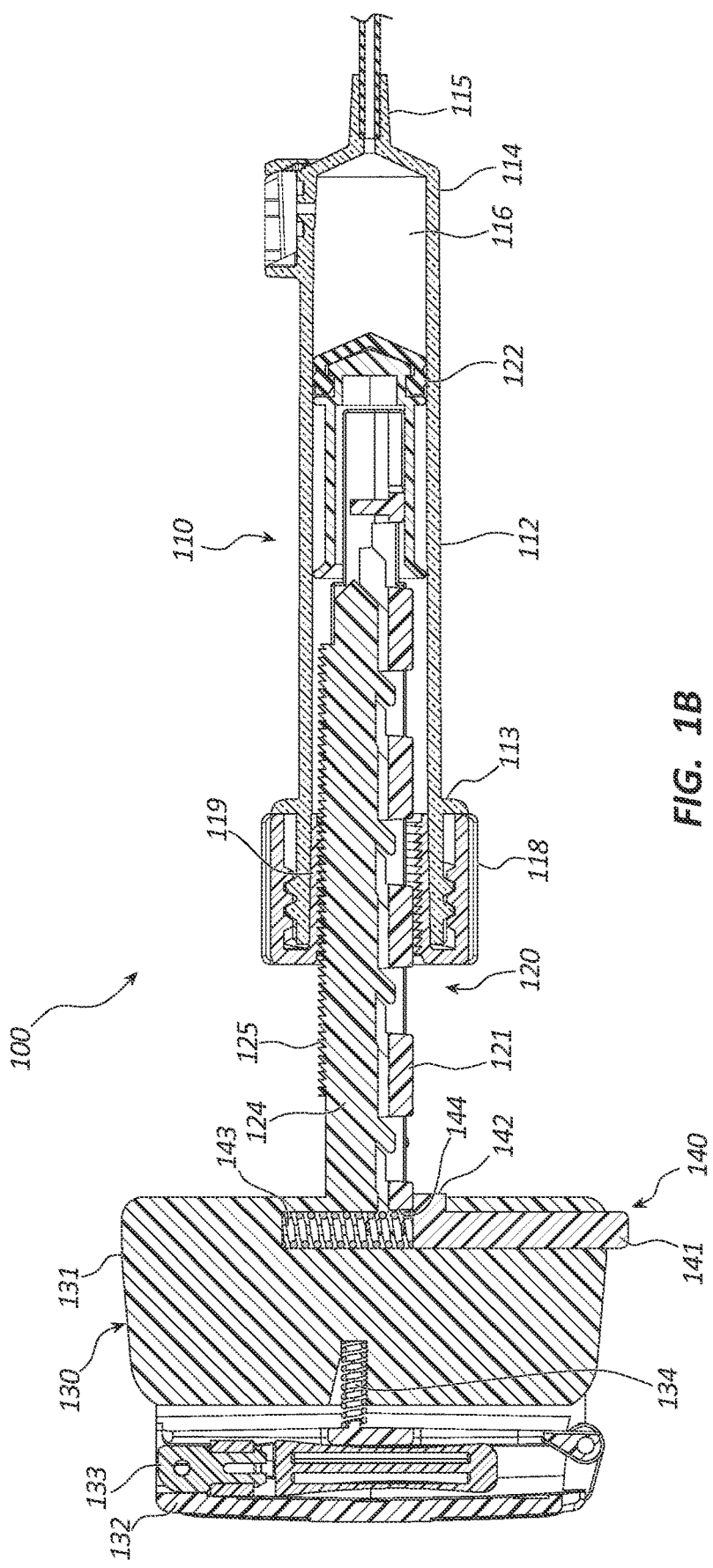
FIG. 1B is a cross-sectional view, taken through plane 1B-1B of FIG. 1A, of the inflation device of FIG. 1A in a pressurization state.
Figure 1C:
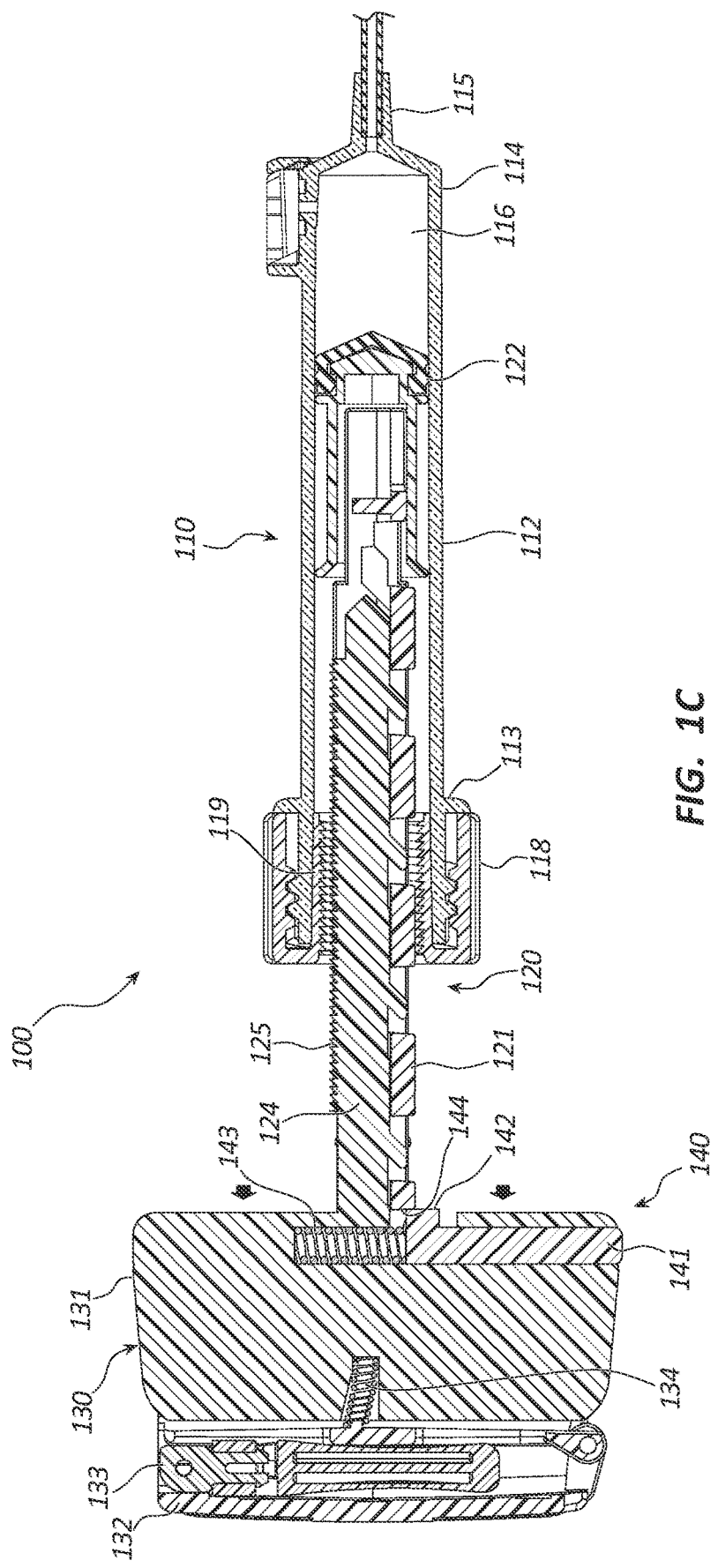
FIG. 1C is a cross-sectional view, taken through plane 1B-1B of FIG. 1A, of the inflation device of FIG. 1A in a priming state.

FIGS. 1A-1C depict one embodiment of an inflation device 100. In the illustrated embodiment, the inflation device 100 is partially comprised of a syringe 110. The inflation device 100 includes three broad groups of components; each group may have numerous subcomponents and parts. The three broad component groups are: a body component such as syringe body 112, a pressurization component such as a plunger 120, and a handle 130.

The syringe body 112 may be formed of a generally cylindrical hollow tube configured to receive the plunger 120. The syringe body 112 may include an inlet/outlet port 115 located adjacent the distal end 114 of the syringe body 112. In some embodiments, a coupling member 118 may be coupled to the syringe body 112 adjacent the proximal end 113 of the syringe body 112. The coupling member 118 may include a center aperture configured to allow the plunger 120 to pass through the coupling member 118 into the syringe body 112. Further, the coupling member 118 may include coupling member threads 119 configured to selectively couple the coupling member 118 to the plunger 120. For example, the coupling member 118 may comprise a polymeric nut at the proximal end 113 of the syringe body 112.

The plunger 120 may be configured to be longitudinally displaceable within the syringe body 112. The plunger 120 may be comprised of a plunger shaft 121 coupled to a plunger seal 122 at the distal end of the plunger shaft 121. The plunger shaft 121 may also be coupled to the handle 130 at the proximal end of the plunger shaft 121, with the plunger shaft 121 spanning the distance between the plunger seal 122 and the handle 130.

The handle 130 broadly refers to the group of components coupled to the proximal end of the plunger 120, some of which may be configured to be graspable by a user. In certain embodiments, the handle 130 may be configured such that the user may manipulate the position of the plunger 120 by manipulating the handle 130. Further, in some embodiments, the handle 130 may be an actuator mechanism configured to manipulate components of the inflation device 100.

Any and every component disclosed in connection with any of the exemplary handle configurations herein may be optional. That is, though the handle 130 broadly refers to the components coupled to the proximal end of the plunger shaft which may be configured to be graspable by a user, use of the term "handle" is not meant to indicate that every disclosed handle component is always present. Rather, the term is used broadly, referring to the collection of components, but not specifically referring to or requiring the inclusion of any particular component. Likewise, other broad groupings of components disclosed herein, such as the syringe 110 or syringe body 112 and the plunger 120, may also refer to collections of individual subcomponents. Use of these terms should also be considered non-limiting, as each subcomponent may or may not be present in every embodiment.

As shown in FIGS. 1A-1C, a fluid reservoir 116 may be defined by the space enclosed by the inside walls of the syringe body 112 between the plunger seal 122 and the distal end 114 of the syringe body 112. Accordingly, longitudinal movement of the plunger seal 122 with respect to the syringe body 112 will alter the size and volume of the fluid reservoir 116.

In some embodiments, the syringe 110 may include the coupling member 118, fixedly coupled to the proximal end 113 of the syringe body 112. The coupling member 118 may utilize threads or other coupling mechanisms to fixedly couple the coupling member 118 to corresponding threads on the syringe body 112. Additionally, the coupling member 118 may engage rail threads 125 configured to couple the plunger 120 to the coupling member 118. The plunger 120 may thus be translated longitudinally with respect to the syringe body 112 by rotating the plunger 120 such that the interaction of the coupling member threads 119 and the plunger threads 125 results in the longitudinal translation of the plunger 120. Such rotating motion may be achieved when a practitioner grasps the handle 130 and rotates it clockwise to extend the plunger 120 distally or counterclockwise to retract the plunger 120 proximally.

Thus, when the plunger threads 125 and the coupling member threads 119 are engaged, movement of the plunger 120 is constrained with respect to the syringe body 112, though the plunger 120 is not necessarily fixed with respect to the syringe body 112. For example, the plunger 120 may be rotatable, but not directly translatable, when the threads are engaged.

The plunger threads 125 may be configured such that they may be retracted within the plunger shaft 121. In some embodiments, the plunger threads 125 do not extend 360 degrees around the axis of the plunger shaft 121. For example, the plunger threads 125 may be formed on a thread rail 124 on the plunger shaft 121. The thread rail 124 may be retracted from the coupling member threads 119 by actuating a mechanism such as a trigger 131.

The retractable plunger threads 125 may allow a practitioner to displace the plunger shaft 121 relative to the syringe body 112 either through rotation of the plunger shaft (and the subsequent interaction of threads), or by retracting the plunger threads 125 and displacing the plunger shaft 121 by applying opposing forces on the plunger shaft and the syringe body 112. (Such forces may move the plunger shaft distally or proximally with respect to the syringe body 112.) Both methods of displacement may be utilized during the course of a single therapy.

In some instances, a practitioner may desire to quickly displace the plunger shaft 121, for instance, while priming the inflation device or while priming or deflating an attached medical device such as a balloon. Quick displacement of the plunger shaft 121 may be accomplished by retracting the plunger threads 125 and sliding the plunger shaft 121 relative to the syringe body 112. For example, a practitioner may quickly fill the fluid reservoir 116 with fluid by disengaging the plunger threads 125 and pulling the plunger shaft 121 in a proximal direction with respect to the syringe body 112. Further, a practitioner may quickly force fluid into lines leading to a medical device or quickly expel unwanted air bubbles from the fluid reservoir 116 by retracting the plunger threads 125 and repositioning the plunger shaft 121.

In other instances, the practitioner may desire more precise control over the position of the plunger shaft 121 (for example when displacing the plunger shaft in order to adjust the fluid pressure within the fluid reservoir 116) or it may simply be difficult to displace the plunger shaft 121 due to high fluid pressure within the fluid reservoir 116. In these instances, the practitioner may opt to displace the plunger shaft 121 by rotation of the plunger shaft 121.

As illustrated in FIGS. 1B-1C, the handle 130 includes a grip portion 132 and a trigger 131. The grip portion 132 may be configured to be gripped by a hand of a user. While gripping, the user may either rotate the handle 130 or longitudinally displace the handle 130 to inflate or deflate a medical device in fluid communication with the syringe 110. A crank member 133 may be selectively disposed within the grip portion 132. The crank member 133 may be configured to be selectively extended laterally from the grip portion 132 to provide rotational leverage when the handle 130 is rotated. The plunger shaft 121 extends distally from the grip portion 132. The plunger shaft 121 may be fixedly coupled to the grip portion 132.

As depicted in FIGS. 1A-1C, the trigger 131 is operatively coupled to the grip portion 132. The trigger 131 is shown to extend distally from the grip portion 132. The trigger 131 may be configured to be longitudinally displaced relative to the grip portion 132. The thread rail 124 extends distally from the trigger 131 and is fixedly coupled to the trigger 131. The trigger 131 may be configured to be gripped with fingers of the user to displace the trigger 131 and thread rail 124 proximally to a priming state when a proximally directed force is applied by the fingers. When displaced proximally, the thread rail threads 125 disengage from the coupling member threads 119 to allow the handle 130 to be longitudinally translated in response to externally applied longitudinal forces.

As shown, the trigger 131 includes a trigger locking member 140. The locking member 140 may be configured to maintain the trigger 131 and the thread rail in the priming state without continued application of the proximally directed force on the trigger 131 by an external element, such as the practitioner's fingers. In certain embodiments, a locking member of an inflation device may be configured to be actuated and de-actuated either manually or automatically. In some embodiments, a locking member may be operatively coupled to a plunger shaft or a grip portion of a handle or to a coupling member.

As shown in FIGS. 1B-1C the locking member 140 of the illustrated embodiment, comprises an elongate pin 141, a latch member 142, and a compliant member 143. The pin 141 is disposed within a closed channel within the grip 131 with a portion of the pin 141 extending radially outward from the trigger 131 prior to actuation. The pin 141 may have a circular cross-section. In other embodiments, the pin 141 may have any other suitable shaped cross-section. For example, the cross-section of the pin 141 may be oval, triangular, square, rectangular, or any other suitable polygonal shape. The pin 141 may be formed from any suitable semi-rigid or rigid polymeric material, such as styrene, polycarbonate, polyoxymethylene, acrylonitrile butadiene styrene, nylon, etc. In the illustrated embodiment, the latch member 142 is disposed at an end of the pin 141. A portion of the latch member 142 extends proximally outside of a circumference of the pin 141. The latch member 142 may be configured to engage with a shoulder member 144 of the plunger shaft 121 to lock the plunger shaft 121 in the priming state. The compliant member 143 is disposed within a closed channel in axial alignment with the pin 141. The compliant member 143 may be a coiled spring or any other suitable compliant member.

A handle configured to provide a locking member when retracting a thread rail may be desirable for certain therapies that require frequent or extended priming or deflating of medical devices. A handle providing a locking member may make devices configured for such therapies easier to use.

According to one potential use of the inflation device 100, the user grips the handle 130 and applies a proximally directed finger force to the trigger 131 to displace the trigger 131 proximally. Proximal displacement of the trigger 131 radially retracts the thread rail 124 and configures the inflation device 100 in the priming state. While the trigger 131 is displaced proximally, the user may apply a radial inwardly directed force to the pin 141. The pin 141 may then compress the resilient member 143 in response to this force such that the latch member 142 engages with the shoulder member 144 to lock the thread rail 124 in a retracted state. In other words, the trigger 131 may be prevented from distal displacement when the thread rail 124 is locked in the retracted state, which corresponds to a configuration wherein the inflation device 100 is locked in the priming state. The engagement of the latch member 142 and the shoulder member 144 is maintained by a distally directed force applied to the trigger 131 by a trigger compliant member 134. The trigger compliant member 134 is compressed when the trigger 131 is displaced proximally. In some embodiments, the latch member 142 may include a lip to help maintain engagement with the shoulder member. The user may then longitudinally translate the plunger 120 to prime or deflate the inflatable medical device in fluid communication with the inflation device 100 without maintaining the proximally directed finger force on the trigger.

The locking member 140 may be disengaged by applying a proximally directed force to the trigger 131. The distally directed force applied to the latch member 142 and the shoulder member 144 may be relieved as the compliant member 143 forces the pin 141 radially outward to disengage the latch member 142 from the shoulder member 144. The user releases the trigger 131 and the trigger compliant member 134 applies a distally directed force to the trigger 131 to displace the thread rail 124 distally and radially outward such that the thread rail threads 125 engage with the coupling nut threads 119. Other embodiments, such as embodiments wherein the locking member 140 is biased to a locking position (and manually unlocked) and wherein the locking member 140 is displaced both from the locking position and into the locking position manually (e.g. without displacement caused by a compliant member such as compliant member 143) are likewise within the scope of this disclosure.

Figure 2A:
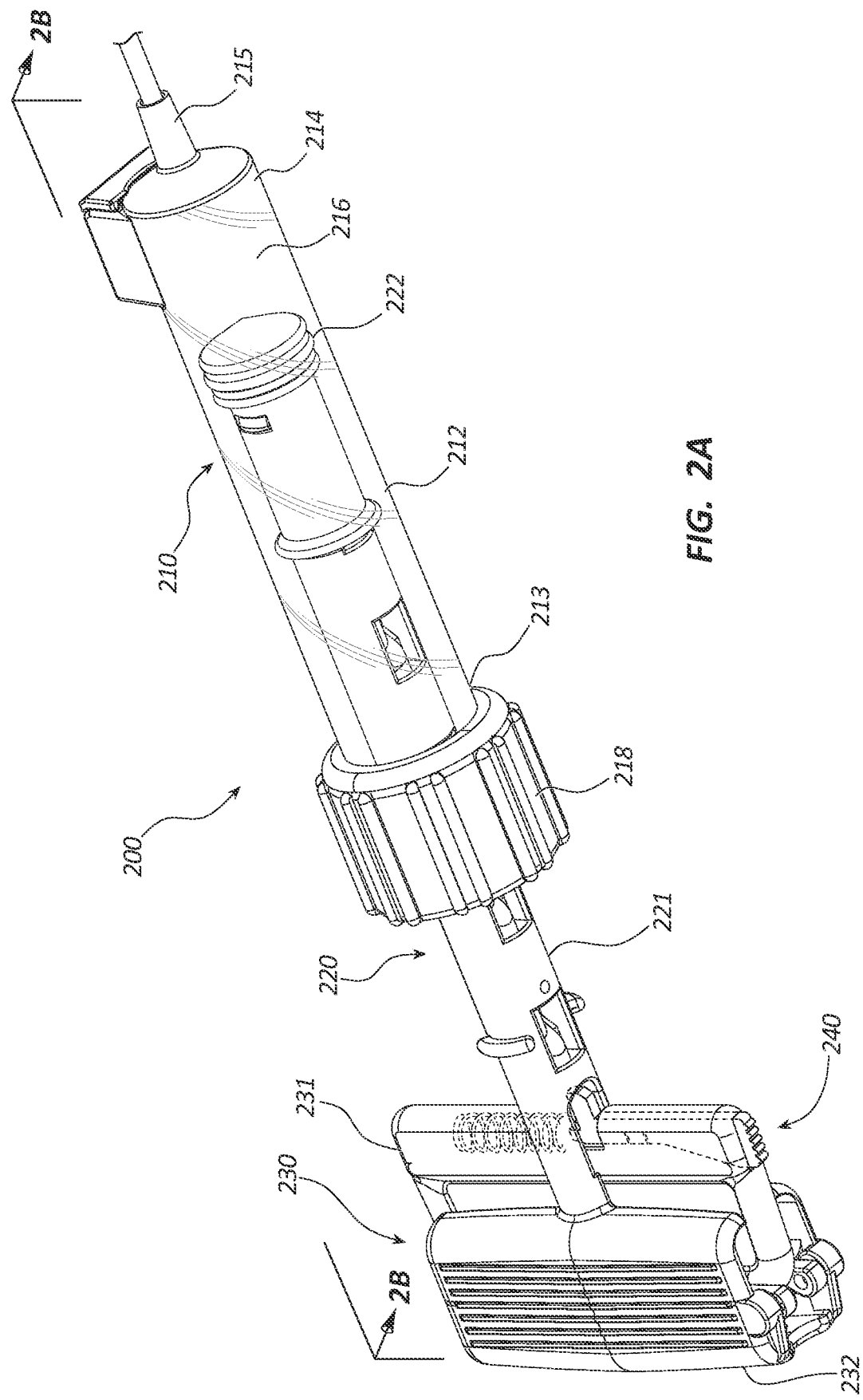
FIG. 2A is a perspective view of another embodiment of an inflation device with a trigger locking member.
Figure 2B:
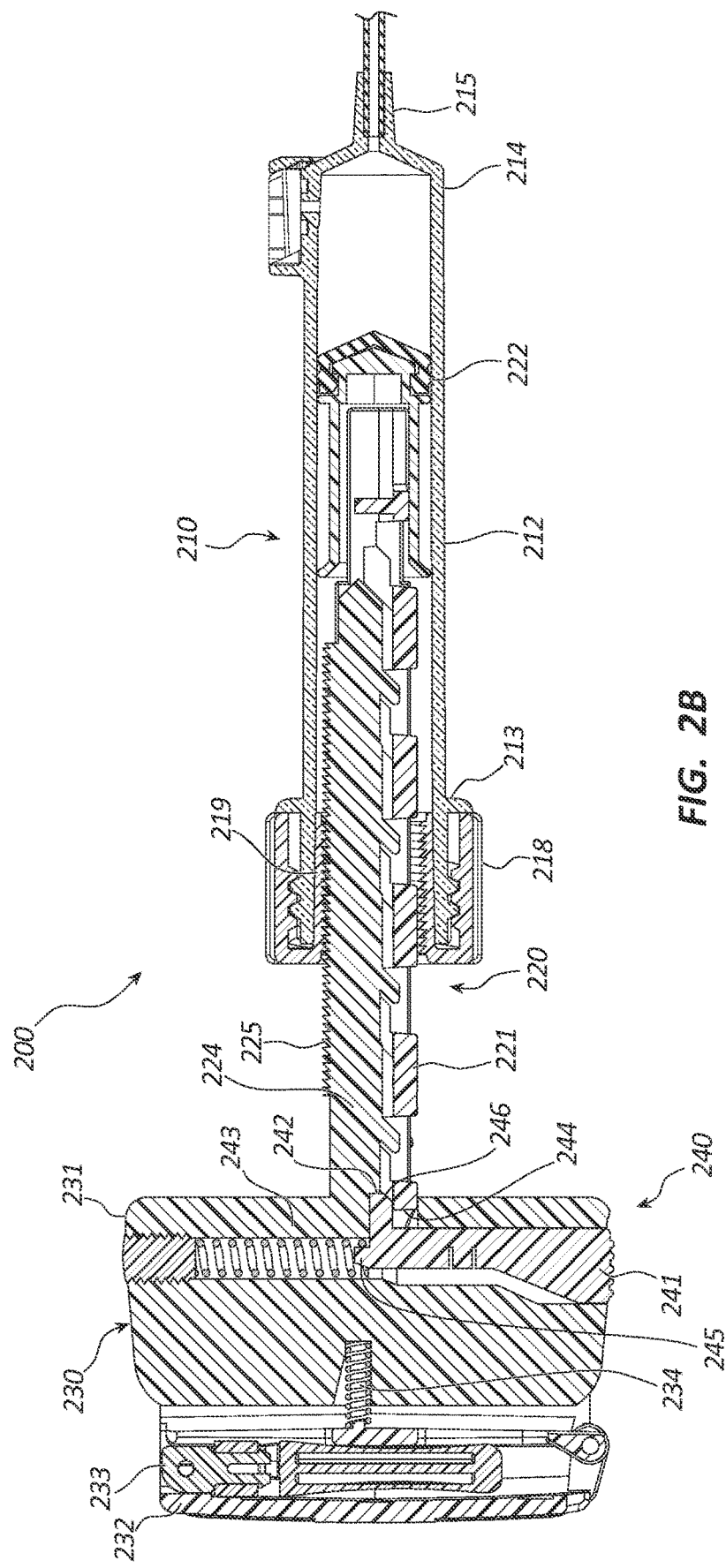
FIG. 2B is a cross-sectional view, taken through plane 2B-2B of FIG. 2A, of the inflation device of FIG. 2A in a pressurization state.
Figure 2C:
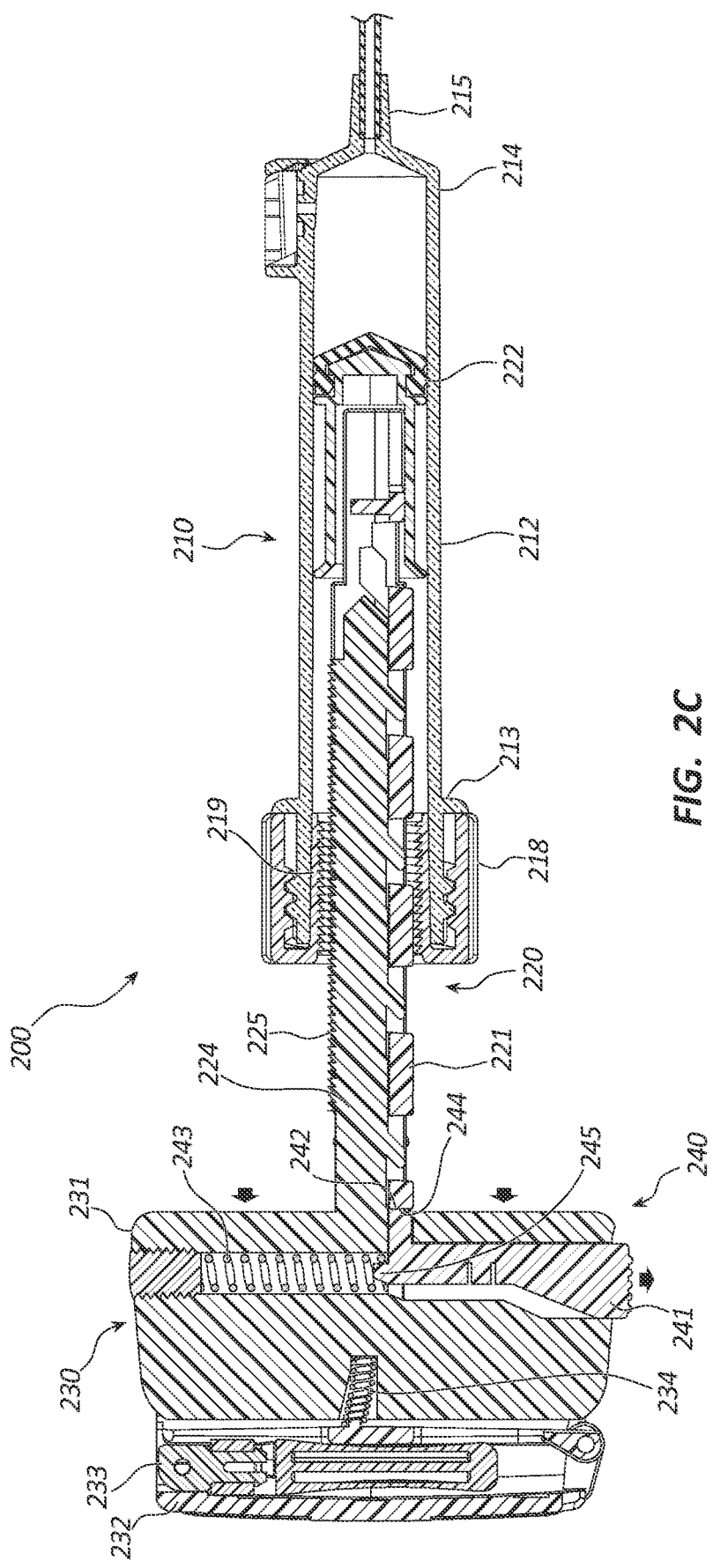
FIG. 2C is a cross-sectional view, taken through plane 2B-2B of FIG. 2A, of the inflation device of FIG. 2A in a priming state.

FIGS. 2A-2C depict an embodiment of an inflation device 200 that resembles the inflation device 100 described above in certain respects. Accordingly, like features are designated with like reference numerals, with the leading digit incremented to "2." For example, the embodiment depicted in FIG. 2A includes a trigger locking member 240 that may, in some respects, resemble the trigger locking member 140 of FIG. 1A. Relevant disclosure set forth above regarding similarly identified features thus may not be repeated hereafter. Moreover, specific features of the inflation device 100 and related components shown in FIGS. 1A-1C may not be shown or identified by a reference numeral in the drawings or specifically discussed in the written description that follows. However, such features may clearly be the same, or substantially the same, as features depicted in other embodiments and/or described with respect to such embodiments. Accordingly, the relevant descriptions of such features apply equally to the features of the inflation device 200 and related components depicted in FIGS. 2A-2C. Any suitable combination of the features, and variations of the same, described with respect to the inflation device 100 and related components illustrated in FIGS. 1A-1C can be employed with the inflation device 200 and related components of FIGS. 2A-2C, and vice versa. This pattern of disclosure applies equally to further embodiments depicted in subsequent figures and described hereafter, wherein the leading digits may be further incremented.

FIGS. 2A-2C depict another embodiment of an inflation device 200. In the illustrated embodiment, the inflation device 200 is partially comprised of a syringe 210. The inflation device 200 includes three broad groups of components; each group may have numerous subcomponents and parts. The three broad component groups are: a body component such as syringe body 212, a pressurization component such as plunger 220, and a handle 230.

The syringe body 212 may be formed of a generally cylindrical hollow tube configured to receive the plunger 220. The syringe body 212 may include an inlet/outlet port 215 located adjacent the distal end 214 of the syringe body 212. In some embodiments, a coupling member 218 may be coupled to the syringe body 212 adjacent the proximal end 213 of the syringe body 212. The coupling member 218 may include a center aperture configured to allow the plunger 220 to pass through the coupling member 218 into the syringe body 212. Further, the coupling member 218 may include coupling member threads 219 configured to selectively couple the coupling member 218 to the plunger 220. For example, the coupling member 218 may comprise a polymeric nut at the proximal end 213 of the syringe body 212.

The plunger 220 may be configured to be longitudinally displaceable within the syringe body 212. The plunger 220 may be comprised of a plunger shaft 221 coupled to a plunger seal 222 at the distal end of the plunger shaft 221. The plunger shaft 221 may also be coupled to the handle 230 at the proximal end of the plunger shaft 221, with the plunger shaft 221 spanning the distance between the plunger seal 222 and the handle 230. Additionally, the coupling member 218 may engage rail threads 225 configured to couple the plunger 220 to the coupling member 218. The rail threads 225 may be configured such that they may be retracted within the plunger shaft 221. In some embodiments, the rail threads 225 do not extend 360 degrees around the axis of the plunger shaft 221. For example, the rail threads 225 may be formed on a thread rail 224 on the plunger shaft 221. The thread rail 224 may be retracted from the coupling member threads 219 by actuating a mechanism such as a trigger 231.

The handle 230 broadly refers to the group of components coupled to the proximal end of the plunger 220, some of which may be configured to be graspable by a user. In certain embodiments, the handle 230 may be configured such that the user may manipulate the position of the plunger 220 by manipulating the handle 230. Further, in some embodiments, the handle 230 may be an actuator mechanism configured to manipulate components of the inflation device 200.

As illustrated in FIGS. 2A-2C, the handle 230 includes a grip portion 232 and a trigger 231. The grip portion 232 may be configured to be gripped by a hand of a user. While gripping, the user may either rotate the handle 230 or longitudinally displace the handle 230 to inflate or deflate a medical device in fluid communication with the syringe 210. A crank member 233 may be selectively disposed within the grip portion 232. The crank member 233 may be configured to be selectively extended laterally from the grip portion 232 to provide rotational leverage when the handle 230 is rotated. The plunger shaft 221 extends distally from the grip portion 232. The plunger shaft 221 may be fixedly coupled to the grip portion 232.

In the illustrated embodiment, the trigger 231 may be operatively coupled to the grip portion 232. The trigger 231 is shown to extend distally from the grip portion 232. The trigger 231 may be configured to be longitudinally displaced relative to the grip portion 232. The thread rail 224 extends distally from the trigger 231 and may be fixedly coupled to the trigger 231. The trigger 231 may be configured to be gripped with fingers of the user to displace the trigger 231 and the thread rail 224 proximally to a priming state when a proximally directed force is applied by the fingers. When displaced proximally, the rail threads 225 disengage from the coupling member threads 219 to allow the plunger 120 to be longitudinally translated in response to externally applied longitudinal forces.

As shown, the trigger 231 includes a trigger locking member 240. The locking member 240 may be configured to maintain the trigger 231 and the thread rail 224 in the priming state without continued application of the proximally directed force on the trigger 231.

As shown in FIGS. 2B-2C the locking member 240 of the illustrated embodiment an elongate pin 241, a latch member 242, and a compliant member 243. The pin 241 may be disposed within a closed channel within the grip 231 with the latch member 242 disposed within the plunger shaft 221 prior to actuation. The pin 241 may have any suitable shaped cross-section. For example, as illustrated, an outward portion of the pin 241 is larger than an inward portion of the pin 241. The pin 241 may be formed from any suitable semi-rigid or rigid polymeric material, such as styrene, polycarbonate, polyoxymethylene, acrylonitrile butadiene styrene, nylon, etc. In the illustrated embodiment, the latch member 242 is disposed adjacent an inward end of the pin 241. A portion of the latch member 242 extends distally from an outer edge of the pin 241. The latch member 142 may be configured to engage with a shoulder member 244 of the plunger shaft 221 to lock the plunger shaft 221 in the priming state. The compliant member 243 is disposed within a closed channel in axial alignment with the pin 241. The compliant member 243 may be a coiled spring or any other suitable compliant material. A protrusion 245 may extend from the pin 241 to engage with the compliant member 243 such that the compliant member 243 maintains axial alignment with the pin 241.

FIG. 2B depicts the inflation device 200 in a pressurization state where the rail threads 225 are engaged with the coupling nut threads 219, the trigger 231 is in a distal position, and the locking member 240 is not actuated. The pin 241 is radially inwardly displaced, the latch member 242 is disposed within an interior channel of the plunger shaft 221, and the compliant member 243 is compressed. In use, the locking member 240 is actuated when the user grips the handle 230 and applies a proximally directed finger force to the trigger 231 to displace the trigger 231 proximally. Proximal displacement of the trigger 231 radially retracts the thread rail 224 to disengage the rail threads 225 from the coupling nut threads 219 and configure the inflation device 200 in the priming state. As shown in FIG. 2C, when the trigger 231 is displaced proximally, the pin 241 and latch member 242 are displaced proximally such that the latch member 242 aligns with the shoulder member 244. The resilient member 243 applies a radially outward directed force to the pin 241 such that the latch member 242 engages with the shoulder member 244 to lock the thread rail 224 in a retracted state. An outward portion of the pin 241 extends outside of the trigger 231. In other words, the trigger 231 is prevented from distal displacement when locked in the priming state. The engagement of the latch member 242 with the shoulder member 244 is maintained by friction between the latch member 242 and the shoulder member 244 when a distally directed force is applied to the trigger 231 by a trigger compliant member 234. The trigger compliant member 234 is compressed when the trigger 231 is displaced proximally. In some embodiments, the latch member 242 may include a lip to help maintain engagement with the shoulder member 244. The user may then longitudinally translate the plunger 220 to prime or deflate the inflatable medical device in fluid communication with the inflation device 200 without maintaining the proximally directed finger force on the trigger.

When desired, the locking member 240 may be de-actuated by applying an inwardly directed force to the outward end of the pin 241. The distally directed force applied to the latch member 242 and the shoulder member 244 may be relieved and the trigger compliant member 234 may apply a distally directed force to the trigger 231 to displace the thread rail 224 distally and outwardly such that the rail threads 225 engage with the coupling nut threads 219.

Figure 3A:
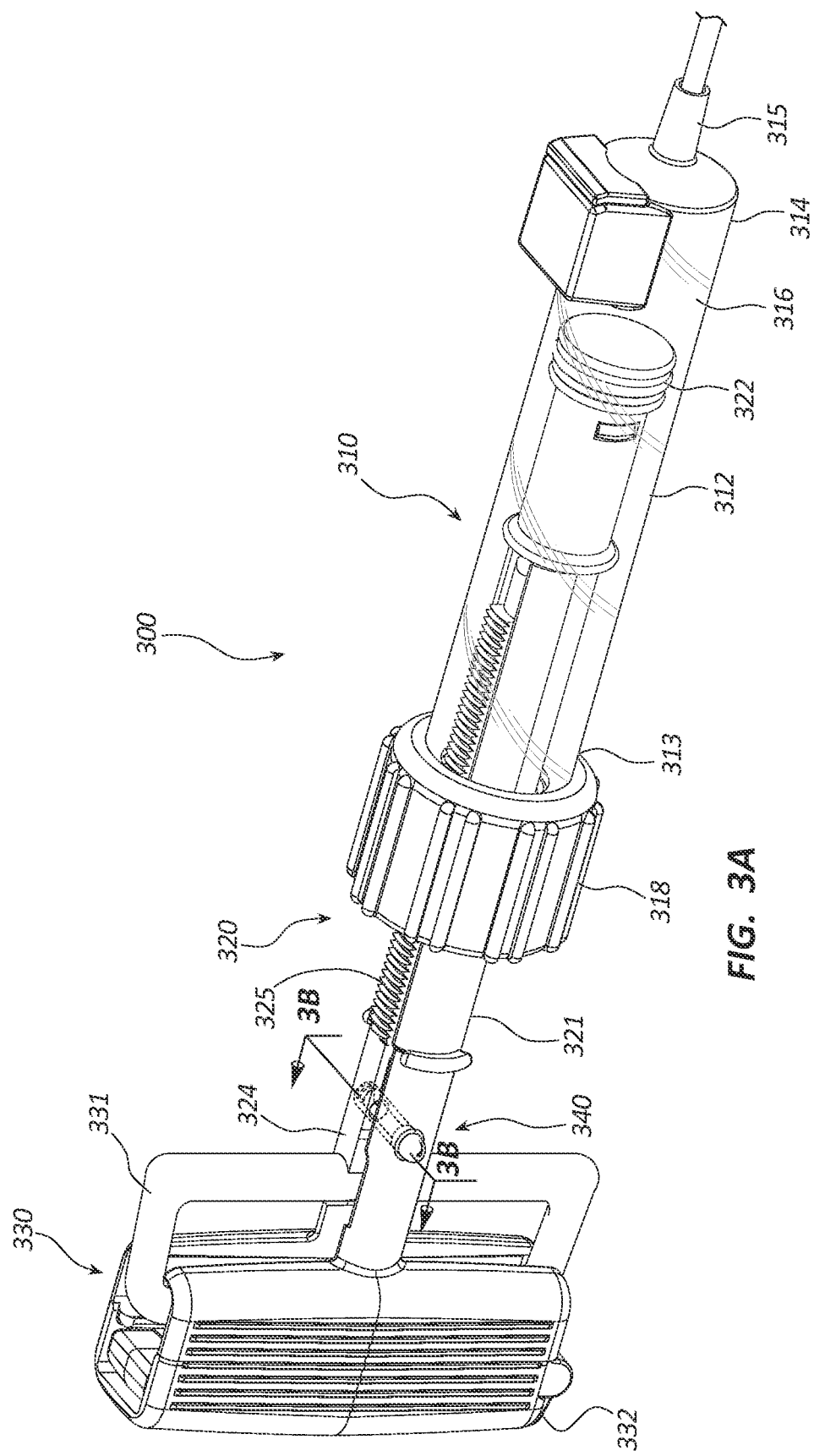
FIG. 3A is a perspective view of another embodiment of an inflation device with a trigger locking member.

FIGS. 3A-3C depict another embodiment of an inflation device 300. In the illustrated embodiment, the inflation device 300 is partially comprised of a syringe 310. The inflation device 300 includes three broad groups of components; each group may have numerous subcomponents and parts. The three broad component groups are: a body component such as syringe body 312, a pressurization component such as plunger 320, and a handle 330.

The syringe body 312 may be formed of a generally cylindrical hollow tube configured to receive the plunger 320. The syringe body 312 may include an inlet/outlet port 315 located adjacent the distal end 314 of the syringe body 312. In some embodiments, a coupling member 318 may be coupled to the syringe body 312 adjacent the proximal end 313 of the syringe body 312. The coupling member 318 may include a center aperture configured to allow the plunger 320 to pass through the coupling member 318 into the syringe body 312. Further, the coupling member 318 may include coupling member threads 319 configured to selectively couple the coupling member 318 to the plunger 320. For example, the coupling member 318 may comprise a polymeric nut at the proximal end 313 of the syringe body 312.

The plunger 320 may be configured to be longitudinally displaceable within the syringe body 312. The plunger 320 may be comprised of a plunger shaft 321 coupled to a plunger seal 322 at the distal end of the plunger shaft 321. The plunger shaft 321 may also be coupled to the handle 330 at the proximal end of the plunger shaft 321, with the plunger shaft 321 spanning the distance between the plunger seal 322 and the handle 330. Additionally, the coupling member 318 may engage rail threads 325 configured to couple the plunger 320 to the coupling member 318. The rail threads 325 may be configured such that they may be retracted within the plunger shaft 321. In some embodiments, the rail threads 325 do not extend 360 degrees around the axis of the plunger shaft 321. For example, the rail threads 325 may be formed on a thread rail 324 on the plunger shaft 321. The thread rail 324 may be retracted from the coupling member threads 319 by actuating a mechanism such as a trigger 331.

The handle 330 broadly refers to the group of components coupled to the proximal end of the plunger 320, some of which may be configured to be graspable by a user. In certain embodiments, the handle 330 may be configured such that the user may manipulate the position of the plunger 320 by manipulating the handle 330. Further, in some embodiments, the handle 330 may be an actuator mechanism configured to manipulate components of the inflation device 300.

As illustrated in FIGS. 3A-3C, the handle 330 includes a grip portion 332 and a trigger 331. The grip portion 332 may be configured to be gripped by a hand of a user. While gripping, the user may either rotate the handle 330 or longitudinally displace the handle 330 to inflate or deflate a medical device in fluid communication with the syringe 310. A crank member 333 may be selectively disposed within the grip portion 332. The crank member 333 may be configured to be selectively extended laterally from the grip portion 332 to provide rotational leverage when the handle 330 is rotated. The plunger shaft 321 extends distally from the grip portion 332. The plunger shaft 321 may be fixedly coupled to the grip portion 332.

As depicted in FIGS. 3A-3C, the trigger 331 is operatively coupled to the grip portion 332. The trigger 331 is shown to extend distally from the grip portion 332. The trigger 331 may be configured to be longitudinally displaceable relative to the grip portion 332. The thread rail 324 extends distally from the trigger 331 and is fixedly coupled to the trigger 331. The trigger 331 may be configured to be gripped with fingers of the user to displace the trigger 331 and the thread rail 324 proximally to a priming state when a proximally directed force is applied by the fingers. When displaced proximally, the rail threads 325 disengage from the coupling member threads 319 to allow the plunger 320 to be longitudinally translated in response to externally applied longitudinal forces.

As shown, the plunger shaft 321 includes a trigger locking member 340. The locking member 340 may be configured to maintain the trigger 331 and the thread rail 224 in the priming state without continued application of the proximally directed force on the trigger 331.

As shown in FIGS. 3B-3C the locking member 340 of the illustrated embodiment comprises an elongate pin 341, a latch member 342, and a compliant member 343. The pin 341 is disposed within a closed channel within the plunger shaft 321 with the latch member 342 disposed within the closed channel prior to actuation. The pin 341 may have any suitable shaped cross-section. For example, as illustrated, the pin 341 has a circular cross-section. The pin 341 may be formed from any suitable semi-rigid or rigid polymeric material, such as styrene, polycarbonate, polyoxymethylene, acrylonitrile butadiene styrene, nylon, etc. In the illustrated embodiment, the latch member 342 is disposed adjacent an inward end of the pin 341. A portion of the latch member 342 extends proximally from a perimeter of the pin 341. A chamfer or radius may be disposed between the pin 341 and the proximally extending portion of the latch member 342 to facilitate engagement of the latch member 342 with a shoulder member 344. The latch member 342 may be configured to engage with the shoulder member 344 of the thread rail 324 to lock the trigger 331 in the priming state. The shoulder member 344 may be formed by a passage through the thread rail 324. The compliant member 343 is disposed within a closed channel in axial alignment with the pin 341. The compliant member 343 may be a coiled spring or any other suitable compliant material.

FIG. 3B depicts the inflation device 300 in a pressurization state where the rail threads 325 (not shown) are engaged with the coupling nut threads 319, the trigger 331 is in a distal position, and the locking member 340 is not actuated. The pin 341 is radially inwardly displaced, the latch member 342 is disposed within the closed channel of the plunger shaft 321, and the compliant member 343 is compressed. In use, the locking member 340 is actuated when the user grips the handle 330 and applies a proximally directed finger force to the trigger 331 to displace the trigger 331 proximally. Proximal displacement of the trigger 331 radially retracts the thread rail 324 to disengage the rail threads 325 (not shown) from the coupling nut threads 319 and configure the inflation device 300 in the priming state. FIG. 2C depicts the inflation device 300 in the priming state. As shown in FIG. 2C, when the trigger 331 is displaced proximally, the thread rail 324 is also displaced proximally causing the shoulder member 344 to align with the latch member 342. The resilient member 343 applies an outwardly directed force to the pin 341 such that the latch member 342 engages with the shoulder member 344 to lock the thread rail 324 in a retracted state and an outward portion of the pin 341 extends outside of the plunger shaft 321. In other words, the trigger 331 is prevented from distal displacement when locked in the priming state. The engagement of the latch member 342 with the shoulder member 344 is maintained by friction between the latch member 342 and the shoulder member 344 when a distally directed force is applied to the trigger 331 by a trigger compliant member 334. The trigger compliant member 334 is compressed when the trigger 331 is displaced proximally. In some embodiments, the latch member 342 may include a lip to help maintain engagement with the shoulder member 344. The user may then longitudinally translate the plunger 320 to prime or deflate the inflatable medical device in fluid communication with the inflation device 300 without maintaining the proximally directed finger force on the trigger.

When desired, the locking member 340 may be deactuated by applying an inwardly directed force to the outward end of the pin 341. The distally directed force applied to the latch member 342 and the shoulder member 344 is relieved and the trigger compliant member 334 applies a distally directed force to the trigger 331 to displace the thread rail 324 distally and radially outward such that the thread rail threads 325 (not shown) engage with the coupling nut threads 319.

Figure 4A:
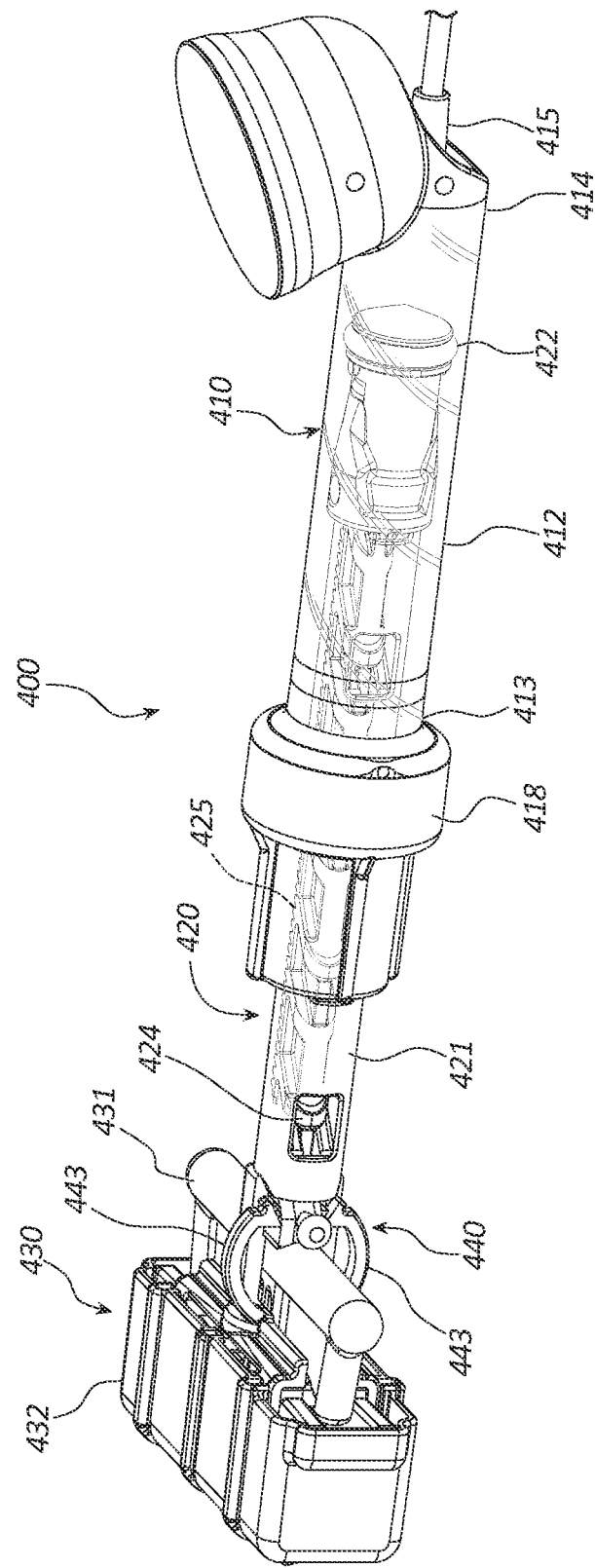
FIG. 4A is a perspective view of another embodiment of an inflation device with a trigger locking member.

FIGS. 4A-4C depict another embodiment of an inflation device 400. In the illustrated embodiment, the inflation device 400 is partially comprised of a syringe 410. The inflation device 400 includes three broad groups of components; each group may have numerous subcomponents and parts. The three broad component groups are: a body component such as syringe body 412, a pressurization component such as plunger 420, and a handle 430.

The syringe body 412 may be formed of a generally cylindrical hollow tube configured to receive the plunger 420. The syringe body 412 may include an inlet/outlet port 415 located adjacent the distal end 414 of the syringe body 412. In some embodiments, a coupling member 418 may be coupled to the syringe body 412 adjacent the proximal end 413 of the syringe body 412. The coupling member 418 may include a center aperture configured to allow the plunger 420 to pass through the coupling member 418 into the syringe body 412. Further, the coupling member 418 may include coupling member threads (not shown) configured to selectively couple the coupling member 418 to the plunger 420. For example, the coupling member 418 may comprise a polymeric nut at the proximal end 413 of the syringe body 412.

The plunger 420 may be configured to be longitudinally displaceable within the syringe body 412. The plunger 420 may be comprised of a plunger shaft 421 coupled to a plunger seal 422 at the distal end of the plunger shaft 421. The plunger shaft 421 may also be coupled to the handle 430 at the proximal end of the plunger shaft 421, with the plunger shaft 421 spanning the distance between the plunger seal 422 and the handle 430. Additionally, the coupling member 418 may engage rail threads 425 configured to couple the plunger 420 to the coupling member 418. The rail threads 425 may be configured such that they may be retracted within the plunger shaft 421. In some embodiments, the rail threads 425 do not extend 360 degrees around the axis of the plunger shaft 421. For example, the rail threads 425 may be formed on a thread rail 424 on the plunger shaft 421. The thread rail 424 may be retracted from the coupling member threads (not shown) by actuating a mechanism such as a trigger 431.

The handle 430 broadly refers to the group of components coupled to the proximal end of the plunger 420, some of which may be configured to be graspable by a user. In certain embodiments, the handle 430 may be configured such that the user may manipulate the position of the plunger 420 by manipulating the handle 430. Further, in some embodiments, the handle 430 may be an actuator mechanism configured to manipulate components of the inflation device 400.

As illustrated in FIGS. 4A-4C, the handle 430 includes a grip portion 432 and a trigger 431. The grip portion 432 may be configured to be gripped by a hand of a user. While gripping, the user may either rotate the handle 430 or longitudinally displace the handle 430 to inflate or deflate a medical device in fluid communication with the syringe 410. The plunger shaft 421 extends distally from the grip portion 432. The plunger shaft 421 may be fixedly coupled to the grip portion 432.

As depicted in FIGS. 4A-4C, the trigger 431 may be operatively coupled to the grip portion 432. The trigger 431 is shown to extend distally from the grip portion 432. The trigger 431 may be configured to be longitudinally displaceable relative to the grip portion 432. The thread rail 424 extends distally from the trigger 431 and is fixedly coupled to the trigger 431. The trigger 431 may be configured to be gripped with fingers of the user to displace the trigger 431 and the thread rail 424 proximally to a priming state when a proximally directed force is applied by the fingers. When displaced proximally, the thread rail threads 425 disengage from the coupling member threads 419 to allow the plunger 420 to be longitudinally translated in response to externally applied longitudinal forces.

As shown, the plunger shaft 421 includes a trigger locking member 440. The locking member 440 may be configured to maintain the trigger 431 and the thread rail 424 in the priming state without continued application of the proximally directed force on the trigger 431.

FIGS. 4B-4C depict the locking member 440 including an elongate pin 441, a latch member 442, a shoulder member 444, and a compliant member 443. The pin 441 is disposed within a closed channel within the thread rail 424. The pin 441 includes a head 446 disposed at an outer end of the pin 441. As illustrated, the latch member 442 is disposed adjacent a distal end of the compliant member 443. The latch member 442 may include a proximally facing surface 447 that is oriented perpendicular to a longitudinal axis of the thread rail 424. The shoulder member 444 may be disposed on an outer surface of the thread rail 424 and comprise a distally facing surface 448 that is oriented perpendicular to the longitudinal axis of the thread rail 424. The shoulder member 444 may include an inclined or radiused proximally facing surface. The latch member 442 may be configured to engage with the shoulder member 444 to lock the trigger 431 in the priming state. The compliant member 443 may be configured as a leaf spring with a proximal end coupled to the plunger shaft 421. Other suitable configurations of the resilient member 443 are within the scope of this disclosure. As depicted in FIGS. 4A-4C, the inflatable device 400 comprises a pair of locking members 440 disposed on opposite sides of the plunger 420. In other embodiments, the inflatable device 400 may include a single locking member 440.

FIG. 4B depicts the inflation device 400 in a pressurization state where the rail threads 425 are engaged with the coupling nut threads 419, the trigger 431 is in a distal position, and the locking member 440 is unactuated. The pin 441 is radially outwardly displaced, the latch member 442 is disposed proximal to the shoulder member 444, and the shoulder member 444 is in axial alignment with the latch member 442. In use, the locking member 440 is actuated when the user grips the handle 430 and applies a proximally directed finger force to the trigger 431 to displace the trigger 431 proximally. Proximal displacement of the trigger 431 radially retracts the thread rail 424 to disengage the rail threads 425 from the coupling nut threads 419 and configure the inflation device 400 in the priming state.

FIG. 4C shows the inflation device 400 in the priming state. As shown in FIG. 4C, when the trigger 431 is displaced proximally, the thread rail 424 is also displaced proximally causing the shoulder member 444 to be displaced proximally. The latch member 442 is displaced outwardly by the shoulder member 440. The resilient member 443 is outwardly displaced until the proximally facing surface 447 reaches the distally facing surface 448 of the shoulder member 444. The resilient member 443 applies an inwardly directed force to the latch member 442 such that the latch member 442 engages with the shoulder member 444 to lock the trigger 431 in the priming state. In other words, the trigger 431 is prevented from distal displacement when locked in the priming state. The engagement of the latch member 442 with the shoulder member 444 may be maintained by friction between the latch member 442 and the shoulder member 444 when a distally directed force is applied to the trigger 431 by a trigger compliant member 434. The trigger compliant member 434 is compressed when the trigger 431 is displaced proximally. The user may then longitudinally translate the plunger 420 to prime or deflate the inflatable medical device in fluid communication with the inflation device 400 without maintaining the proximally directed finger force on the trigger.

When desired, the locking member 440 may be deactuated by applying an inwardly directed force to the head 446 of the pin 441. The pin 441 may laterally displace the thread rail 424 such that the shoulder member 444 is not in axial alignment with the latch member 442. The thread rail 424 may be displaced distally by a distally directed force applied by the trigger compliant member 434 such that the thread rail teeth 425 engage with the coupling nut threads 419.

Figure 5A:
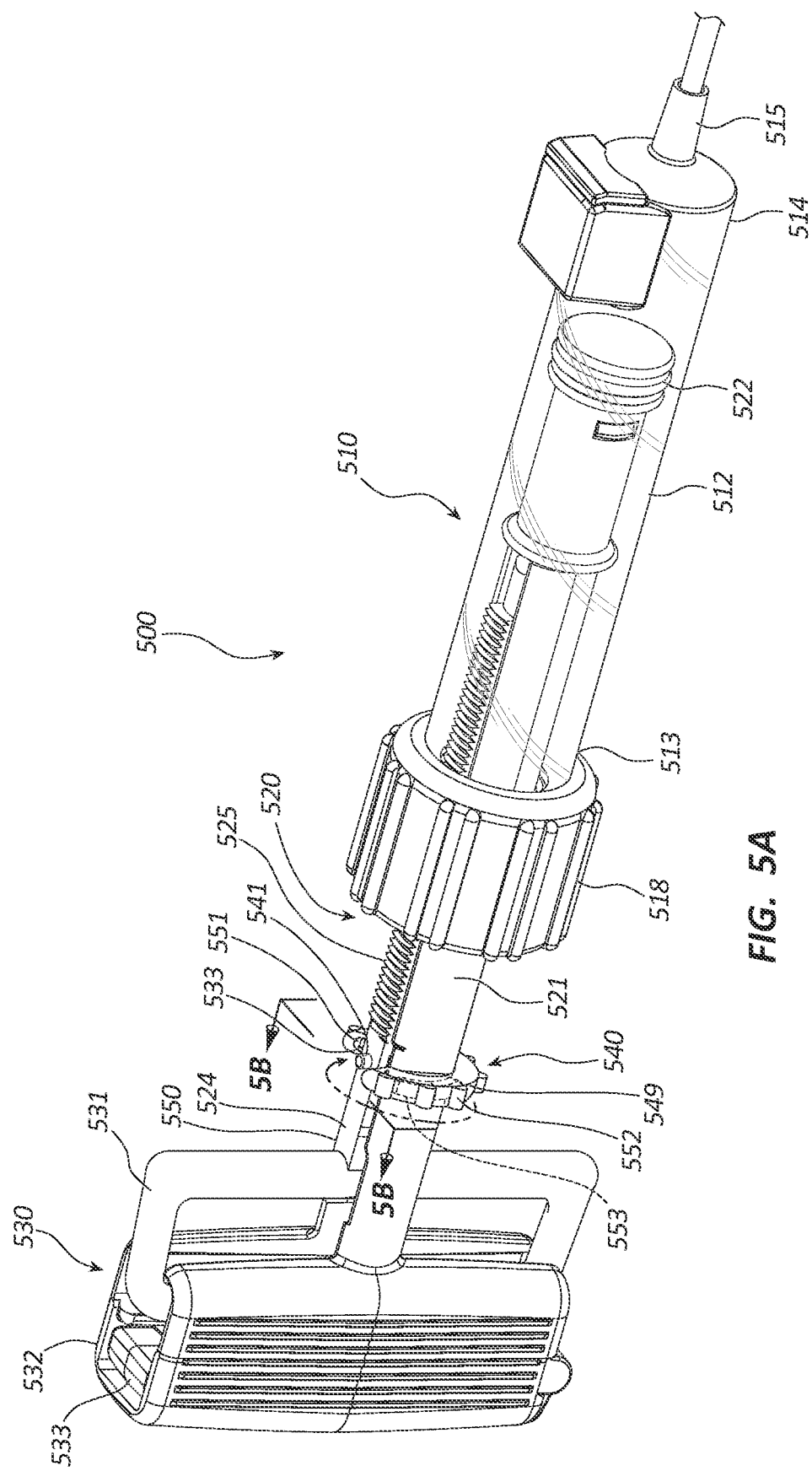
FIG. 5A is a perspective view of another embodiment of an inflation device with a trigger locking member.

FIGS. 5A-5C depict another embodiment of an inflation device 500. In the illustrated embodiment, the inflation device 500 is partially comprised of a syringe 510. The inflation device 500 includes three broad groups of components; each group may have numerous subcomponents and parts. The three broad component groups are: a body component such as syringe body 512, a pressurization component such as plunger 520, and a handle 530.

The syringe body 512 may be formed of a generally cylindrical hollow tube configured to receive the plunger 520. The syringe body 512 may include an inlet/outlet port 515 located adjacent the distal end 514 of the syringe body 512. In some embodiments, a coupling member 518 may be coupled to the syringe body 512 adjacent the proximal end 513 of the syringe body 512. The coupling member 518 may include a center aperture configured to allow the plunger 520 to pass through the coupling member 518 into the syringe body 512. Further, the coupling member 518 may include coupling member threads (not shown) configured to selectively couple the coupling member 518 to the plunger 520. For example, the coupling member 518 may comprise a polymeric nut at the proximal end 513 of the syringe body 512.

The plunger 520 may be configured to be longitudinally displaceable within the syringe body 512. The plunger 520 may be comprised of a plunger shaft 521 coupled to a plunger seal 522 at the distal end of the plunger shaft 521. The plunger shaft 521 may also be coupled to the handle 530 at the proximal end of the plunger shaft 521, with the plunger shaft 521 spanning the distance between the plunger seal 522 and the handle 530. Additionally, the coupling member 518 may engage rail threads 525 configured to couple the plunger 520 to the coupling member 518. The rail threads 525 may be configured such that they may be retracted within the plunger shaft 521. In some embodiments, the rail threads 525 do not extend 360 degrees around the axis of the plunger shaft 521. For example, the rail threads 525 may be formed on a thread rail 524 on the plunger shaft 521. The thread rail 524 may be retracted from the coupling member threads (not shown) by actuating a mechanism such as a trigger 531.

The handle 530 broadly refers to the group of components coupled to the proximal end of the plunger 520, some of which may be configured to be graspable by a user. In certain embodiments, the handle 530 may be configured such that the user may manipulate the position of the plunger 520 by manipulating the handle 530. Further, in some embodiments, the handle 530 may be an actuator mechanism configured to manipulate components of the inflation device 500.

As illustrated in FIGS. 5A-5C, the handle 530 includes a grip portion 532 and a trigger 531. The grip portion 532 may be configured to be gripped by a hand of a user. While gripping, the user may either rotate the handle 530 or longitudinally displace the handle 530 to inflate or deflate a medical device in fluid communication with the syringe 510. A crank member 533 may be selectively disposed within the grip portion 532. The crank member 533 may be configured to be selectively extended laterally from the grip portion 532 to provide rotational leverage when the handle 530 is rotated. The plunger shaft 521 extends distally from the grip portion 532. The plunger shaft 521 may be fixedly coupled to the grip portion 532.

As depicted in FIGS. 5A-5C, the trigger 531 is operatively coupled to the grip portion 532. The trigger 531 is shown to extend distally from the grip portion 532. The trigger 531 may be configured to be longitudinally displaceable relative to the grip portion 532. The thread rail 524 extends distally from the trigger 531 and is fixedly coupled to the trigger 531. The trigger 531 may be configured to be gripped with fingers of the user to displace the trigger 531 and the thread rail 524 proximally to a priming state when a proximally directed force is applied by the fingers. When displaced proximally, the thread rail threads 525 disengage from the coupling member threads 519 to allow the plunger 520 to be longitudinally translated in response to externally applied longitudinal forces.

As shown, the plunger shaft 521 includes a trigger locking member 540. The locking member 540 may be configured to maintain the trigger 531 and the thread rail 524 in the priming state without continued application of the proximally directed force on the trigger 531.

FIGS. 5B-5C depict the locking member 540 including an elongate pin 541 and a rotatable ring 549. As depicted, the pin 541 is fixedly coupled to the thread rail 524 and extends radially outward from a top surface 550 of the thread rail 524. The pin 541 is disposed proximal to the thread rail threads 525. The pin 541 may include a circular cross-section and a chamfered or radiused outward end. The rotatable ring 549 may comprise a circumferential groove 551 disposed on an inner portion and knurls or ribs 552 disposed on an outer portion. The knurls or ribs 552 may be configured to provide a gripping surface to allow the rotatable ring 549 to be rotated by a user. The rotatable ring 549 includes a gap 553 disposed between ends of the rotatable ring 549. The gap 553 may comprise a length approximately equivalent to a width of the thread rail 524. The groove 551 may be configured to be disposed over at least one rib segment 585 disposed on an outer surface of the plunger shaft 521. As illustrated in FIGS. 5B and 5C, two rib segments 585 are disposed on opposing sides of the plunger shaft 521. An inner diameter of the rotatable ring 549 may be about equivalent to or less than the diameter of the plunger shaft such that the rotatable ring 549 may be rotatably secured to the plunger shaft 521.

FIG. 5B depicts the inflation device 500 in a pressurization state where the thread rail 524 is displaced radially outward, the pin 541 is disposed within the gap 553, and the groove 551 is disposed over the rib segments 585. In use, the locking member 540 is actuated when the user grips the handle 530 and applies a proximally directed finger force to the trigger 531 to displace the trigger 531 proximally. Proximal displacement of the trigger 531 radially retracts the thread rail 524 to disengage the rail threads 525 from the coupling nut threads (not shown) and configure the inflation device 500 in the priming state.

FIG. 5C shows the inflation device 500 in the priming state. As shown in FIG. 5C, the locking member 540 may lock the thread rail 524 in the retracted position. As illustrated, the rotatable ring 549 is rotated either clockwise or counter-clockwise by the user. The rotatable ring 549 may be rotated from about 90 degrees to about 270 degrees, from about 150 degrees to about 210 degrees, and about 180 degrees. When rotated, the inner portion of the rotatable ring 549 engages with the pin 541 and prevents the pin 541 and the thread rail 524 from being displaced radially outward when the trigger 531 is released by the user, locking the thread rail 524 in the retracted position. The user may then longitudinally translate the plunger 520 to prime or deflate the inflatable medical device in fluid communication with the inflation device 500 without maintaining the proximally directed finger force on the trigger.

When desired, the locking member 540 may be de-actuated by rotation of the rotatable ring 549 such that the gap 553 is disposed over the thread rail 524 and the pin 541. The thread rail 524 is allowed to be displaced outwardly into the gap 553 by a distally directed force applied to the trigger 531 by a trigger resilient member (not shown) such that the thread rail teeth (not shown) engage with the coupling nut threads (not shown).

Figure 6A:
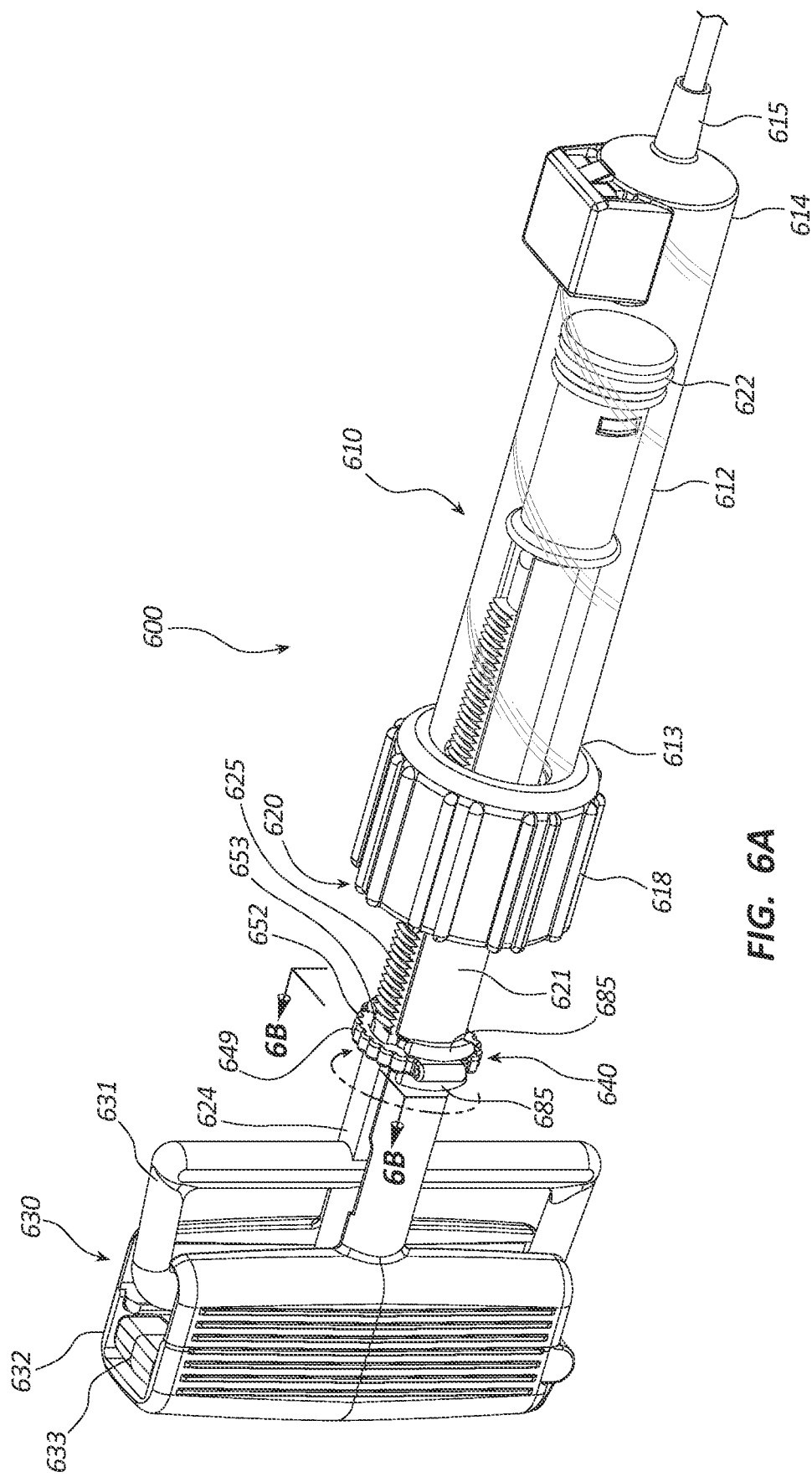
FIG. 6A is a perspective view of another embodiment of an inflation device with a trigger locking member.
Figure 6C:
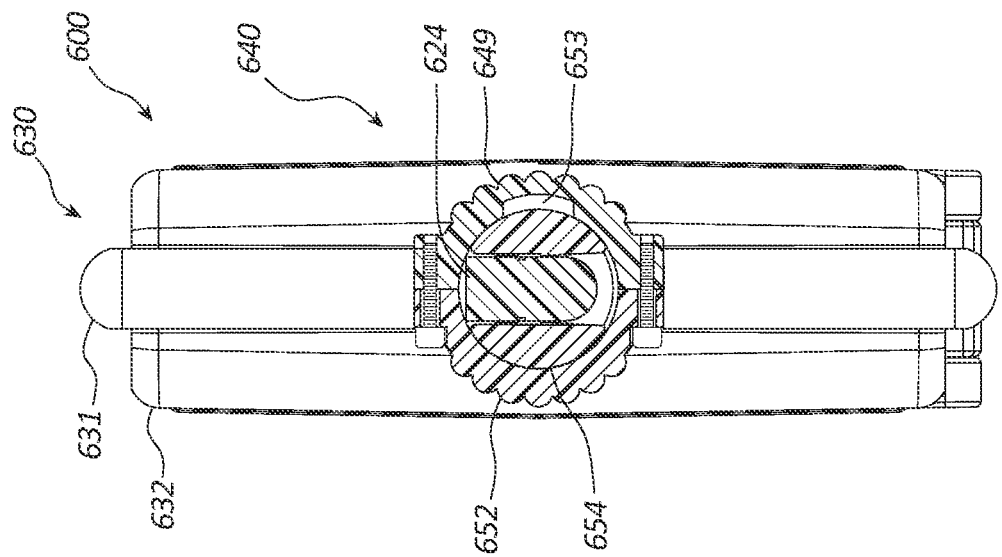
FIG. 6C is a cross-sectional view, taken through plane 6B-6B of FIG. 6A, of the inflation device of FIG. 6A in a priming state.
Figure 6B:
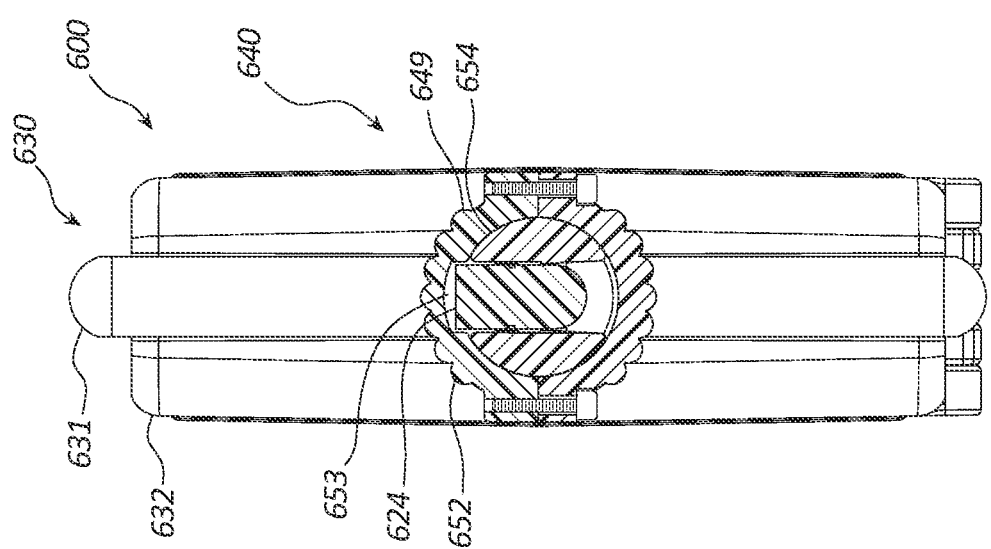
FIG. 6B is a cross-sectional view, taken through plane 6B-6B of FIG. 6A, of the inflation device of FIG. 6A in a pressurization state.

FIGS. 6A-6C depict another embodiment of an inflation device 600. In the illustrated embodiment, the inflation device 600 is partially comprised of a syringe 610. The inflation device 600 includes three broad groups of components; each group may have numerous subcomponents and parts. The three broad component groups are: a body component such as syringe body 612, a pressurization component such as plunger 620, and a handle 630.

The syringe body 612 may be formed of a generally cylindrical hollow tube configured to receive the plunger 620. The syringe body 612 may include an inlet/outlet port 615 located adjacent the distal end 614 of the syringe body 612. In some embodiments, a coupling member 618 may be coupled to the syringe body 612 adjacent the proximal end 613 of the syringe body 612. The coupling member 618 may include a center aperture configured to allow the plunger 620 to pass through the coupling member 618 into the syringe body 612. Further, the coupling member 618 may include coupling member threads (not shown) configured to selectively couple the coupling member 618 to the plunger 620. For example, the coupling member 618 may comprise a polymeric nut at the proximal end 613 of the syringe body 612.

The plunger 620 may be configured to be longitudinally displaceable within the syringe body 612. The plunger 620 may be comprised of a plunger shaft 621 coupled to a plunger seal 622 at the distal end of the plunger shaft 621. The plunger shaft 621 may also be coupled to the handle 630 at the proximal end of the plunger shaft 621, with the plunger shaft 621 spanning the distance between the plunger seal 622 and the handle 630. Additionally, the coupling member 618 may engage rail threads 625 configured to couple the plunger 620 to the coupling member 618. The rail threads 625 may be configured such that they may be retracted within the plunger shaft 621. In some embodiments, the rail threads 625 do not extend 360 degrees around the axis of the plunger shaft 621. For example, the rail threads 625 may be formed on a thread rail 624 on the plunger shaft 621. The thread rail 624 may be retracted from the coupling member threads 619 by actuating a mechanism such as a trigger 631.

The handle 630 broadly refers to the group of components coupled to the proximal end of the plunger 620, some of which may be configured to be graspable by a user. In certain embodiments, the handle 630 may be configured such that the user may manipulate the position of the plunger 620 by manipulating the handle 630. Further, in some embodiments, the handle 630 may be an actuator mechanism configured to manipulate components of the inflation device 600.

As illustrated in FIGS. 6A-6C, the handle 630 includes a grip portion 632 and a trigger 631. The grip portion 632 may be configured to be gripped by a hand of a user. While gripping, the user may either rotate the handle 630 or longitudinally displace the handle 630 to inflate or deflate a medical device in fluid communication with the syringe 610. A crank member 633 may be selectively disposed within the grip portion 632. The crank member 633 may be configured to be selectively extended laterally from the grip portion 632 to provide rotational leverage when the handle 630 is rotated. The plunger shaft 621 extends distally from the grip portion 632. The plunger shaft 621 may be fixedly coupled to the grip portion 632.

As depicted in FIGS. 6A-6C, the trigger 631 is operatively coupled to the grip portion 632. The trigger 631 is shown to extend distally from the grip portion 632. The trigger 631 may be configured to be longitudinally displaceable relative to the grip portion 632. The thread rail 624 extends distally from the trigger 631 and is fixedly coupled to the trigger 631. The trigger 631 may be configured to be gripped with fingers of the user to displace the trigger 631 and the thread rail 624 proximally to a priming state when a proximally directed force is applied by the fingers. When displaced proximally, the thread rail threads 625 disengage from the coupling member threads (not shown) to allow the plunger 620 to be longitudinally translated in response to externally applied longitudinal forces.

The plunger shaft 621 includes a trigger locking member 640. The locking member 640 may be configured to maintain the trigger 631 and the thread rail 624 in the priming state without continued application of the proximally directed force on the trigger 631.

FIGS. 6A-6C depict the locking member 640 including a rotatable ring 649. The rotatable ring 649 comprises an inner surface 654 and knurls or ribs 652 disposed on an outer portion. The knurls or ribs 652 may be configured to provide a gripping surface to allow the rotatable ring 649 to be rotated by a user. The inner surface 654 includes a gap 653 disposed between ends of the inner surface 654. The gap 653 may comprise a length approximately equivalent to a width of the thread rail 624 and a depth approximately equivalent to a height of a portion of the thread rail 624 that extends outside of the plunger shaft 621 when the inflation device is in the pressurization state. The rotatable ring 649 may be configured to be disposed between rib segments 685 disposed on an outer surface of the plunger shaft 621. The rotatable ring 649 may comprise two half rings. One half ring may comprise the gap 653. In another embodiment, each half ring may comprise the gap 685. The half rings may be coupled together to form the rotatable ring 649 by any suitable technique. For example, the half rings may be coupled by gluing, welding, bonding, fasteners, etc.

FIG. 6B depicts the inflation device 600 in the pressurization state where the thread rail 624 is displaced radially outward such that a portion of the thread rail 624 is disposed within the gap 653. In use, the locking member 640 is actuated when the user grips the handle 630 and applies a proximally directed finger force to the trigger 631 to displace the trigger 631 proximally. Proximal displacement of the trigger 631 radially retracts the thread rail 624 to disengage the rail threads 625 from the coupling nut threads 619 (not shown) and configure the inflation device 600 in the priming state. Retraction of the thread rail 624 also displaces the thread rail 624 from the gap 653 which allows the rotatable ring 649 to rotate.

FIG. 6C shows the inflation device 600 in the priming state. As shown in FIG. 6C, when actuated the locking member 640 may lock the thread rail 624 in the retracted position. As illustrated, the rotatable ring 649 is rotated either clockwise or counter-clockwise by the user. The rotatable ring 649 may be rotated from about 90 degrees to about 270 degrees, from about 150 degrees to about 210 degrees, and about 180 degrees. When rotated, the inner surface 654 of the rotatable ring 649 engages with the thread rail 624 and prevents the thread rail 624 from being displaced radially outward when the trigger 631 is released by the user, locking the thread rail 624 in the retracted position. The user may then longitudinally translate the plunger 620 to prime or deflate the inflatable medical device in fluid communication with the inflation device 600 without maintaining the proximally directed finger force on the trigger 631.

When desired, the locking member 640 may be deactuated by rotation of the rotatable ring 649 such that the gap 685 is disposed over the thread rail 624. The thread rail 624 is allowed to be displaced radially outward into the gap 685 by a distally directed force applied to the trigger 631 by a trigger resilient member (not shown) such that the thread rail teeth (not shown) engage with the coupling nut threads (not shown).

Figure 7A:
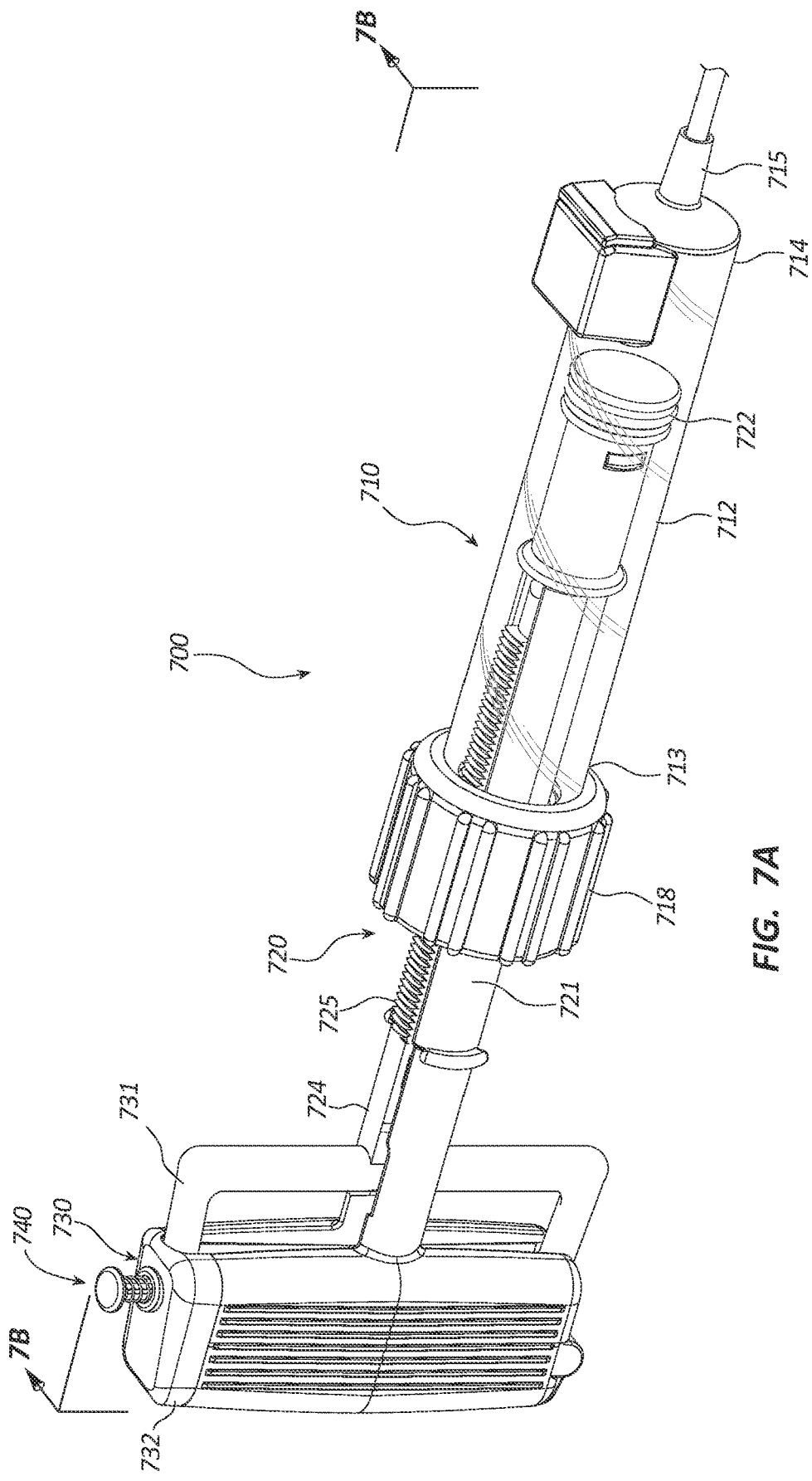
FIG. 7A is a perspective view of another embodiment of an inflation device with a trigger locking member.
Figure 7B:
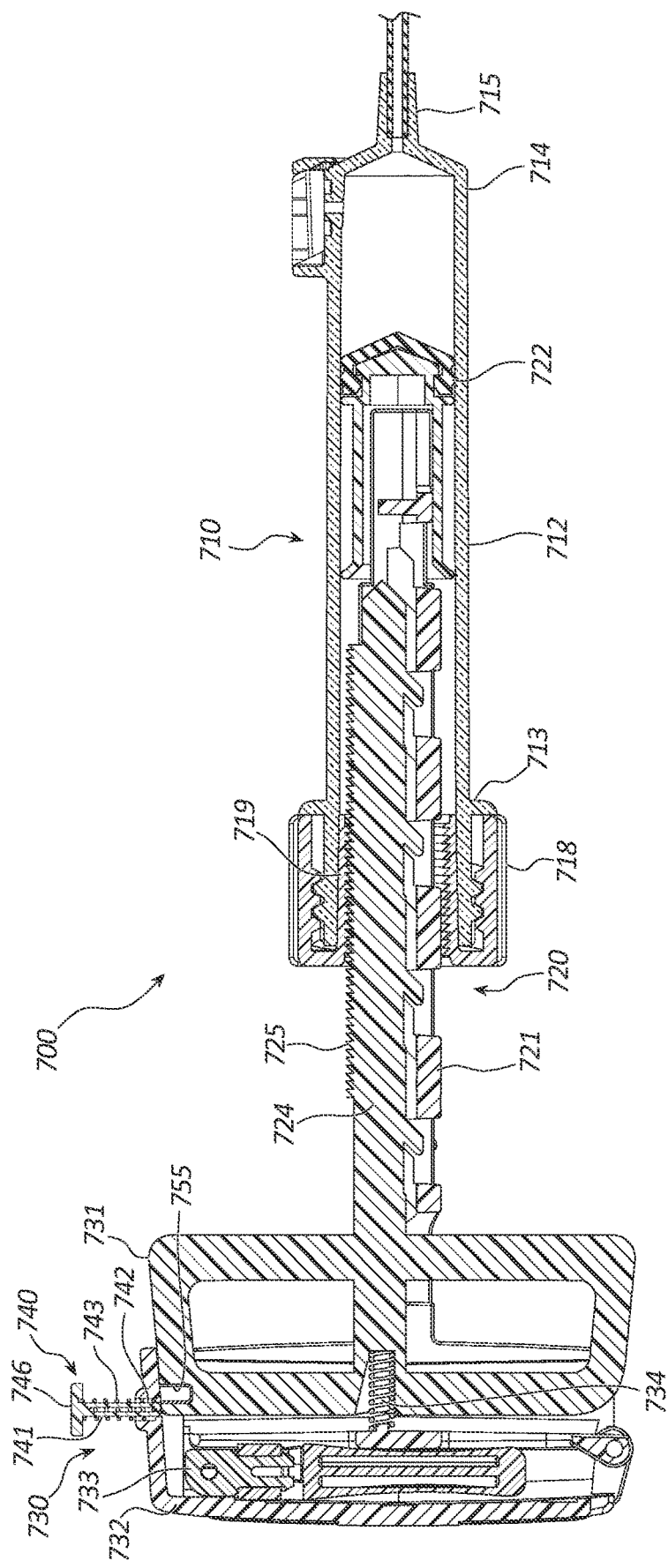
FIG. 7B is a cross-sectional view, taken through plane 7B-7B of FIG. 7A, of the inflation device of FIG. 7A in a pressurization state.
Figure 7C:
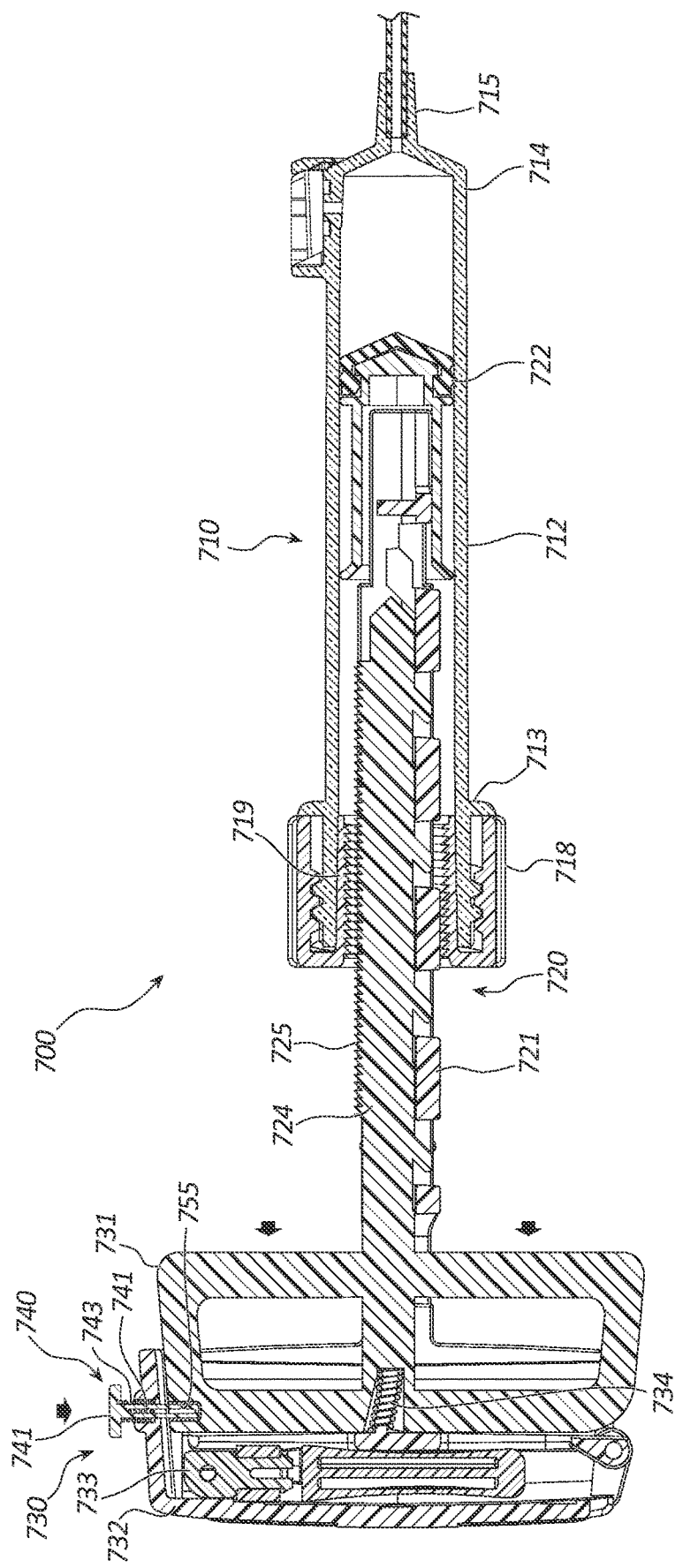
FIG. 7C is a cross-sectional view, taken through plane 7B-7B of FIG. 7A, of the inflation device of FIG. 7A in a priming state.

FIGS. 7A-7C depict another embodiment of an inflation device 700. In the illustrated embodiment, the inflation device 700 is partially comprised of a syringe 710. The inflation device 700 includes three broad groups of components; each group may have numerous subcomponents and parts. The three broad component groups are: a body component such as syringe body 712, a pressurization component such as plunger 720, and a handle 730.

The syringe body 712 may be formed of a generally cylindrical hollow tube configured to receive the plunger 720. The syringe body 712 may include an inlet/outlet port 715 located adjacent the distal end 714 of the syringe body 712. In some embodiments, a coupling member 718 may be coupled to the syringe body 712 adjacent the proximal end 713 of the syringe body 712. The coupling member 718 may include a center aperture configured to allow the plunger 720 to pass through the coupling member 718 into the syringe body 712. Further, the coupling member 718 may include coupling member threads 719 configured to selectively couple the coupling member 718 to the plunger 720. For example, the coupling member 718 may comprise a polymeric nut at the proximal end 713 of the syringe body 712.

The plunger 720 may be configured to be longitudinally displaceable within the syringe body 712. The plunger 720 may be comprised of a plunger shaft 721 coupled to a plunger seal 722 at the distal end of the plunger shaft 721. The plunger shaft 721 may also be coupled to the handle 730 at the proximal end of the plunger shaft 721, with the plunger shaft 721 spanning the distance between the plunger seal 722 and the handle 730. Additionally, the coupling member 718 may engage rail threads 725 configured to couple the plunger 720 to the coupling member 718. The rail threads 725 may be configured such that they may be retracted within the plunger shaft 721. In some embodiments, the rail threads 725 do not extend 360 degrees around the axis of the plunger shaft 721. For example, the rail threads 725 may be formed on a thread rail 724 on the plunger shaft 721. The thread rail 724 may be retracted from the coupling member threads 719 by actuating a mechanism such as a trigger 731.

The handle 730 broadly refers to the group of components coupled to the proximal end of the plunger 720, some of which may be configured to be graspable by a user. In certain embodiments, the handle 730 may be configured such that the user may manipulate the position of the plunger 720 by manipulating the handle 730. Further, in some embodiments, the handle 730 may be an actuator mechanism configured to manipulate components of the inflation device 700.

As illustrated in FIGS. 7A-7C, the handle 730 includes a grip portion 732 and a trigger 731. The grip portion 732 may be configured to be gripped by a hand of a user. While gripping, the user may either rotate the handle 730 or longitudinally displace the handle 730 to inflate or deflate a medical device in fluid communication with the syringe 710. A crank member 733 may be selectively disposed within the grip portion 732. The crank member 733 may be configured to be selectively extended laterally from the grip portion 732 to provide rotational leverage when the handle 730 is rotated. The plunger shaft 721 extends distally from the grip portion 732. The plunger shaft 721 may be fixedly coupled to the grip portion 732.

As depicted in FIGS. 7A-7C, the trigger 731 is operatively coupled to the grip portion 732. The trigger 731 is shown to extend distally from the grip portion 732. The trigger 731 may be configured to be longitudinally displaceable relative to the grip portion 732. The thread rail 724 extends distally from the trigger 731 and is fixedly coupled to the trigger 731. The trigger 731 may be configured to be gripped with fingers of the user to displace the trigger 731 and the thread rail 724 proximally to a priming state when a proximally directed force is applied by the fingers. When displaced proximally, the rail threads 725 disengage from the coupling member threads 719 to allow the plunger 720 to be longitudinally translated in response to externally applied longitudinal forces.

As shown, the handle 730 includes a trigger locking member 740. The locking member 740 may be configured to maintain the trigger 731 and the thread rail 724 in the priming state without continued application of the proximally directed force on the trigger 731.

FIGS. 7A-7C depict the locking member 740 including an elongate pin 741, a pin receiving recess and a compliant member 743. The pin 741 is partially disposed within a closed channel within the handle 730 and extends laterally from the handle 730. The pin 741 includes a head 746 disposed at an outer end. The head 746 is configured to be engaged by a user's finger to displace the pin 741 from an extended and unlocked state to a depressed and locked state. The compliant member 743 (e.g., a coiled spring) is disposed between the head 746 and a wall of the handle 730. The compliant member 743 is configured to displace the pin 741 from the depressed and locked state to the extended and unlocked state. The pin receiving recess 755 is disposed in a lateral portion of the trigger 731. The recess 755 is configured to receive a portion of the pin 741 to lock the trigger 731 in a priming state.

FIG. 7B depicts the inflation device 700 in a pressurization state where the rail threads 725 are engaged with the coupling nut threads 719, the trigger 731 is in a distal position, and the locking member 740 is de-actuated. The pin 741 is radially outwardly displaced by the compliant member 743. In use, the locking member 740 is actuated when the user grips the handle 730 and applies a proximally directed finger force to the trigger 731 to displace the trigger 731 proximally. Proximal displacement of the trigger 731 radially retracts the thread rail 724 to disengage the rail threads 725 from the coupling nut threads 719 and configure the inflation device 700 in the priming state.

FIG. 7C shows the inflation device 700 in the priming state. As shown in FIG. 7C, when the trigger 731 is displaced proximally, recess 755 is brought into alignment with the pin 741. When in alignment, the user may actuate the locking member 740 by applying an inwardly directed force to the head 746 with a finger to compress the compliant member 743 and displace a portion of the pin 741 into the recess 755. When a portion of the pin 741 is disposed within the recess 755, the trigger is locked in a proximal position and the inflation device 700 is in the priming state. In other words, the trigger 731 is prevented from distal displacement when locked in the priming state. The portion of the pin 741 is maintained disposed within the recess 755 by a frictional force between the pin 741 and a wall of the recess 755. The frictional force may be increased by a distally directed force applied to the trigger 731 by a trigger compliant member 734. The user may then longitudinally translate the plunger 720 to prime or deflate the inflatable medical device in fluid communication with the inflation device 700 without maintaining the proximally directed finger force on the trigger 731.

When desired, the locking member 740 may be de-actuated by applying the proximally directed finger force to the trigger 731. The trigger 731 may be displaced proximally to relieve the frictional force between the pin 741 and the recess 755. The compliant member 743 applies a radially outward directed force on the head 746 causing the portion of the pin 741 to be withdrawn from the recess 755. The user may release the trigger 731 and the trigger compliant member 734 may displace the trigger distally resulting in engagement of the rail threads 725 with the coupling nut threads 719 and converting the inflation device 700 to the pressurization state.

Figure 8A:
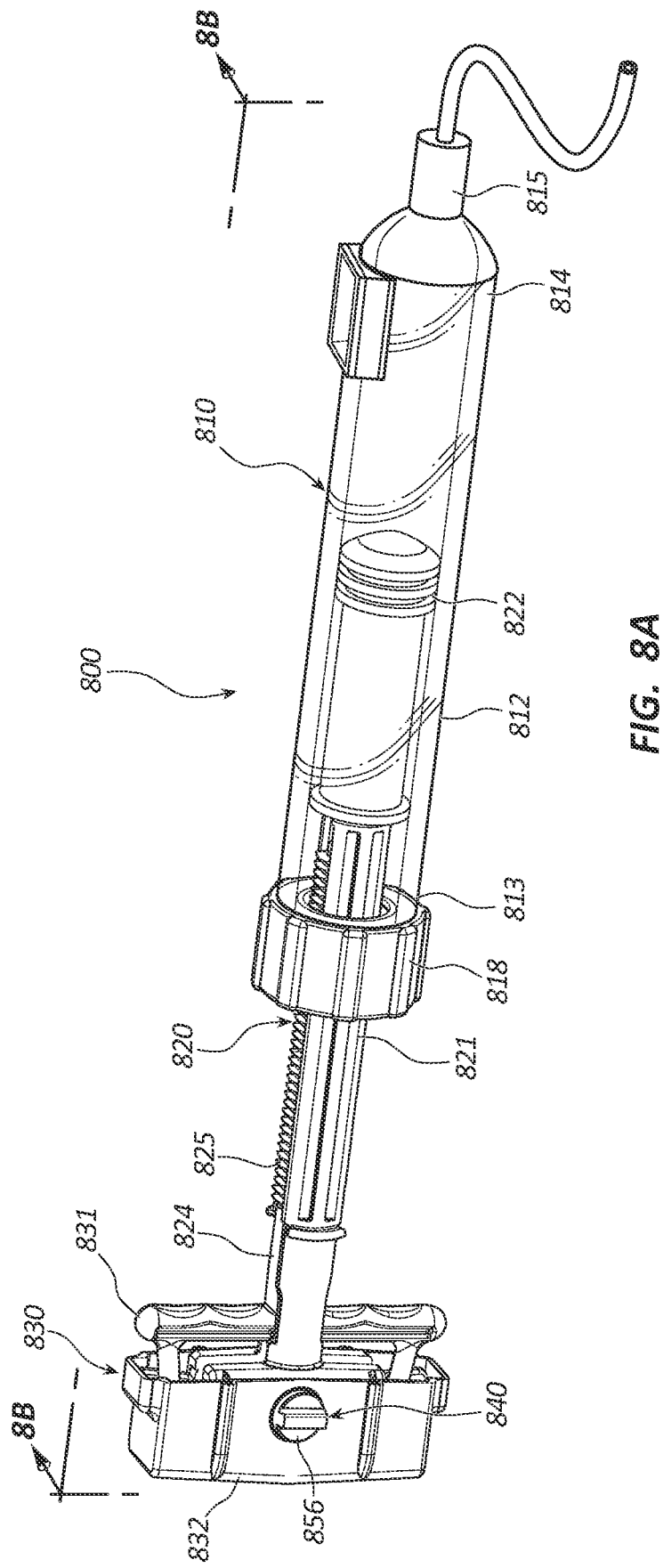
FIG. 8A is a perspective view of another embodiment of an inflation device with a trigger locking member.
Figure 8B:
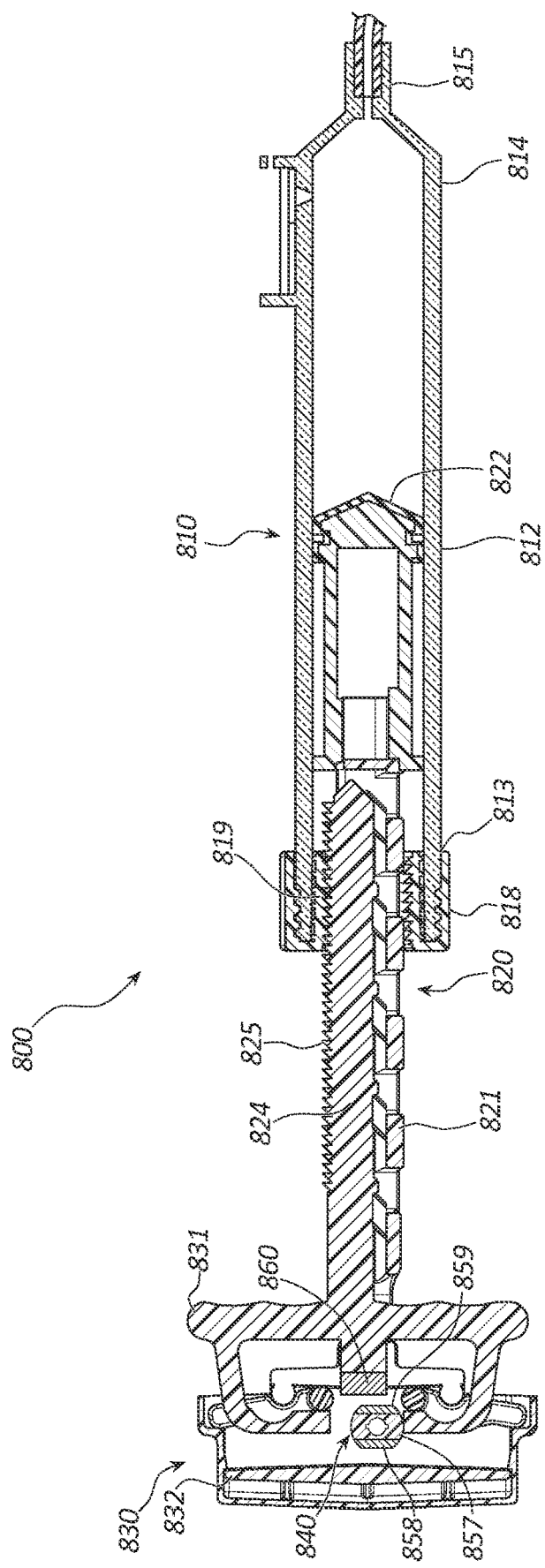
FIG. 8B is a cross-sectional view, taken through plane 8B-8B of FIG. 8A, of the inflation device of FIG. 8A in a pressurization state.
Figure 8C:
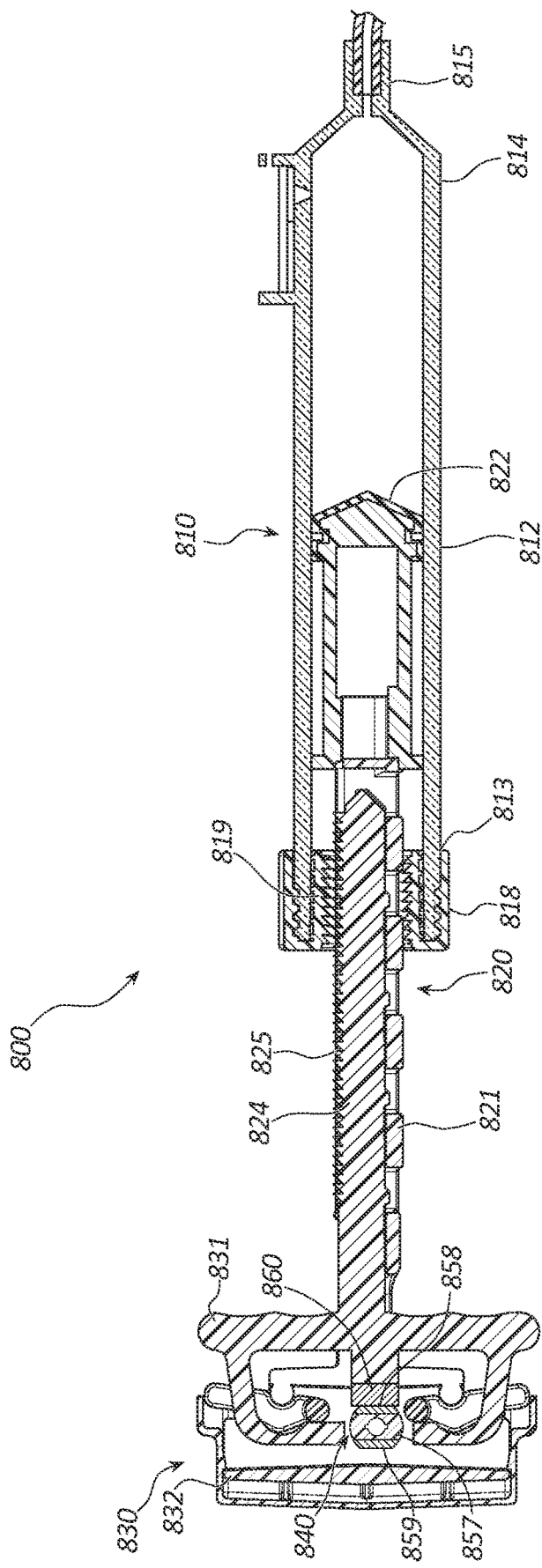
FIG. 8C is a cross-sectional view, taken through plane 8B-8B of FIG. 8A, of the inflation device of FIG. 8A in a priming state.

FIGS. 8A-8C depict another embodiment of an inflation device 800. In the illustrated embodiment, the inflation device 800 is partially comprised of a syringe 810. The inflation device 800 includes three broad groups of components; each group may have numerous subcomponents and parts. The three broad component groups are: a body component such as syringe body 812, a pressurization component such as plunger 820, and a handle 830.

The syringe body 812 may be formed of a generally cylindrical hollow tube configured to receive the plunger 820. The syringe body 812 may include an inlet/outlet port 815 located adjacent the distal end 814 of the syringe body 812. In some embodiments, a coupling member 818 may be coupled to the syringe body 812 adjacent the proximal end 813 of the syringe body 812. The coupling member 818 may include a center aperture configured to allow the plunger 820 to pass through the coupling member 818 into the syringe body 812. Further, the coupling member 818 may include coupling member threads 819 configured to selectively couple the coupling member 818 to the plunger 820. For example, the coupling member 818 may comprise a polymeric nut at the proximal end 813 of the syringe body 812.

The plunger 820 may be configured to be longitudinally displaceable within the syringe body 812. The plunger 820 may be comprised of a plunger shaft 821 coupled to a plunger seal 822 at the distal end of the plunger shaft 821. The plunger shaft 821 may also be coupled to the handle 830 at the proximal end of the plunger shaft 821, with the plunger shaft 821 spanning the distance between the plunger seal 822 and the handle 830. Additionally, the coupling member 818 may engage rail threads 825 configured to couple the plunger 820 to the coupling member 818. The rail threads 825 may be configured such that they may be retracted within the plunger shaft 821. In some embodiments, the rail threads 825 do not extend 360 degrees around the axis of the plunger shaft 821. For example, the rail threads 825 may be formed on a thread rail 824 on the plunger shaft 821. The thread rail 824 may be retracted from the coupling member threads 819 by actuating a mechanism such as a trigger 831.

The handle 830 broadly refers to the group of components coupled to the proximal end of the plunger 820, some of which may be configured to be graspable by a user. In certain embodiments, the handle 830 may be configured such that the user may manipulate the position of the plunger 820 by manipulating the handle 830. Further, in some embodiments, the handle 830 may be an actuator mechanism configured to manipulate components of the inflation device 800.

As illustrated in FIGS. 8A-8C, the handle 730 includes a grip portion 832 and a trigger 831. The grip portion 832 may be configured to be gripped by a hand of a user. While gripping, the user may either rotate the handle 830 or longitudinally displace the handle 830 to inflate or deflate a medical device in fluid communication with the syringe 810. The plunger shaft 821 extends distally from the grip portion 832. The plunger shaft 821 may be fixedly coupled to the grip portion 832.

As depicted in FIGS. 8A-8C, the trigger 831 is operatively coupled to the grip portion 832. The trigger 831 is shown to extend distally from the grip portion 832. The trigger 831 may be configured to be longitudinally displaceable relative to the grip portion 832. The thread rail 824 extends distally from the trigger 831 and is fixedly coupled to the trigger 831. The trigger 831 may be configured to be gripped with fingers of the user to displace the trigger 831 and the thread rail 824 proximally to a priming state when a proximally directed force is applied by the fingers. When displaced proximally, the thread rail threads 825 disengage from the coupling member threads 819 to allow the plunger 820 to be longitudinally translated in response to externally applied longitudinal forces.

As shown, the handle 830 includes a trigger locking member 840. The locking member 840 may be configured to maintain the trigger 831 and the thread rail 824 in the priming state without continued application of the proximally directed force on the trigger 831.

FIGS. 8A-8C depict the locking member 840 including a knob 856 and a shaft 857. As depicted, the knob 856 extends outwardly from a face of the handle 830. In some embodiments, the locking member 840 may include two knobs 856 where a first knob 856 extends from a first face and a second knob 856 extends from a second face of the handle 830. The knob 856 may be configured to be grasped and rotated about a longitudinal axis of the locking member 840 by the fingers of a user. As depicted in FIG. 8A, the knob 856 is formed in a rectangular shape. In other embodiments, the knob 856 may be formed in any suitable shape. For example, the knob 856 may be formed in the shape of an arrow, an oval, a triangle, etc. The knob 856 may include an indicium to indicate the state (e.g., locked or unlocked) of the locking member 840. For example, the knob 856 may include a printed or embossed arrow, text, bumps, recesses, or any other suitable indicium.

The shaft 857 may extend from the knob 856 through a passage in the handle 830. An end of the shaft 857 opposite the knob 856 may be rotatably coupled to a wall of the handle 830 opposite of the passage. The locking member 840 is configured to be rotatable within the passage while axial translation is prevented. In the illustrated embodiment, an attracting magnet member 858 is disposed on a side of the shaft 857. A repelling magnet member 859 is disposed on an opposing side of the shaft 857. A trigger magnet 860 is disposed on a proximal end of the thread rail 824. The magnets 858, 859, 860 may be formed in disc shape and be permanently axially magnetized where one side has a north magnetic pole and the opposite side has a south magnetic pole. The magnets 858, 859, 860 may comprise any suitable material capable of being permanently magnetized. For example, the magnets 858, 859, 860 may be formed of neodymium, ceramic, samarium cobalt, alnico, ferrite, or any other suitable material.

The trigger magnet 860 may be fixedly coupled to a proximal portion of the trigger 831 such that either the north or south magnetic pole side is facing proximally. The attracting magnet 858 may be fixedly coupled to the shaft 857 in axial alignment with the trigger magnet 860 such that the side with the opposite magnetic pole than the trigger magnet 860 faces outward. The repelling magnet 859 may be fixedly coupled to the shaft 857 in axial alignment with the trigger magnet 860 such that the side with the same magnetic pole as the trigger magnet 860 faces outward. For example, the trigger magnet 860 can be disposed on the proximal end of the thread rail 824 with the side having the north magnetic pole facing proximally. The attracting magnet 858 can be coupled to the shaft 857 with the side having the south magnetic force facing outward and the repelling magnet 859 can be coupled to the shaft with the side having the north magnetic pole facing outward. This configuration allows for the trigger magnet 860 to be attracted and drawn proximally to the attracting magnet 858 when the attracting magnet 858 is oriented toward the trigger magnet 860 by rotation of the knob 856. This configuration also allows for the repelling magnet 859 to be repelled and displaced distally when the repelling magnet 858 is oriented toward the trigger magnet 860. When the trigger magnet 860 and the attracting magnet 858 are oriented toward each other, the trigger 831 and thread rail 824 are displaced proximally such that the rail threads 825 are disengaged from the coupling nut threads 819 and the inflation device is in a priming state. When the trigger magnet 860 and the repelling magnet 859 are oriented toward each other, the trigger 831 and thread rail 824 are displaced distally such that the rail threads 825 are engaged with the coupling nut threads 819 and the inflation device 800 is in a pressurization state.

FIG. 8B depicts the inflation device 800 in the pressurization state where the rail threads 825 are engaged with the coupling nut threads 819, the trigger 831 is in a distal position, and the locking member 840 is configured such that the repelling magnet 859 is oriented toward the trigger magnet 860. In use, the locking member 840 is actuated when the user grips the knob 856 and rotates the knob 856 clockwise or counter-clockwise approximately 180 degrees such that the attracting magnet 858 is oriented toward the trigger magnet 860. The user also grips the handle 830 and applies a proximally directed finger force to the trigger 831 to displace the trigger 831 proximally. Proximal displacement of the trigger 831 radially retracts the thread rail 824 to disengage the rail threads 825 from the coupling nut threads 819 and configure the inflation device 800 in the priming state.

FIG. 8C shows the inflation device in the priming state. As shown in FIG. 8C, when the trigger 831 is displaced proximally, the trigger magnet 860 magnetically couples with the attracting magnet 858 to hold the trigger 831 and thread rail 824 in the priming state. In other words, the trigger 831 and thread rail 824 are held in the priming state by the magnetic attraction of the trigger magnet 860 and the attracting magnet 858. The user may then longitudinally translate the plunger 820 to prime or deflate the inflatable medical device in fluid communication with the inflation device 800 without maintaining the proximally directed finger force on the trigger 831.

When desired, the locking member 840 may be de-actuated by rotating the knob 856 either clockwise or counter-clockwise approximately 180 degrees until the repelling magnet 859 is oriented toward the trigger magnet 860. The magnetic repulsion of the magnets 859, 860 causes the trigger 831 to be displaced distally resulting in engagement of the rail threads 825 with the coupling nut threads 819 and converting the inflation device 800 to the pressurization state.

Figure 9A:
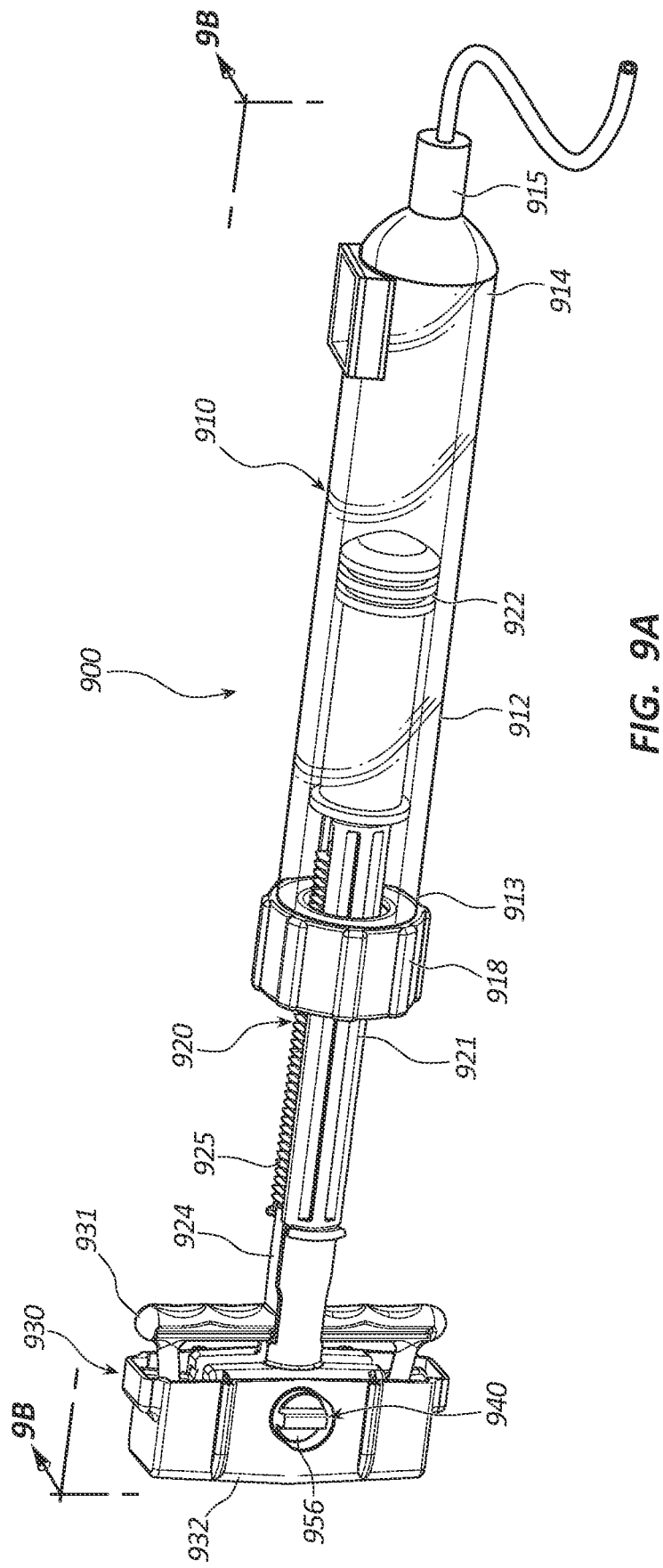
FIG. 9A is a perspective view of another embodiment of an inflation device with a trigger locking member.
Figure 9B:
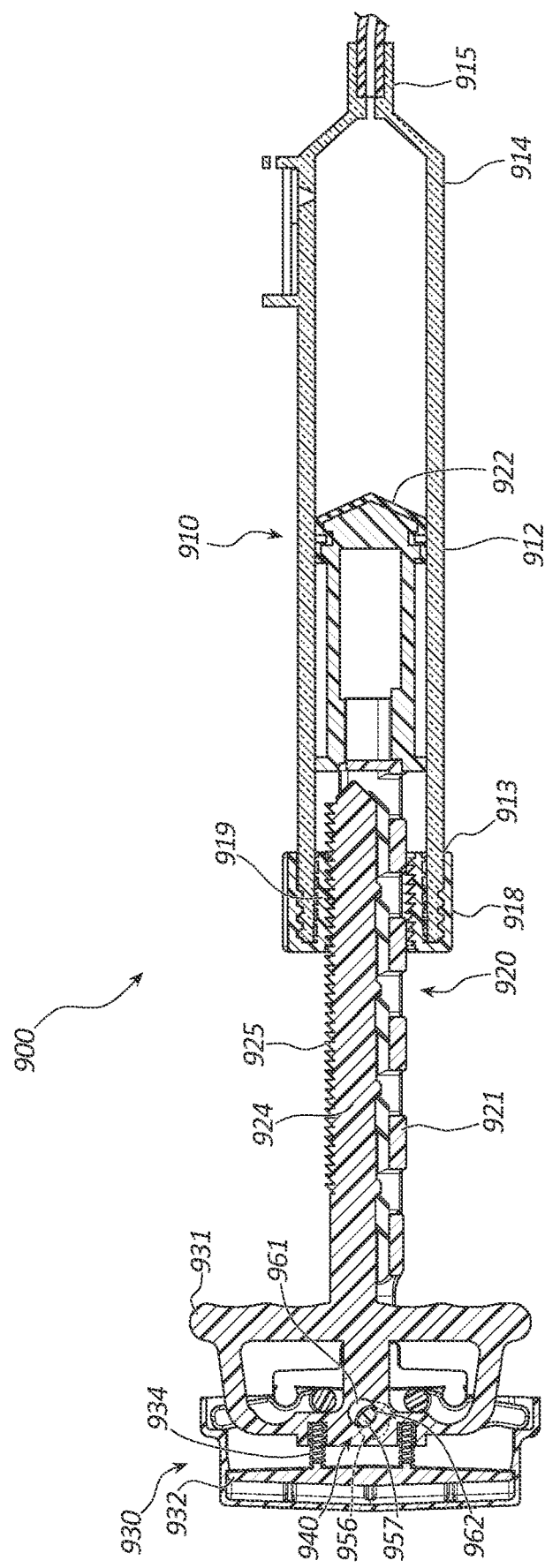
FIG. 9B is a cross-sectional view, taken through plane 9B-9B of FIG. 9A, of the inflation device of FIG. 9A in a pressurization state.
Figure 9C:
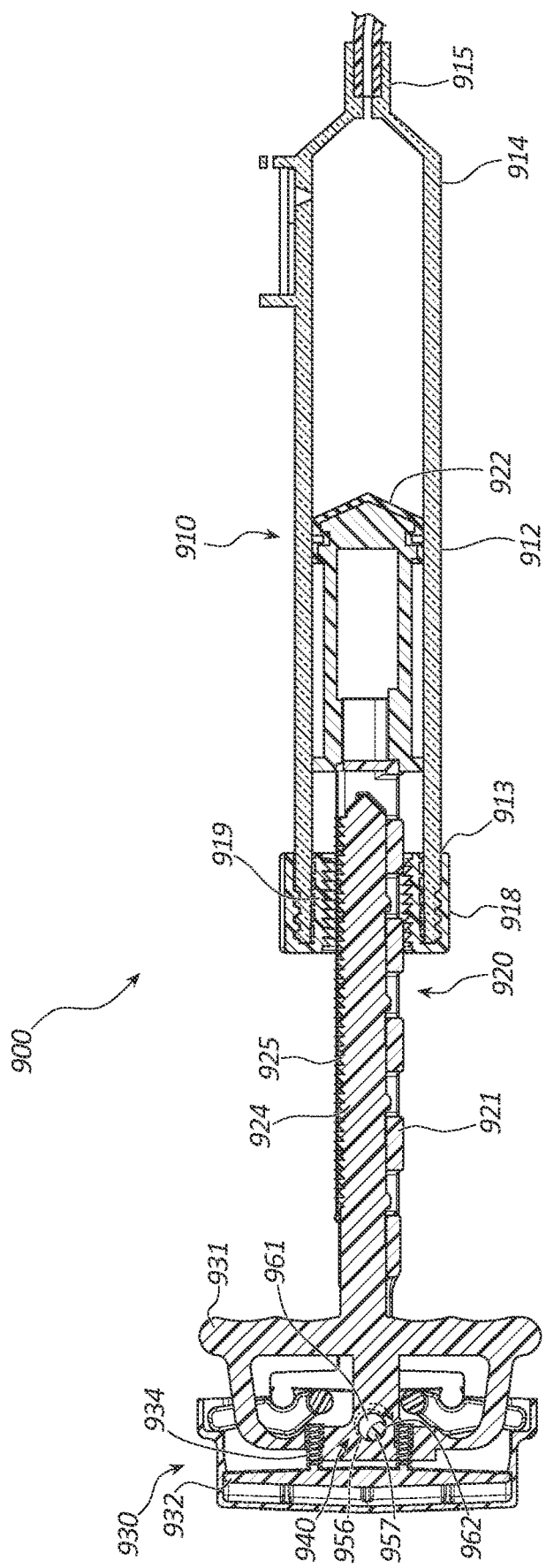
FIG. 9C is a cross-sectional view, taken through plane 9B-9B of FIG. 9A, of the inflation device of FIG. 9A in a priming state.

FIGS. 9A-9C depict another embodiment of an inflation device 900. In the illustrated embodiment, the inflation device 900 is partially comprised of a syringe 910. The inflation device 900 includes three broad groups of components; each group may have numerous subcomponents and parts. The three broad component groups are: a body component such as syringe body 912, a pressurization component such as plunger 920, and a handle 931.

The syringe body 912 may be formed of a generally cylindrical hollow tube configured to receive the plunger 920. The syringe body 912 may include an inlet/outlet port 915 located adjacent the distal end 914 of the syringe body 912. In some embodiments, a coupling member 918 may be coupled to the syringe body 912 adjacent the proximal end 913 of the syringe body 912. The coupling member 918 may include a center aperture configured to allow the plunger 920 to pass through the coupling member 918 into the syringe body 912. Further, the coupling member 918 may include coupling member threads 919 configured to selectively couple the coupling member 918 to the plunger 920. For example, the coupling member 918 may comprise a polymeric nut at the proximal end 913 of the syringe body 912.

The plunger 920 may be configured to be longitudinally displaceable within the syringe body 912. The plunger 920 may be comprised of a plunger shaft 921 coupled to a plunger seal 922 at the distal end of the plunger shaft 921. The plunger shaft 921 may also be coupled to the handle 930 at the proximal end of the plunger shaft 921, with the plunger shaft 921 spanning the distance between the plunger seal 922 and the handle 930. Additionally, the coupling member 918 may engage rail threads 925 configured to couple the plunger 920 to the coupling member 918. The rail threads 925 may be configured such that they may be retracted within the plunger shaft 921. In some embodiments, the rail threads 925 do not extend 360 degrees around the axis of the plunger shaft 921. For example, the rail threads 925 may be formed on a thread rail 924 on the plunger shaft 921. The thread rail 924 may be retracted from the coupling member threads 919 by actuating a mechanism such as a trigger 931.

The handle 930 broadly refers to the group of components coupled to the proximal end of the plunger 920, some of which may be configured to be graspable by a user. In certain embodiments, the handle 930 may be configured such that the user may manipulate the position of the plunger 920 by manipulating the handle 930. Further, in some embodiments, the handle 930 may be an actuator mechanism configured to manipulate components of the inflation device 900.

As illustrated in FIGS. 9A-9C, the handle 930 includes a grip portion 932 and a trigger 931. The grip portion 932 may be configured to be gripped by a hand of a user. While gripping, the user may either rotate the handle 930 or longitudinally displace the handle 930 to inflate or deflate a medical device in fluid communication with the syringe 910. The plunger shaft 921 extends distally from the grip portion 932. The plunger shaft 921 may be fixedly coupled to the grip portion 932.

As depicted in FIGS. 9A-9C, the trigger 931 is operatively coupled to the grip portion 932. The trigger 931 is shown to extend distally from the grip portion 932. The trigger 931 may be configured to be longitudinally displaceable relative to the grip portion 932. The thread rail 924 extends distally from the trigger 931 and is fixedly coupled to the trigger 931. The trigger 931 may be configured to be gripped with fingers of the user to displace the trigger 931 and the thread rail 924 proximally to a priming state when a proximally directed force is applied by the fingers. When displaced proximally, the thread rail threads 925 disengage from the coupling member threads 919 to allow the plunger 920 to be longitudinally translated in response to externally applied longitudinal forces.

As shown, the handle 930 includes a trigger locking member 940. The locking member 940 may be configured to maintain the trigger 931 and the thread rail 924 in the priming state without continued application of the proximally directed force on the trigger 931.

FIGS. 9A-9C depict the locking member 940 including a knob 956 and a shaft 957. As depicted, the knob 956 extends outwardly from a face of the handle 930. In some embodiments, the locking member 940 may include two knobs 956 where a first knob 956 extends from a first face and a second knob 956 extends from a second face of the handle 930. The knob 956 may be configured to be grasped and rotated about a longitudinal axis of the locking member 940 by the fingers of a user. As depicted in FIG. 9A, the knob 956 is formed in a rectangular shape. In other embodiments, the knob 956 can be formed in any suitable shape. For example, the knob 956 can be formed in the shape of an arrow, an oval, a triangle, etc. The knob 956 may include an indicium to indicate the state (e.g., locked or unlocked) of the locking member 940. For example, the knob 956 may include a printed or embossed arrow, text, bumps, recesses, or any other suitable indicium.

In the illustrated embodiment, the shaft 957 extends from the knob 956 through a passage in the handle 930. An end of the shaft 957 opposite the knob 956 may be rotatably coupled to a wall of the handle 930 opposite of the passage. The locking member 940 can be rotatable within the passage while axial translation is prevented. The shaft 957 also passes through a circular shaped cam passage 961 disposed in the trigger 931. The shaft 957 includes a cam lobe 962 shown to extend radially outwardly from one side of the shaft 957. The shaft 957 may have a transverse cross-section having an elliptical shape. A center point of the cam lobe 962 may be radially offset from a longitudinal axis of the shaft 957. The cam lobe 962 may be oriented in alignment with the knob 956. In certain embodiments, the cam passage 961 may include a recess or detent configured to receive a portion of the cam lobe 962 to provide a tactile feedback to the user regarding a state (e.g., locked or unlocked) of the locking member 940.

FIG. 9B depicts the inflation device 900 in a pressurization state where the rail threads 925 are engaged with the coupling nut threads 919, the trigger 931 is in a distal position, and the locking member 940 is configured such that the cam lobe 962 is oriented distally. In use, the user grips the handle 930 and applies a proximally directed finger force to the trigger 931 to displace the trigger 931 proximally. Proximal displacement of the trigger 931 radially retracts the thread rail 924 to disengage the rail threads 925 from the coupling nut threads 919 and configure the inflation device 900 in the priming state as shown in FIG. 9C. The locking member 940 may be actuated when the user grips the knob 956 and rotates the knob 956 clockwise or counter-clockwise approximately 180 degrees such that the cam lobe 962 is oriented proximally. In this orientation, the cam lobe 962 engages with the cam passage 961 to lock the cam passage 961 and trigger 931 in a proximal position. The user may then longitudinally translate the plunger 920 to prime or deflate the inflatable medical device in fluid communication with the inflation device 900 without maintaining the proximally directed finger force on the trigger 931.

When desired, the locking member 940 may be de-actuated by rotating the knob 956 either clockwise or counter-clockwise approximately 180 degrees until the cam lobe 962 is oriented distally and parallel to the longitudinal axis of the inflation device 900. The trigger spring 934 can apply a distally directed force to the trigger 931 causing the cam passage 961 and the trigger 931 to be displaced distally resulting in engagement of the rail threads 925 with the coupling nut threads 919 and converting the inflation device 900 to the pressurization state.

FIGS. 10A-10H depict another embodiment of an inflation device 1000. In the illustrated embodiment, the inflation device 1000 is partially comprised of a syringe 1010. The inflation device 1000 includes three broad groups of components; each group may have numerous subcomponents and parts. The three broad component groups are: a body component such as syringe body 1012, a pressurization component such as plunger 1020, and a handle 1030.

The syringe body 1012 may be formed of a generally cylindrical hollow tube configured to receive the plunger 1020. The syringe body 1012 may include an inlet/outlet port 1015 located adjacent the distal end 1014 of the syringe body 1012. In some embodiments, a coupling member 1018 may be coupled to the syringe body 1012 adjacent the proximal end 1013 of the syringe body 1012. The coupling member 1018 may include a center aperture configured to allow the plunger 1020 to pass through the coupling member 1018 into the syringe body 1012. Further, the coupling member 1018 may include coupling member threads 1019 configured to selectively couple the coupling member 1018 to the plunger 1020. For example, the coupling member 1018 may comprise a polymeric nut at the proximal end 1013 of the syringe body 1012.

The plunger 1020 may be configured to be longitudinally displaceable within the syringe body 1012. The plunger 1020 may be comprised of a plunger shaft 1021 coupled to a plunger seal 1022 at the distal end of the plunger shaft 1021. The plunger shaft 1021 may also be coupled to the handle 1030 at the proximal end of the plunger shaft 1021, with the plunger shaft 1021 spanning the distance between the plunger seal 1022 and the handle 1030. The plunger 1020 may further comprise a pair of thread rails 1024 moveably disposed within open, opposing, longitudinal channels. The thread rails 1024 comprise rail threads 1025 that are configured to engage with coupling nut threads 1019. The thread rails 1024 may extend parallel to each other into the syringe body 1012. A central passage 1063 may extend longitudinally between the thread rails 1024. The thread rails 1024 are configured to be displaced radially inward and outward as the inflation device 1000 is used as will be described below. A resilient member 1067 may be operably coupled to a proximal and/or distal end of the thread rails 1024. In the illustrated embodiment, the resilient member 1067 is an elastomeric band disposed around the proximal and distal ends of the thread rails 1024. In other embodiments, the resilient member 1067 may be a spring. The resilient member 1067 is configured to facilitate the inward displacement of the thread rails 1024.

In some embodiments, the design of the rail threads 1025 and the coupling nut threads 1019 and the materials of the thread rails 1024 and the coupling nut 1018 may be configured to function together to provide functional characteristics of the inflation device 1000. For example, the angle of the rail threads 1025 and the coupling nut threads 1019 may be configured to reduce the torque force required to pressurize the syringe 1010. Based on using a 45 degree thread angle as a reference, the torque force may be reduced from 11% to 58% when the thread angle (a) ranges from 50 degrees to 90 degrees. Some devices within the scope of this disclosure may utilize thread angles (a) between 45 degrees and 90 degrees. Additionally, the torque force may be further reduced by reducing the coefficient of friction between the rail threads 1025 and the coupling nut threads 1019 through a selection of low friction materials or additives. A reduction in the torque force may be beneficial to reduce a repetitive strain on a user's hand and arm during an inflation procedure and to reduce stress/deformation of the device 1000 during pressurization.

The handle 1030 broadly refers to the group of components coupled to the proximal end of the plunger 1020, some of which may be configured to be graspable by a user. In certain embodiments, the handle 1030 may be configured such that the user may manipulate the position of the plunger 1020 by manipulating the handle 1030. Further, in some embodiments, the handle 1030 may be an actuator mechanism configured to manipulate components of the inflation device 1000.

As illustrated in FIGS. 10A-10D, the handle 1030 includes a grip portion 1032 and a trigger 1031. The grip portion 1032 may be configured to be gripped by a hand of a user. While gripping, the user may either rotate the handle 1030 or longitudinally displace the handle 1030 to inflate or deflate a medical device in fluid communication with the syringe 1010. A crank member 1033 may be selectively disposed within the grip portion 1032. The crank member 1033 may be configured to be selectively extended laterally from the grip portion 1032 to provide rotational leverage when the handle 1030 is rotated. The plunger shaft 1021 extends distally from the grip portion 1032. The plunger shaft 1021 may be fixedly coupled to the grip portion 1032.

As depicted in FIGS. 10A-10D, the trigger 1031 is operatively coupled to the grip portion 1032. The trigger 1031 is shown to extend distally from the grip portion 1032. The trigger 1031 may be configured to be longitudinally displaceable relative to the grip portion 1032. The trigger 1031 may be configured to be gripped with fingers of the user to displace the trigger 1031 proximally to a priming state when a proximally directed force is applied by the fingers.

Figure 10A:
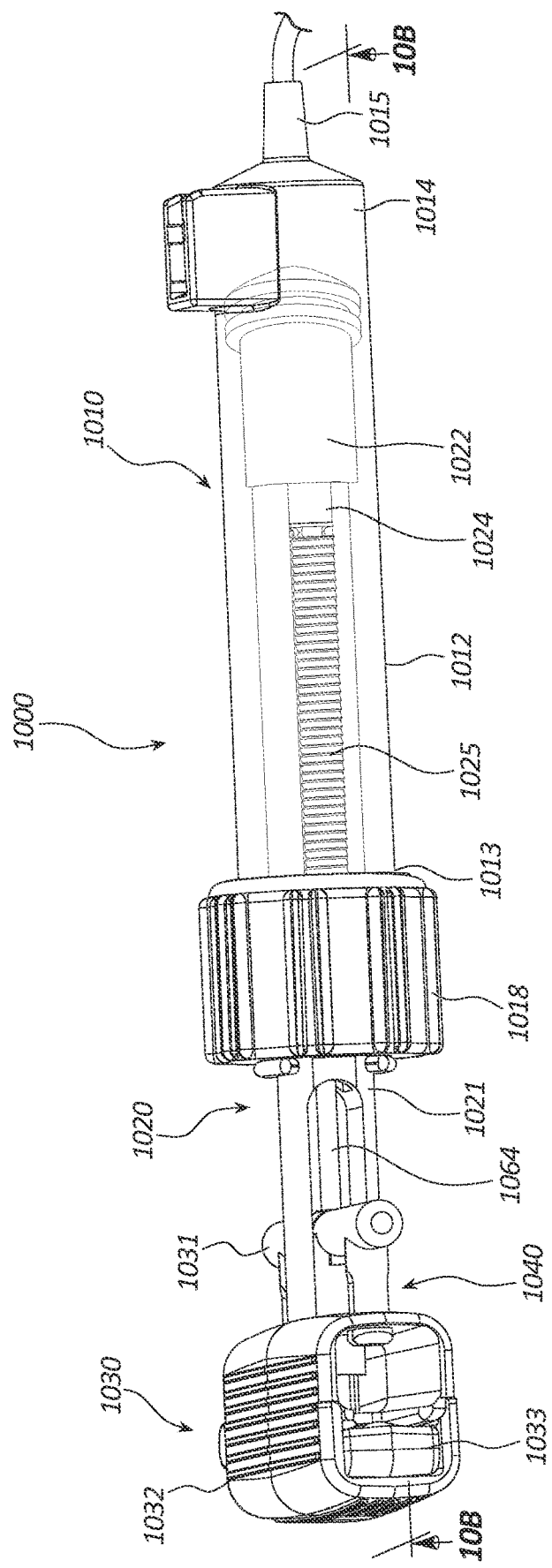
FIG. 10A is a perspective view of another embodiment of an inflation device with a trigger locking member.
Figure 10D:
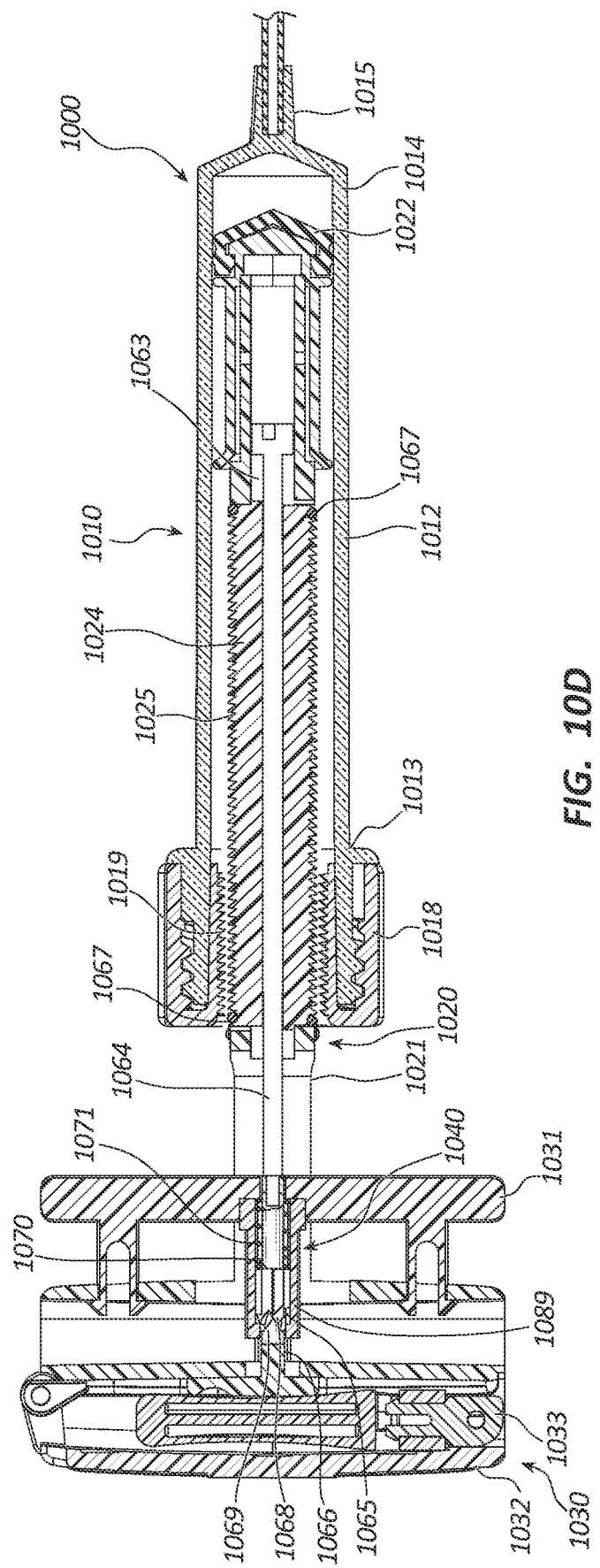
FIG. 10D is a cross-sectional view, taken through plane 10B-10B of FIG. 10A, of the inflation device of FIG. 10A in a priming state.

The handle 1030 includes a trigger locking member 1040. The locking member 1040 may be configured to lock the thread rails 1024 in a pressurization state where the thread rails 1024 are displaced outwardly and the rail threads 1025 and the coupling nut threads 1019 are engaged (FIGS. 10B-10C), and in the priming state where the thread rails 1024 are displaced inwardly and the rail threads 1025 and the coupling nut threads 1019 are disengaged without continued application of the proximally directed force on the trigger 1031 (FIG. 10D).

As illustrated in FIGS. 10B-10H, the locking member 1040 includes a cam shaft 1064, an upper cam 1065, a handle feature 1066, and a trigger barrel 1070. The cam shaft 1064 includes a proximal portion that is rotatably coupled to the trigger 1031 and a distal portion that is disposed in the central channel 1063 between the thread rails 1024. The distal portion has a cross-sectional oval shape having two opposing cam lobes 1072 extending outwardly from a longitudinal axis. The proximal portion of the cam shaft 1064 is fixedly coupled to the upper cam 1065.

The upper cam 1065 includes at least one angled projection 1068 disposed at a proximal end. As depicted, the upper cam 1065 includes four angled projections 1068 equally circumferentially disposed about the proximal end. In other words, the angled projections 1068 have a circumferential spacing of about 90 degrees and an included angle of about 90 degrees. In other embodiments, the upper cam 1065 may include two, three, five, six or more angled projections 1068. The upper cam 1065 also includes a rotation guide 1087. The rotation guide 1087 is disposed on an exterior surface of the upper cam 1065. The upper cam 1065 may include two, three, four, or more rotation guides 1087 circumferentially disposed about the upper cam 1065. The rotation guide 1087 may be longitudinally oriented relative to the upper cam 1065 and may comprise an angled proximal end 1088. The angled proximal end 1088 may be aligned with the angled projection 1068 of the upper cam 1065.

As illustrated in FIGS. 10B-10C, the handle feature 1066 may be fixedly coupled to the handle 1030 and extend distally from a portion of the handle 1030. The handle feature 1066 includes at least one angled projection 1069 disposed at a distal end. In the illustrated embodiment, the handle feature 1066 includes four angled projections 1069 equally circumferentially disposed about the distal end. In other words, the angled projections 1069 have a circumferential spacing of about 90 degrees and an included angle of about 90 degrees. In other embodiments, the handle feature 1066 may include two, three, five, six or more angled projections 1069. The angled projections 1069 of the handle feature 1066 may be configured to engage with the angled projections 1068 of the upper cam 1065 to facilitate rotation of the upper cam 1065 during use.

The trigger barrel 1070 may be fixedly coupled to the trigger 1031. The upper cam 1065 and the handle feature 1066 may be at least partially disposed within the trigger barrel 1070. The trigger barrel 1070 may be configured to be longitudinally displaceable relative to the upper cam 1065 and the handle feature 1066. The upper cam 1065 may be rotatable within the trigger barrel 1070. At least one barrel guide 1089 is disposed within the trigger barrel 1070. The barrel guide 1070 includes an angled distal end 1090 that is configured to engage with the angled proximal end 1088 of the rotation guide 1087 to facilitate rotation of the upper cam. The proximal portion of the cam shaft 1064 may be slideably disposed within the barrel guide 1070.

A compression member 1071 (e.g., a spring) may be disposed around the proximal portion of the cam shaft 1064 within the trigger barrel 1070 between the upper cam 1065 and an end wall of the trigger barrel 1070. The compression member 1071 may apply a proximally directed force to the upper cam 1065 to facilitate engagement of the angled projections 1068, 1069 and to a distally directed force to the trigger 1031 to displace the trigger 1031 distally.

Figure 10E:
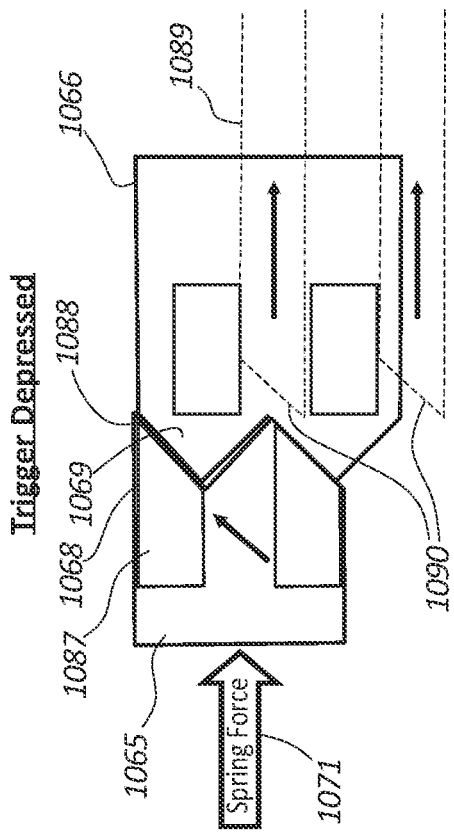
FIG. 10E is an illustrative depiction of a portion of the trigger locking member of FIG. 10A in a first locked state.

FIG. 10B depicts the inflation device 1000 in a pressurization state where the rail threads 1025 are engaged with the coupling nut threads 1019, the trigger 1031 is in a distal position, and the locking member 1040 is configured such that the cam lobes 1072 are displacing the thread rails 1024 outwardly. In use, the user grips the handle 1030 and applies a first proximally directed finger force to the trigger 1031 to displace the trigger 1031 proximally. FIG. 10E shows the locking member 1040 in a first locked state prior to proximal displacement of the trigger 1031. In the first locked state, the trigger 1031 and trigger barrel 1070 are in a distal position, the angled projections 1068, 1069 are partially engaged, the rotation guide 1087 and the barrel guide 1089 are disposed parallel and alongside one another to prevent rotation of the upper cam 1065, the compression member 1071 is uncompressed, the cam lobes 1072 are oriented such that they engage with the thread rails 1024, and the rail threads 1025 are engaged with the coupling member threads 1019.

Figure 10F:
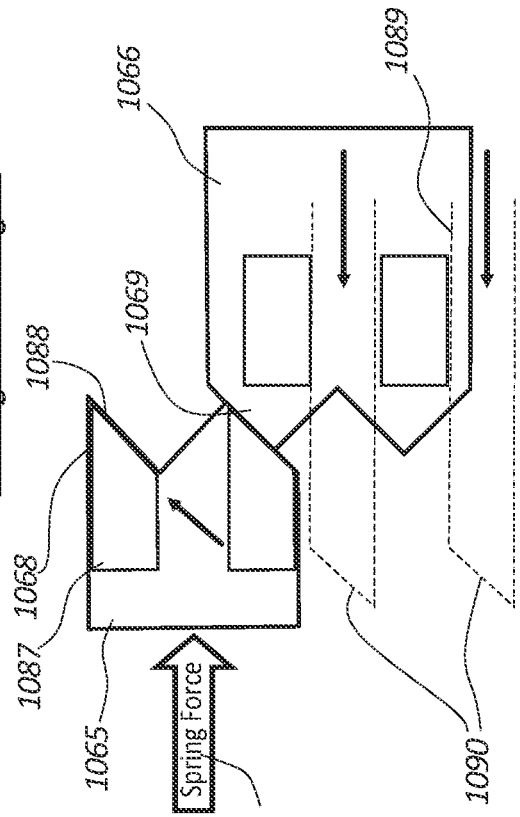
FIG. 10F is an illustrative depiction of a portion of the trigger locking member of FIG. 10A in a trigger depressed state.

FIG. 10F shows the locking member 1040 in a trigger depressed state following proximal displacement of the trigger 1031. In the trigger depressed state, the trigger 1031 and the trigger barrel 1070 are in a proximal position, the barrel guide 1089 is displaced proximally such that the barrel guide 1089 is positioned proximally of the rotation guide 1087, allowing the upper cam 1065 to rotate when the compressed compression member 1071 applies a proximally directed force to the upper cam 1065, causing the upper cam 1065 to rotate and be displaced proximally when the angled projections 1068, 1069 become fully engaged, the cam shaft 1064 is partially rotated from the resting state, and the cam lobes 1072 are partially disengaged from the thread rails 1024.

Figure 10G:
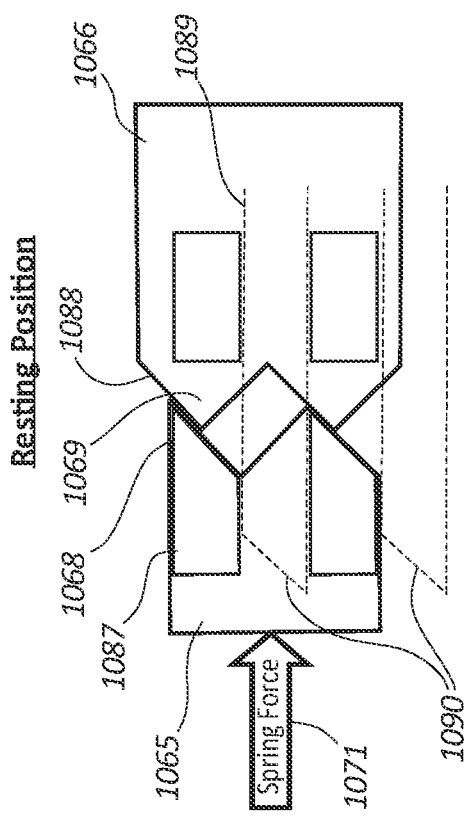
FIG. 10G is an illustrative depiction of a portion of the trigger locking member of FIG. 10A in a trigger release state.

FIG. 10G shows the locking member 1040 in a trigger release state. In the trigger release state the trigger 1031 and trigger barrel 1070 are distally displaced from the proximal position by a distally directed force applied by the compression member 1071, the angled distal end 1090 is engaged with the angled proximal end 1088 causing the upper cam 1065 to rotate further, the angled projections 1068, 1069 are partially engaged, the cam shaft 1064 is rotated further, and the cam lobes 1072 are additionally disengaged from the thread rails 1024.

Figure 10H:
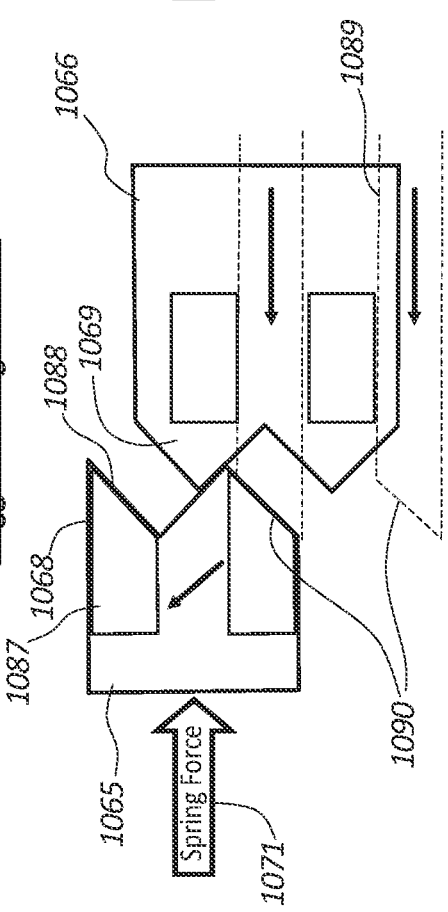
FIG. 10H is an illustrative depiction of a portion of the trigger locking member of FIG. 10A in a second locked state.

FIG. 10H shows the locking member 1040 in a second locked state following rotation of the upper cam 1065 and the cam shaft 1064. In the second resting state, the trigger 1031 and trigger barrel 1070 are in the distal position, the angled projections 1068, 1069 are partially engaged, the rotation guide 1087 and the barrel guide 1089 are disposed parallel and alongside one another, the compression member 1071 applies a distally directed force to the trigger 1031 to maintain the trigger 1031 in the distal position, the cam lobes 1072 are oriented such that they are disengaged from the thread rails 1024, and the rail teeth 1025 are disengaged from the coupling member teeth 1019. When the locking member 1040 is in the second resting state, the inflation device 1000 is in the priming state as shown in FIG. 10D. The user may then longitudinally translate the plunger 1020 to prime or deflate the inflatable medical device in fluid communication with the inflation device 1000 without maintaining the proximally directed finger force on the trigger 1031. In some embodiments, the trigger 1031 may be depressed a second time to rotate the locking member 1040 and the cam shaft 1064 a second time such that the cam lobes 1072 are engaged with the thread rails 1024 and the rail threads 1025 are engaged with the coupling member threads 1019. In other words, the inflation device 1000 returns to the pressurization state as shown in FIG. 10A following the second proximal displacement of the trigger 1031.

Figure 11A:
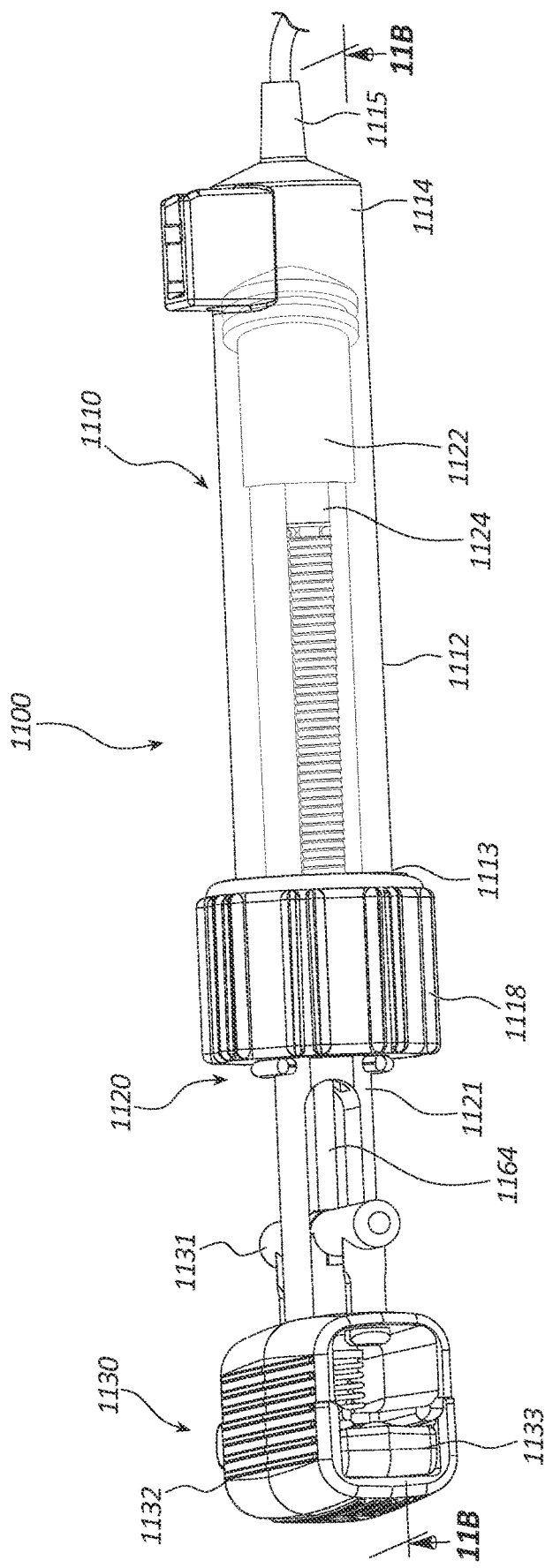
FIG. 11A is a perspective view of another embodiment of an inflation device with a trigger toggle member.
Figure 11B:
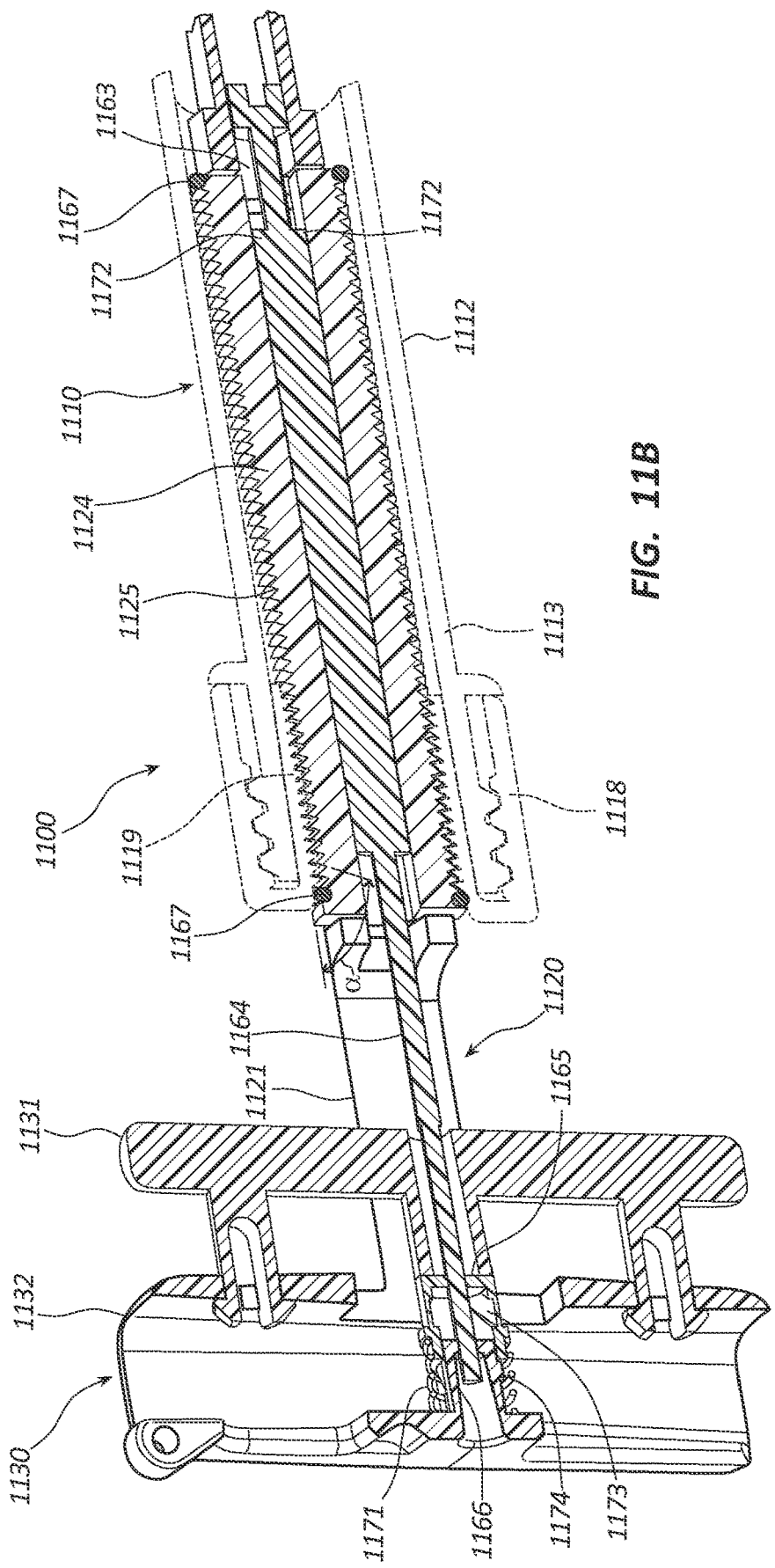
FIG. 11B is a cross-sectional view, taken through plane 11B-11B of FIG. 11A, of the inflation device of FIG. 11A in a pressurization state.
Figure 11C:
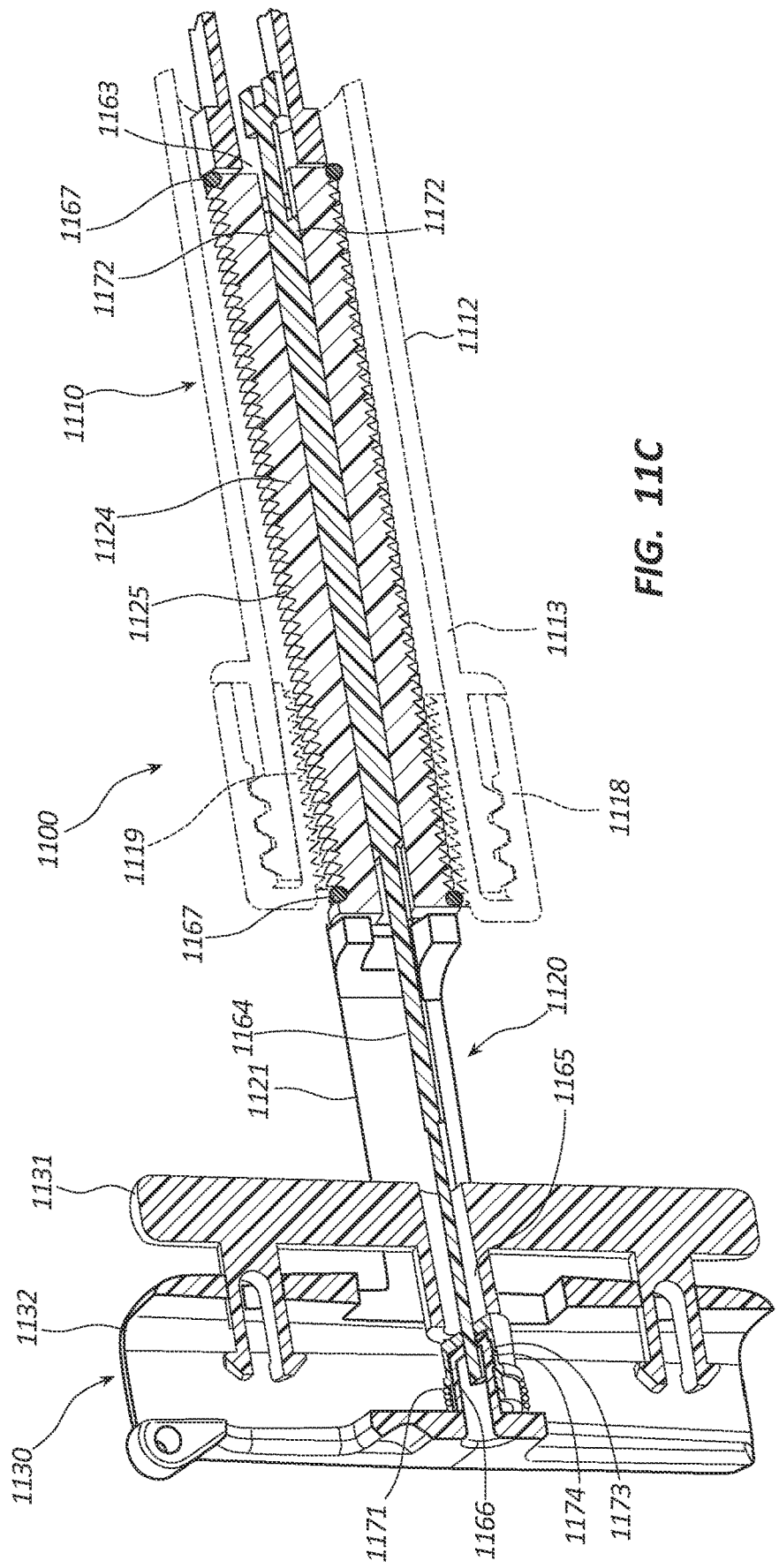
FIG. 11C is a cross-sectional view of the inflation device of FIG. 11A in a priming state.

FIGS. 11A-11C depict another embodiment of an inflation device 1100. In the illustrated embodiment, the inflation device 1100 is partially comprised of a syringe 1110. The inflation device 1100 includes three broad groups of components; each group may have numerous subcomponents and parts. The three broad component groups are: a body component such as syringe body 1112, a pressurization component such as plunger 1120, and a handle 1130.

The syringe body 1112 may be formed of a generally cylindrical hollow tube configured to receive the plunger 1120. The syringe body 1112 may include an inlet/outlet port 1115 located adjacent the distal end 1114 of the syringe body 1112. In some embodiments, a coupling member 1118 may be coupled to the syringe body 1112 adjacent the proximal end 1113 of the syringe body 1112. The coupling member 1118 may include a center aperture configured to allow the plunger 1120 to pass through the coupling member 1118 into the syringe body 1112. Further, the coupling member 1118 may include coupling member threads 1119 configured to selectively couple the coupling member 1118 to the plunger 1120. For example, the coupling member 1118 may comprise a polymeric nut at the proximal end 1113 of the syringe body 1112.

The plunger 1120 may be configured to be longitudinally displaceable within the syringe body 1112. The plunger 1120 may be comprised of a plunger shaft 1121 coupled to a plunger seal 1122 at the distal end of the plunger shaft 1121. The plunger shaft 1121 may also be coupled to the handle 1130 at the proximal end of the plunger shaft 1121, with the plunger shaft 1121 spanning the distance between the plunger seal 1122 and the handle 1130. The plunger 1120 may further comprise a pair of thread rails 1124 moveably disposed within open, opposing, longitudinal channels. The thread rails 1124 comprise rail threads 1125 that are configured to engage with coupling nut threads 1119. The thread rails 1124 may extend parallel to each other into the syringe body 1112. A central passage 1163 may extend longitudinally between the thread rails 1124. The thread rails 1124 are configured to be displaced inwardly and outwardly as the inflation device 1100 is used, as will be described below. A resilient member 1167 may be operably coupled to a proximal and/or distal end of the thread rails 1124. In the illustrated embodiment, the resilient member 1167 is an elastomeric band disposed around the proximal and distal ends of the thread rails 1124. In other embodiments, the resilient member 1167 may be a spring. The resilient member 1067 is configured to facilitate the inward displacement of the thread rails 1124.

In some embodiments, the design of the rail threads 1125 and the coupling nut threads 1119 and the materials of the thread rails 1124 and the coupling nut 1118 may be configured to function together to provide functional characteristics of the inflation device 1100. For example, the angle of the rail threads 1025 and the coupling nut threads 1119 may be configured to reduce the torque force required to pressurize the syringe 1110. Based on using a 45 degree thread angle as a reference, the torque force may be reduced from 11% to 58% when the thread angle (a) ranges from 50 degrees to 90 degrees. Some devices within the scope of this disclosure may utilize thread angles (a) between 45 degrees and 90 degrees. Additionally, the torque force may be further reduced by reducing the coefficient of friction between the rail threads 1125 and the coupling nut threads 1119 through a selection of low friction materials or additives. A reduction in the torque force may be beneficial to reduce a repetitive strain on a user's hand and arm during an inflation procedure and to reduce stress/deformation of the device 1100 during pressurization.

The handle 1130 broadly refers to the group of components coupled to the proximal end of the plunger 1120, some of which may be configured to be graspable by a user. In certain embodiments, the handle 1130 may be configured such that the user may manipulate the position of the plunger 1120 by manipulating the handle 1130. Further, in some embodiments, the handle 1130 may be an actuator mechanism configured to manipulate components of the inflation device 1100.

As illustrated in FIGS. 11A-11C, the handle 1130 includes a grip portion 1132 and a trigger 1131. The grip portion 1132 may be configured to be gripped by a hand of a user. While gripping, the user may either rotate the handle 1130 or longitudinally displace the handle 1130 to inflate or deflate a medical device in fluid communication with the syringe 1110. A crank member 1133 may be selectively disposed within the grip portion 1132. The crank member 1133 may be configured to be selectively extended laterally from the grip portion 1132 to provide rotational leverage when the handle 1130 is rotated. The plunger shaft 1121 extends distally from the grip portion 1132. The plunger shaft 1121 may be fixedly coupled to the grip portion 1132.

As depicted in FIGS. 11A-11C, the trigger 1131 is operatively coupled to the grip portion 1132. The trigger 1131 is shown to extend distally from the grip portion 1132. The trigger 1131 may be configured to be longitudinally displaceable relative to the grip portion 1132. The trigger 1131 may be configured to be gripped with fingers of the user to displace the trigger 1131 proximally to a priming state when a proximally directed force is applied by the fingers.

The handle 1130 may be configured to displace the thread rails 1124 between a pressurization state where the thread rails 1124 are displaced outwardly and the rail threads 1125 and the coupling nut threads 1119 are engaged (FIG. 11B) to the priming state where the thread rails 1124 are displaced inwardly and the rail threads 1125 and the coupling nut threads 1119 are disengaged (FIG. 11C).

As illustrated in FIGS. 11B-11C, the inflation device 1100 includes a cam shaft 1164, a threaded sleeve 1165, and a threaded handle feature 1166. The cam shaft 1164 includes a proximal portion that is rotatably coupled to the trigger 1131 and a distal portion that is disposed in the central channel 1163 between the thread rails 1124. The distal portion has a cross-sectional oval shape having two opposing cam lobes 1172 extending outwardly from a longitudinal axis. The proximal portion of the cam shaft 1164 is moveably coupled to the threaded sleeve 1165. The proximal portion includes a square shape configured to pass through a square passage of the threaded sleeve 1165 such that the threaded sleeve 1165 is longitudinally translatable relative to the proximal portion but is non-rotatable relative to the proximal portion. In other words, the threaded sleeve 1165 may be longitudinally displaced relative to the threaded sleeve 1165 and cause the proximal portion to rotate when the threaded sleeve 1165 is rotated. The threaded sleeve 1165 includes two internal threads 1173 extending from a proximal opening to a distal end. The internal threads 1173 are configured to rotate the threaded sleeve 1165 and the cam shaft 1164 about 90 degrees or a quarter turn when the internal threads 1173 are engaged with external threads 1174 of the threaded handle feature 1166. The threaded handle feature 1066 is fixedly coupled to the handle 1030 and extends distally from the handle 1030. A compression member 1171 (e.g., a spring) is disposed around the threaded handle feature 1166 and engages with a proximal end of the threaded sleeve 1165. The compression member 1171 may be configured to be compressed when the threaded sleeve 1165 is displaced proximally by the trigger 1131 and to apply a distally directed force to the threaded sleeve 1165 and the trigger 1131 to return the trigger 1131 to a distal position.

FIG. 11B depicts the inflation device 1100 in a pressurization state where the rail threads 1125 are engaged with the coupling nut threads 1119, the trigger 1031 is in the distal position, and the cam lobes 1172 are displacing the thread rails 1124 outwardly. In use, the user grips the handle 1130 and applies a proximally directed finger force to the trigger 1131 to displace the trigger 1131 proximally. Proximal displacement of the trigger 1131 disengages the rail threads 1125 from the coupling nut threads 1119 and configures the inflation device 1100 in the priming state as shown in FIG. 11C. The inflation device 1100 may be actuated when the user grips the trigger 1131 and displaces the trigger 1131 proximally. The trigger 1131 displaces the threaded sleeve 1165 proximally causing the internal threads 1173 to engage with the external threads 1174 of the handle feature 1166. Upon engagement of the threads 1173, 1174 and proximal displacement of the threaded sleeve 1165, the threaded sleeve 1165 is rotated about 90 degrees. Rotation of the threaded sleeve 1165 causes the cam shaft 1164 to rotate about 90 degrees. When the cam shaft 1164 is rotated about 90 degrees, the cam lobes 1172 disengage from the thread rails 1124 allowing the thread rails 1124 to be displaced inwardly such that the rail threads 1125 and the coupling nut threads 1119 disengage. The user may displace the plunger 1120 longitudinally to prime or deflate an inflatable medical device in fluid communication with the inflation device 1100.

When desired, the inflation device 1100 may be de-actuated by releasing the trigger 1131. The compression member 1171 can apply a distally directed force to the threaded sleeve 1165 causing the threaded sleeve 1165 and the trigger 1131 to be displaced distally. As the threaded sleeve 1165 is displaced distally, the internal threads 1173 and the external threads 1174 cause the threaded sleeve 1165 and the cam shaft 1164 to rotate in a clockwise direction about 90 degrees. When rotated about 90 degrees, the cam lobes 1172 engage the thread rails 1124 and displace the thread rails 1124 outwardly such that the rail threads 1125 and the coupling nut threads 1119 engage. The inflation device 1100 is in the pressurization state as depicted in FIG. 11B.

Figure 12A:
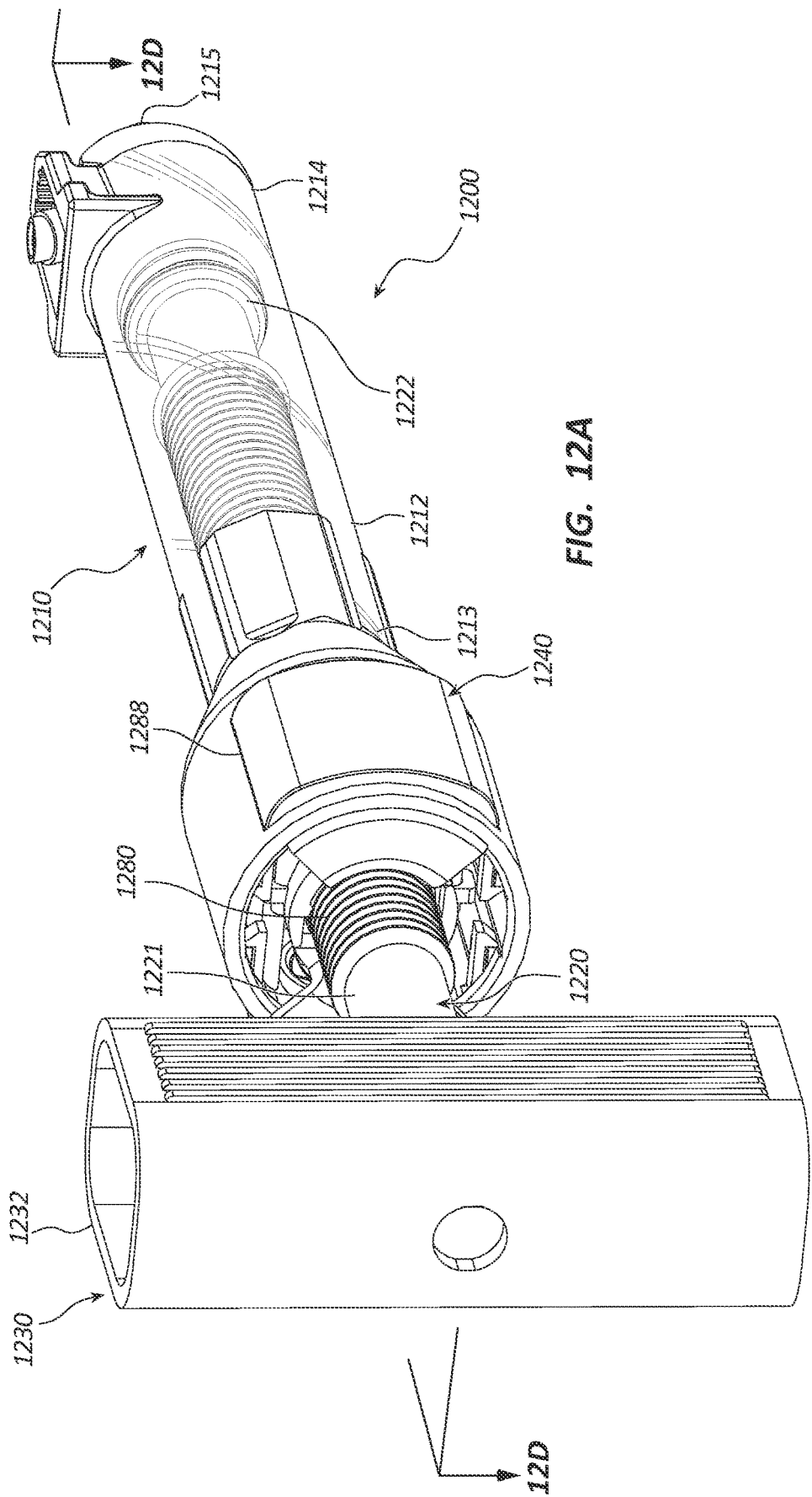
FIG. 12A is a perspective view of another embodiment of an inflation device with a trigger toggle member.
Figure 12B:
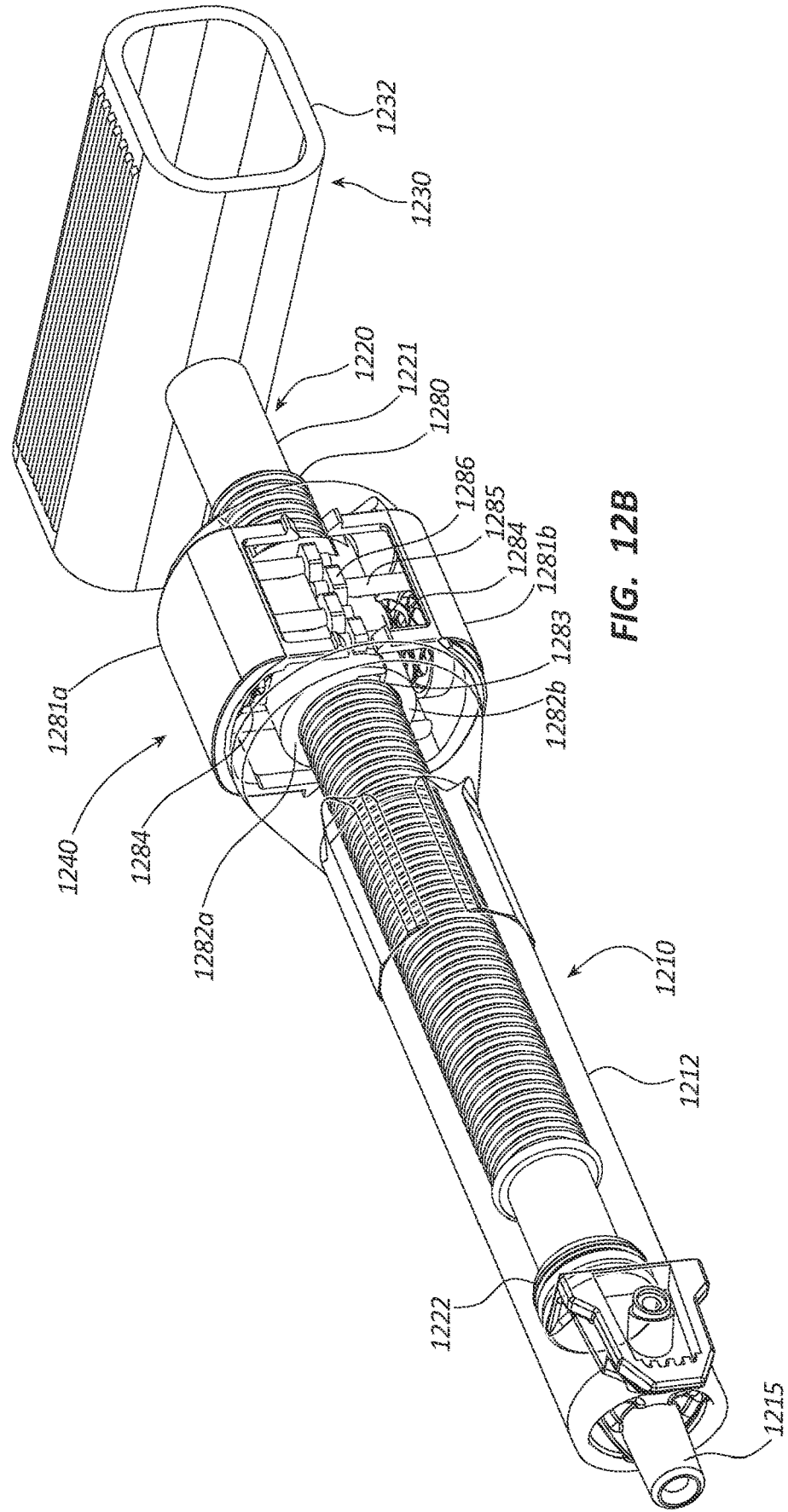
FIG. 12B is a perspective view, with a portion removed, of the inflation device of FIG. 12A in a pressurization state.
Figure 12C:
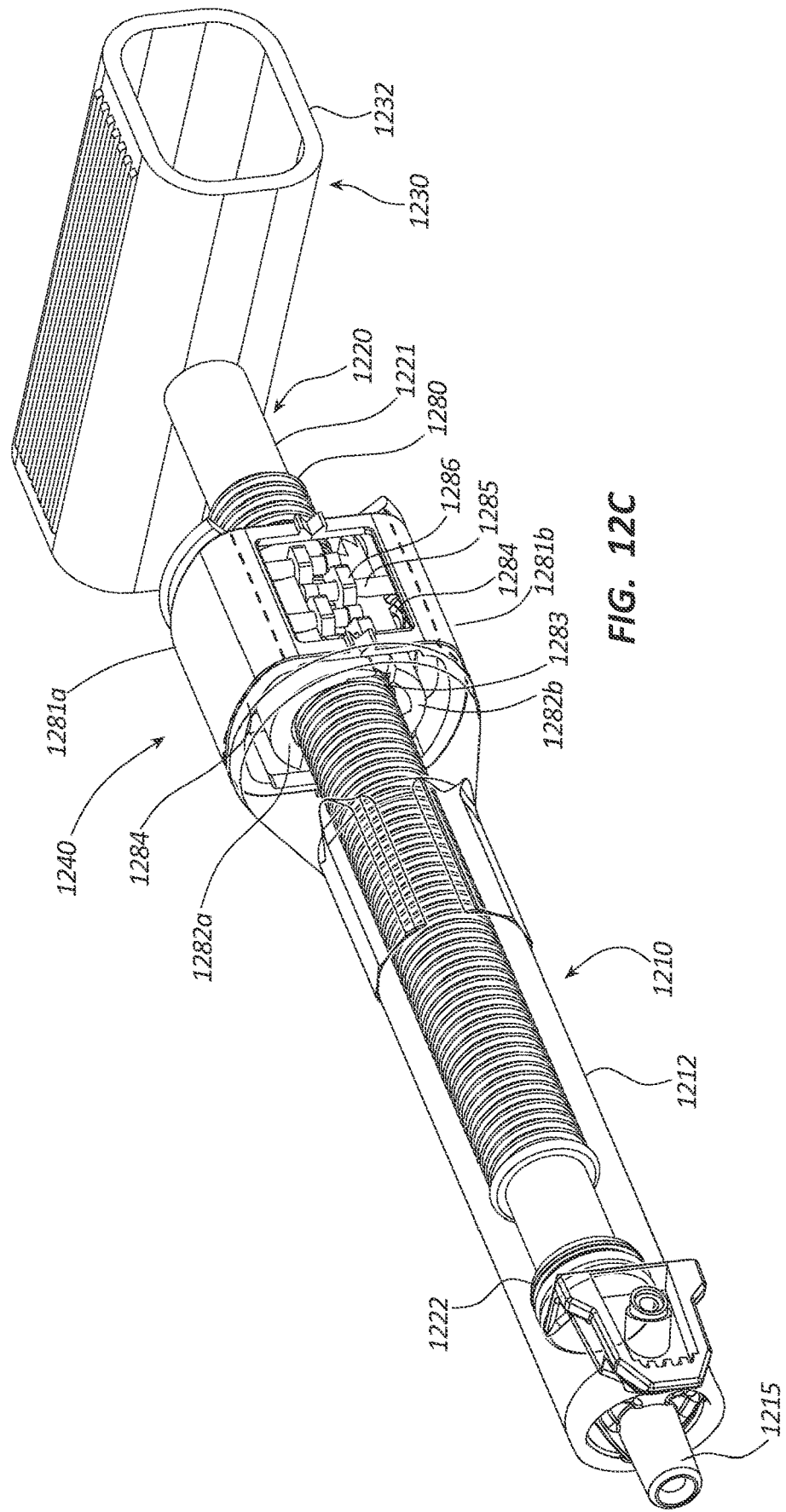
FIG. 12C is a perspective view, with a portion removed, of the inflation device of FIG. 12A in a priming state.
Figure 12D:
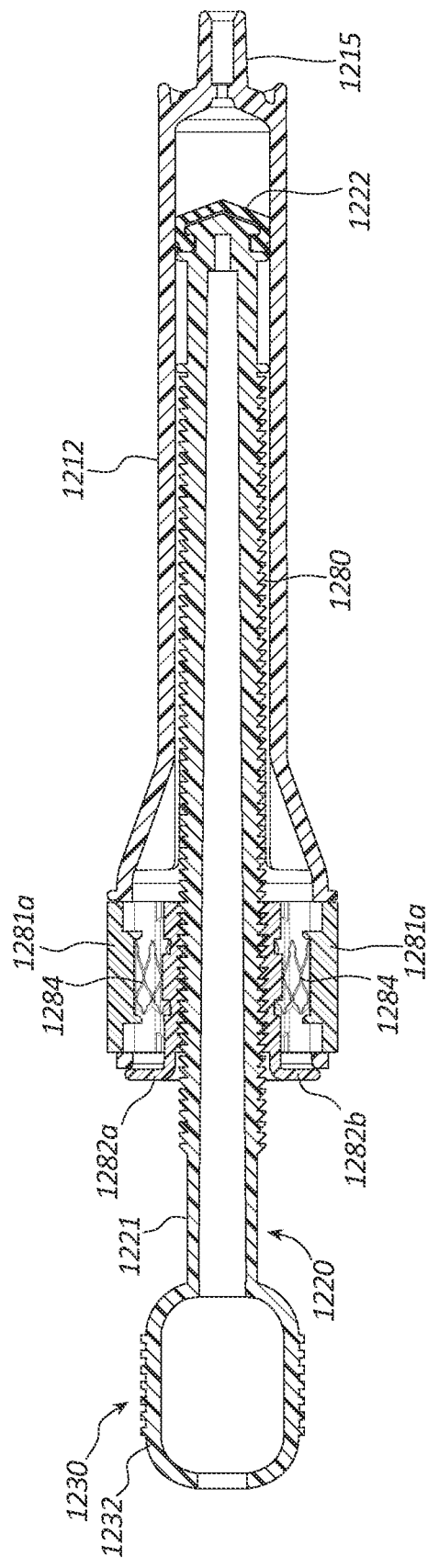
FIG. 12D is a cross-sectional view, taken through plane 12D-12D of FIG. 12A, of the inflation device of FIG. 12A in a pressurization state.
Figure 12E:
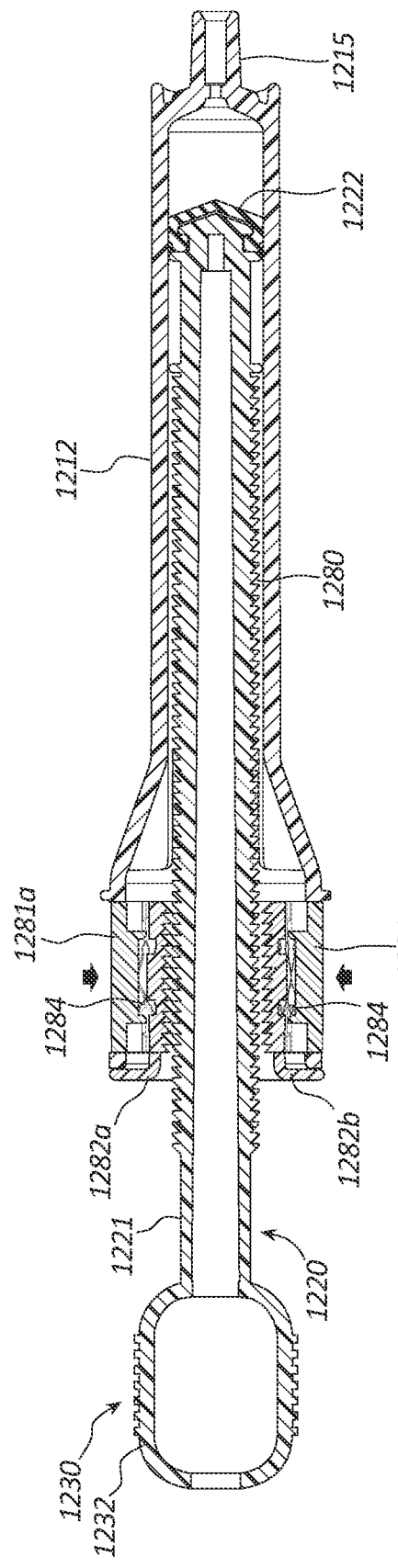
FIG. 12E is a cross-sectional view of the inflation device of FIG. 12A in a priming state.

FIGS. 12A-12C depict another embodiment of an inflation device 1200. In the illustrated embodiment, the inflation device 1200 is partially comprised of a syringe 1210. The inflation device 1200 includes three broad groups of components; each group may have numerous subcomponents and parts. The three broad component groups are: a body component such as syringe body 1212, a pressurization component such as plunger 1220, and a handle 1230.

The syringe body 1212 may be formed of a generally cylindrical hollow tube configured to receive the plunger 1220. The syringe body 1212 may include an inlet/outlet port 1215 located adjacent a distal end 1214 of the syringe body 1212

The plunger 1220 may be configured to be longitudinally displaceable within the syringe body 1212. The plunger 1220 may be comprised of a plunger shaft 1221 coupled to a plunger seal 1222 at the distal end of the plunger shaft 1221. The plunger shaft 1221 may also be coupled to the handle 1230 at the proximal end of the plunger shaft 1221, with the plunger shaft 1221 spanning the distance between the plunger seal 1222 and the handle 1230. The plunger 1220 may include plunger threads 1280. In the illustrated embodiment, the plunger threads 1280 are configured to circumnavigate the plunger shaft 1221 and extend over at least a portion of the plunger shaft 1221.

The handle 1230 broadly refers to the group of components coupled to the proximal end of the plunger 1220, some of which may be configured to be graspable by a user. In certain embodiments, the handle 1230 may be configured such that the user may manipulate the position of the plunger 1220 by manipulating the handle 1230. Further, in some embodiments, the handle 1230 may be an actuator mechanism configured to manipulate components of the inflation device 1200.

As illustrated in FIGS. 12A-12C, the handle 1230 includes a grip portion 1232. The grip portion 1232 may be configured to be gripped by a hand of a user. While gripping, the user may either rotate the handle 1230 or longitudinally displace the handle 1230 to inflate or deflate a medical device in fluid communication with the syringe 1210. The plunger shaft 1221 extends distally from the grip portion 1232. The plunger shaft 1221 may be fixedly coupled to the grip portion 1232.

As shown, the syringe 1210 includes a toggle member 1240. The toggle member 1240 may be configured to toggle the inflation device 1200 between a pressurization state and a priming state.

FIGS. 12A-12C depict the toggle member 1240 disposed adjacent the proximal end of the syringe body 1212. The toggle member includes a pair of buttons 1281*a*, 1281*b*, a pair of threaded shells 1282*a*, 1282*b*, and a compression member 1284. The buttons 1281*a*, 1281*b* are disposed within button openings 1288 in the syringe body 1212. The buttons 1281*a*, 1281*b* are configured to be displaced inwardly when the user applies an inwardly directed force with a finger. Each of the pair of buttons 1281*a*, 1281*b* are identical in form. Each of the pair of buttons 1281*a*, 1281*b* oppose each other and are disposed around the threaded shells 1282*a*, 1282*b*. The buttons 1281*a*, 1281*b* may include at least one post 1285 on each side extending radially inward. The post 1285 may slidingly pass through a guide 1286 and engage the threaded shell 1282*a*, 1282*b* that is positioned opposite of the button 1281*a*, 1281*b*. In other words, the post 1285 may extend from the button 1281*a* and engage with threaded shell 1282*b*. The post 1285*a* may be configured to displace the threaded shell 1282*b* radially outward when the button 1281*a* is displaced radially inward to disengage the shell threads 1283 from the plunger threads 1280. A similar action would take place with button 1281*b* and threaded shell 1282*b*. The pair of threaded shells 1282*a*, 1282*b* include the shell threads 1283 that are configured to engage with the plunger threads 1280. The threaded shells 1282*a*, 1282*b* are disposed around the plunger shaft 1221 such that each threaded shell 1282 circumferentially surrounds about 180 degrees of the plunger shaft 1221. The compression member 1284 is disposed between the buttons 1281*a*, 1281*b* and the threaded shells 1282*a*, 1282*b*. The compression member 1284 may be compressed when the buttons 1281*a*, 1281*b* are displaced inwardly and the threaded shells 1282*a*, 1282*b* are displaced outwardly. The compression member 1284 may apply an outwardly directed force to the buttons 1281*a*, 1281*b* and an inwardly directed force to the threaded shells 1282*a*, 1282*b* when the user releases the buttons 1281*a*, 1281*b*.

FIG. 12B depicts the inflation device 1200 in a pressurization state where the shell threads 1283 are engaged with the plunger threads 1280 and the buttons 1281*a*, 1281*b* are disposed outwardly. In use, the user may actuate the toggle member 1240 by applying an inwardly directed force to the buttons 1281*a*, 1281*b* with a finger and a thumb. The buttons 1281*a*, 1281*b* may be displaced inwardly and engaged with the threaded shells 1282*a*, 1282*b* such that the threaded shells 1282*a*, 1282*b* are displaced outwardly. When the threaded shells 1282*a*, 1282*b* are displaced outwardly, the shell threads 1283 disengage from the plunger threads 1280 and the inflation device 1200 transitions to the priming state as shown in FIG. 12C. The user may then grip the handle 1230 and longitudinally translate the plunger 1220 to prime or deflate the inflatable medical device in fluid communication with the inflation device 1200.

When desired, the toggle member 1240 may be de-actuated when the user releases the buttons 1281*a*, 1281*b*. The compression member 1284 applies an outwardly directed force to the buttons 1281*a*, 1281*b* to return the buttons 1281*a*, 1281*b* to an outward position. The compression member 1284 also applies an inwardly directed force to the threaded shells 1282*a*, 1282*b* to displace the threaded shells 1282*a*, 1282*b* inwardly where the shell threads 1283 engage with the plunger threads 1280. The inflation device 1200 may be converted to the pressurization state as shown in FIG. 12C.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

References to approximations are made throughout this specification, such as by use of the term "substantially." For each such reference, it is to be understood that, in some embodiments, the value, feature, or characteristic may be specified without approximation. For example, where qualifiers such as "about" and "substantially" are used, these terms include within their scope the qualified words in the absence of their qualifiers. For example, where the term "substantially perpendicular" is recited with respect to a feature, it is understood that in further embodiments, the feature can have a precisely perpendicular configuration.

Similarly, in the above description of embodiments, various features are sometimes grouped together in a single embodiment, figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment.

The claims following this written disclosure are hereby expressly incorporated into the present written disclosure, with each claim standing on its own as a separate embodiment. This disclosure includes all permutations of the independent claims with their dependent claims. Moreover, additional embodiments capable of derivation from the independent and dependent claims that follow are also expressly incorporated into the present written description.

Without further elaboration, it is believed that one skilled in the art can use the preceding description to utilize the invention to its fullest extent. The claims and embodiments disclosed herein are to be construed as merely illustrative and exemplary, and not a limitation of the scope of the present disclosure in any way. It will be apparent to those having ordinary skill in the art, with the aid of the present disclosure, that changes may be made to the details of the above-described embodiments without departing from the underlying principles of the disclosure herein. In other words, various modifications and improvements of the embodiments specifically disclosed in the description above are within the scope of the appended claims. Moreover, the order of the steps or actions of the methods disclosed herein may be changed by those skilled in the art without departing from the scope of the present disclosure. In other words, unless a specific order of steps or actions is required for proper operation of the embodiment, the order or use of specific steps or actions may be modified. The scope of the invention is therefore defined by the following claims and their equivalents.

EXEMPLARY EMBODIMENTS

The following embodiments are illustrative and exemplary and not meant as a limitation of the scope of the present disclosure in any way.

In one embodiment, an inflation device comprises:
a syringe body;
a plunger configured for advancement and retraction within the syringe body;
a coupling member comprising coupling member threads configured to constrain movement of the plunger within the syringe body,
wherein the plunger comprises plunger threads configured to be selectively engaged and disengaged with the coupling member threads, wherein the plunger threads are configured to be retractable from the coupling member threads;
a handle coupled to a proximal portion of the plunger;
a trigger operatively coupled to the handle and configured to retract the plunger threads from the coupling member threads to a plunger thread retracted state; and
a locking member configured to selectively lock the trigger in the thread retracted state.

The handle may comprise a crank member.

The plunger may comprise a sealing member disposed adjacent a distal end.

The syringe body may comprise an outlet port.

The syringe body may be in fluid communication with an inflatable medical device.

The trigger may be longitudinally displaceable relative to the handle.

The plunger threads may comprise a thread rail.

The locking member may comprise:
a pin; and
a latch disposed at an end of the pin,
wherein the pin and the latch are slidably disposed within the trigger,
wherein the latch is configured to engage a portion of the plunger when the trigger is in the thread retracted state.

The latch may restrain the trigger from displacement from the thread retracted state.

The inflation device may further comprise a resilient member configured to apply a force to the latch to disengage the latch from the plunger.

The latch may be disposed exterior to the plunger.

The latch may be disposed within the plunger.

The locking member may comprise:
a pin; and
a latch disposed at an end of the pin,
wherein the pin and the latch are slidably disposed within the plunger,
wherein the latch engages a portion of the plunger when the trigger is in the thread retracted state.

The latch may restrain the trigger from displacement from the thread retracted state.

The inflation device may further comprise a resilient member configured to apply a force to the latch to disengage the latch from the plunger.

The latch may be disposed within the plunger.

The locking member may comprise:
a pin;
a leaf spring latch coupled to the handle; and
a shoulder disposed on the plunger threads and configured to selectively engage with the leaf spring latch.

The leaf spring latch may be in axial alignment with and engages the shoulder when the trigger is in the thread retracted state.

The pin may be configured to laterally displace the plunger threads, wherein the shoulder is axially unaligned with and disengaged from the leaf spring latch.

The locking member may comprise:
a ring rotatably disposed at least partially around a portion of the plunger;
a pin extending outwardly from the plunger threads; and
a rib disposed at least partially around a portion of the plunger.

The ring may comprise a groove configured to receive the rib.

The ring may be rotatable when the trigger is in the thread retracted state.

The rotated ring may apply an inwardly directed force to the pin to maintain the trigger in the thread retracted state.

The locking member may comprise:
a rotatable ring disposed around a portion of the plunger; and
a first rib and a second rib disposed at least partially around a portion of the plunger, wherein the ring is disposed between the first rib and the second rib.

The ring may comprise an inner recess portion configured to receive a portion of the plunger threads, and a non-recess portion configured to engage with a portion of the plunger threads.

The ring may be rotatable when the trigger is in the thread retracted state.

The non-recess portion of the ring may apply an inwardly directed force to the plunger threads to maintain the trigger in the thread retracted state.

The locking member may comprise:
a pin;
a pin receiver disposed in the trigger; and
a resilient member.

The pin may be in axial alignment with the pin receiver when the trigger is in the thread retracted state.

The pin may be displaced such that an end portion is received within the pin receiver to maintain the trigger in the thread retracted state.

The resilient member may apply a force to the pin to displace an end of the pin from the pin receiver to release the trigger from the thread retracted state.

The locking member may comprise:
a rotatable knob coupled to the handle;
a first magnet and a second magnet coupled to the handle; and
a third magnet coupled to a proximal end of the plunger threads.

The first magnet and the second magnet may be disposed on a knob shaft opposing one another.

The first magnet may be oriented with a first magnetic pole directed outwardly, the second magnet may be oriented with a second magnetic pole directed outwardly, and the third magnet may be oriented with the first magnetic pole directed outwardly.

The first magnet may be repelled by the third magnet, and the second magnet may be attracted to the third magnet.

The trigger may be in the thread retracted state when the second magnet is attracted to the third magnet.

The knob may be rotated to align the first magnet or the second magnet with the third magnet.

The locking member may comprise:
a rotatable knob coupled to the handle;
a cam shaft coupled to the knob; and
a cam passage disposed in the trigger, wherein the cam shaft passes through the cam passage.

The cam shaft may comprise a cam lobe extending to one side of a longitudinal axis of the cam shaft.

The cam shaft may include an engaged state where the cam lobe engages with the cam passage and the trigger is in the thread retracted state.

Rotation of the knob may transition the cam shaft to and from the engaged state.

The locking member may be configured to rotate the plunger about a longitudinal axis when the trigger is displaced proximally.

The plunger may be rotated about 90 degrees for a first proximal displacement of the trigger, and the plunger may be rotated about 90 degrees for a second proximal displacement of the trigger.

The locking member may comprise:
cam lobes disposed on the plunger, wherein the cam lobes are configured to selectively engage the plunger threads to engage the plunger threads with the coupling member threads; and
a rotation member rotatably coupled to the trigger, wherein the rotation member rotates the plunger when the trigger is displaced proximally.

The cam lobes may engage the plunger threads upon the first proximal displacement of the trigger and disengage from the plunger threads upon the second proximal displacement of the trigger.

The trigger may be in the thread retracted state following the second proximal displacement of the trigger.

The rotation member may comprise:
an upper cam fixedly coupled to the handle and extending distally;
a lower cam fixedly coupled to a proximal end of the plunger and extending proximally, wherein the lower cam is configured to engage with the upper cam and to rotate relative to the upper cam;
a barrel rotatably coupled to the trigger and configured to be longitudinally displaceable relative to the upper cam and the lower cam by the trigger;
a barrel guide disposed on an inside surface of the barrel;
a lower cam guide disposed on an outer surface of the lower cam, wherein the barrel guide is configured to be longitudinally displaceable relative to the lower cam guide, and the lower cam guide is configured to be rotated relative to the barrel guide by the barrel guide; and
a resilient member disposed between the lower cam and the barrel, wherein the resilient member is configured to apply a distally directed force to the barrel to displace the trigger distally.

The upper and lower claims may be configured such that:
the lower cam comprises inclined surfaces,
the upper cam comprises inclined surfaces, and
the lower cam inclined surfaces are configured to operatively couple with the upper cam inclined surfaces.

In one embodiment an inflation device assembly comprises:
a syringe body;
a plunger configured for advancement and retraction within the syringe body;
a coupling member comprising coupling member threads configured to constrain movement of the plunger within the syringe body,
wherein the plunger comprises plunger threads configured to be selectively engaged and disengaged with the coupling member threads, wherein the plunger threads are configured to be retractable from the coupling member threads;
a handle coupled to a proximal portion of the plunger;
a trigger operatively coupled to the handle and configured to retract the plunger threads from the coupling member threads to a plunger thread retracted state; and
a locking member configured to selectively lock the trigger in the thread retracted state,
wherein the locking member is configured to rotate the plunger about a longitudinal axis when the trigger is displaced proximally.

The plunger may be rotated about 90 degrees for a first proximal displacement of the trigger, and the plunger may be rotated about 90 degrees for a second proximal displacement of the trigger.

The locking member may comprise:
cam lobes disposed on the plunger, wherein the cam lobes are configured to selectively engage the plunger threads to engage the plunger threads with the coupling member threads; and
a rotation member rotatably coupled to the trigger, wherein the rotation member rotates the plunger when the trigger is displaced proximally.

The cam lobes may engage the plunger threads upon the first proximal displacement of the trigger and disengage from the plunger threads upon the second proximal displacement of the trigger.

The trigger may be in the thread retracted state following the second proximal displacement of the trigger.

The rotation member may comprise:
an upper cam fixedly coupled to the handle and extending distally;
a lower cam fixedly coupled to a proximal end of the plunger and extending proximally, wherein the lower cam is configured to engage with the upper cam and to rotate relative to the upper cam;
a barrel rotatably coupled to the trigger and configured to be longitudinally displaceable relative to the upper cam and the lower cam by the trigger;
a barrel guide disposed on an inside surface of the barrel;
a lower cam guide disposed on an outer surface of the lower cam, wherein the barrel guide is configured to be longitudinally displaceable relative to the lower cam guide, and the lower cam guide is configured to be rotated relative to the barrel guide by the barrel guide; and
a resilient member disposed between the lower cam and the barrel, wherein the resilient member is configured to apply a distally directed force to the barrel to displace the trigger distally.

The upper and lower cams may be configured such that:
the lower cam comprises inclined surfaces,
the upper cam comprises inclined surfaces, and
the lower cam inclined surfaces are configured to operatively couple with
the upper cam inclined surfaces when the trigger is displaced proximally.

In one embodiment an inflation device assembly comprises:
a syringe body;
a plunger configured for advancement and retraction within the syringe body;
a coupling member comprising coupling member threads configured to constrain movement of the plunger within the syringe body,
wherein the plunger comprises plunger threads configured to be selectively engaged and disengaged with the coupling member threads, wherein the plunger threads are configured to be retractable from the coupling member threads;

a handle coupled to a proximal portion of the plunger;
a trigger operatively coupled to the handle and configured to retract the plunger threads from the coupling member threads to a plunger thread retracted state; and
a locking member configured to selectively lock the trigger in the thread retracted state,
wherein the locking member is configured to rotate the plunger about a longitudinal axis when the trigger is displaced proximally.

The locking member may comprise:
cam lobes disposed on the plunger, wherein the cam lobes are configured to selectively engage the plunger threads to engage the plunger threads with the coupling member threads; and
a rotation member rotatably coupled to the trigger, wherein the rotation member rotates the plunger when the trigger is displaced proximally.

The rotation member may rotate the plunger about 90 degrees when the trigger is displaced proximally.

The cam lobes may disengage the plunger threads when the trigger is displaced distally from the thread retracted state.

The rotation member may comprise:
an externally threaded projection coupled to the handle and extending distally;
an internally threaded sleeve rotatably coupled to the trigger and moveably coupled to the plunger,
wherein sleeve threads are configured to engage projection threads to rotate the sleeve relative to the projection,
wherein the sleeve is configured to rotate the plunger relative to the plunger threads,
wherein the cam lobes disengage the plunger threads when the trigger is displaced proximally to the thread retracted state.

In one embodiment an inflation device assembly may comprise:
a syringe body;
a plunger configured for advancement and retraction within the syringe body;
a toggle member operatively coupled to the syringe body and comprising shell threads configured to constrain movement of the plunger within the syringe body,
wherein the plunger comprises plunger threads configured to be selectively engaged and disengaged with the shell threads, wherein the shell threads are configured to be selectively displaceable from the plunger threads by the toggle member; and
a handle coupled to a proximal portion of the plunger.

The toggle member may further comprise:
a first threaded shell and a second threaded shell comprising the toggle member threads, wherein the first and second threaded shells are opposingly positioned around the plunger;
a first button and a second button, wherein the first and second buttons are opposingly positioned and disposed around the first and second threaded shells; and
a compression member disposed between each of the buttons and threaded shells.

The first button and second button may be configured such that:
the first button is inwardly displaceable and configured to engage with the second threaded shell to displace the second threaded shell outwardly such that the toggle member threads are disengaged from the plunger threads, and
the second button is inwardly displaceable and configured to engage with the first threaded shell to displace the first threaded shell outwardly such that the toggle member threads are disengaged from the plunger threads.

The compression member may apply an outwardly directed force to the first and second buttons and an inwardly directed force to the first and second threaded shells such that the first and second buttons are displaced outwardly and the first and second threaded shells are displaced inwardly, wherein the toggle member threads engage with the plunger threads.

One method of priming an inflation device comprises:
obtaining the inflation device, wherein the inflation device comprises a trigger, a plunger, and plunger threads;
displacing the trigger proximally to a proximal position; and
actuating a locking member to maintain the trigger in the proximal position.

The inflation device may be configured such that:
the locking member comprises a pin and a latch,
actuating the locking member comprises:
applying a force to the pin to displace the latch, and
engaging the latch with a shoulder of the inflation device.

The locking member may comprise a latch and shoulder, wherein the latch and the shoulder are in axial alignment;
wherein actuating the locking member comprises:
displacing the shoulder proximally, and
engaging the latch with the shoulder.

The method may further comprise de-actuating the locking member, wherein the shoulder is displaced from axial alignment with the latch.

The locking member may comprise a ring disposed over a rib and a pin;
wherein actuating the locking member comprises:
rotating the ring over the rib to engage the pin.

The locking member may comprise a ring disposed between two ribs;
wherein actuating the locking member comprises:
rotating the ring between the two ribs to engage the plunger threads.

The locking member may comprise a pin and a pin receiver disposed in the trigger;
wherein actuating the locking member comprises:
aligning the pin with the pin receiver; and
depressing the pin to dispose a portion of the pin in the pin receiver.

The locking member may comprise a knob having a shaft, a first magnet, a second magnet, and a third magnet;
wherein the first magnet is attracted to the third magnet, and the second magnet is repelled by the third magnet;
wherein actuating the locking member comprises:
rotating the knob such that the first magnet is proximate to and oriented toward the third magnet.

The first magnet may be coupled to the shaft such that a first magnetic pole is directed outwardly,
wherein the second magnet is coupled to the shaft such that a second magnetic pole is directed outwardly,
wherein the third magnet is coupled to the trigger such that the second magnetic pole is oriented proximally.

The locking member may comprise a knob, a cam shaft coupled to the knob, and a cam passage disposed in the trigger;
wherein actuating the locking member comprises:
rotating the knob such that the cam shaft engages the cam passage.

The locking member may comprise a rotation member coupled to the plunger, and a handle feature;
wherein actuating the locking member comprises;
displacing the rotation member proximally such that the rotation member engages with the handle feature;
rotating the rotation member such that the plunger is rotated; and
displacing the trigger distally.

One method of priming an inflation device comprises:
obtaining the inflation device, wherein the inflation device comprises a syringe body, a trigger, a plunger, and a toggle member;
displacing the trigger proximally to a proximal position;
rotating the toggle member in a first direction;
displacing the plunger longitudinally within the syringe body;
displacing the trigger distally to a distal position; and
rotating the toggle member in a second direction.

The toggle member may comprise:
an internally threaded sleeve; and
an externally threaded handle feature,
wherein a sleeve thread is configured to engage with a handle feature thread when the trigger is displaced proximally to rotate the sleeve in a first direction, and
wherein the sleeve thread is configured to engage with the handle feature thread when the trigger is displaced distally to rotate the sleeve in a second direction.

The inflation device may further comprise:
a cam shaft having cam lobes;
plunger threads; and
coupling threads.

Rotating the toggle member in the first direction may comprise:
rotating the cam shaft in the first direction;
disengaging the cam lobes from the plunger threads; and
disengaging the plunger threads from the coupling threads.

Rotating the toggle member in the second direction may comprise:
rotating the cam shaft in the second direction;
engaging the cam lobes with the plunger threads; and
engaging the plunger threads with the coupling threads.

One method of priming an inflation device comprises:
obtaining the inflation device, wherein the inflation device comprises a syringe body, a threaded plunger, and a threaded toggle member;
displacing the toggle member inwardly to an actuated position;
displacing the threaded plunger longitudinally within the syringe body; and
displacing the toggle member outwardly to a non-actuated position.

The toggle member may comprise:
a pair of threaded shells; and
a pair of buttons disposed over the threaded shells.

Displacing the toggle member inwardly to an actuated position may comprise:
displacing the pair of buttons inwardly; and
displacing the pair of threaded shells outwardly, wherein the pair of threaded shells disengage from the threaded plunger.

Displacing the toggle member outwardly to a non-actuated position may comprise:
displacing the pair of buttons outwardly; and
displacing the pair of threaded shells inwardly, wherein the pair of threaded shells engage with the threaded plunger.

The invention claimed is:

1. An inflation device assembly, comprising: a syringe body;
a plunger configured for advancement and retraction within the syringe body;
a coupling member comprising coupling member threads configured to constrain movement of the plunger within the syringe body,
wherein the plunger comprises plunger threads configured to be selectively engaged and disengaged with the coupling member threads, wherein the plunger threads are configured to be retractable from the coupling member threads;
a handle coupled to a proximal portion of the plunger;
a trigger operatively coupled to the handle and configured to retract the plunger threads from the coupling member threads to a plunger thread retracted state; and
a locking member configured to selectively lock the trigger in the thread retracted state wherein,
the locking member comprises:
a pin; and
a latch disposed at an end of the pin,
wherein the pin and the latch are slidably disposed within the trigger, wherein the latch is configured to engage a portion of the plunger when the trigger is in the thread retracted state.

2. The inflation device assembly of claim 1, wherein the latch restrains the trigger from displacement from the thread retracted state.

3. The inflation device assembly of claim 2, further comprising a resilient member configured to apply a force to the latch to disengage the latch from the plunger.

4. The inflation device assembly of claim 1, wherein the latch is disposed exterior to the plunger.

5. The inflation device assembly of claim 1, wherein the latch is disposed within the plunger.

6. An inflation device assembly, comprising: a syringe body;
a plunger configured for advancement and retraction within the syringe body;
a coupling member comprising coupling member threads configured to constrain movement of the plunger within the syringe body,
wherein the plunger comprises plunger threads configured to be selectively engaged and disengaged with the coupling member threads, wherein the plunger threads are configured to be retractable from the coupling member threads;
a handle coupled to a proximal portion of the plunger;
a trigger operatively coupled to the handle and configured to retract the plunger threads from the coupling member threads to a plunger thread retracted state; and
a locking member configured to selectively lock the trigger in the thread retracted state
wherein the locking member comprises:
a pin;
a pin receiver disposed in the trigger; and
a resilient member
wherein the pin is displaced such that an end portion is received within the pin receiver to maintain the trigger in the thread retracted state and
wherein the resilient member applies a force to the pin to displace an end of the pin from the pin receiver to release the trigger from the thread retracted state.

7. The inflation device assembly of claim 6, wherein the pin is in axial alignment with the pin receiver when the trigger is in the thread retracted state.

8. The inflation device assembly of claim 6, wherein the resilient member applies a force to the pin to displace an end of the pin from the pin receiver to release the trigger from the thread retracted state.

9. An inflation device assembly, comprising: a syringe body;
- a plunger configured for advancement and retraction within the syringe body;
- a coupling member comprising coupling member threads configured to constrain movement of the plunger within the syringe body,
- wherein the plunger comprises plunger threads configured to be selectively engaged and disengaged with the coupling member threads, wherein the plunger threads are configured to be retractable from the coupling member threads;
- a handle coupled to a proximal portion of the plunger;
- a trigger operatively coupled to the handle and configured to retract the plunger threads from the coupling member threads to a plunger thread retracted state; and
- a locking member configured to selectively lock the trigger in the thread retracted state wherein the locking member comprises a pin and axial displacement of the pin locks the trigger.

10. The inflation device assembly of claim 9, wherein the pin is configured to engage a portion of the plunger when the trigger is in the thread retracted state.

11. The inflation device assembly of claim 10, wherein the pin is disposed exterior to the plunger.

12. The inflation device assembly claim 10, wherein the pin is disposed within the plunger.

13. The inflation device assembly of claim 9, wherein the pin restrains the trigger from displacement from the thread retracted state.

14. The inflation device assembly of claim 13, further comprising a resilient member configured to apply a force to the pin to disengage from the plunger.

* * * * *